(12) United States Patent
Goetz et al.

(10) Patent No.: US 11,787,857 B2
(45) Date of Patent: *Oct. 17, 2023

(54) COMPOUNDS THAT MODULATE THE INTERACTION OF VISTA AND VSIG3 AND METHODS OF MAKING AND USING

(71) Applicant: BIO-TECHNE CORPORATION, Minneapolis, MN (US)

(72) Inventors: Christine Goetz, Blaine, MN (US); Christopher Hammerbeck, Shoreview, MN (US); Christopher Valley, Minnetonka, MN (US); Jody Bonnevier, Chanhassen, MN (US); Birte Aggeler, Minneapolis, MN (US); Jinghua Wang, Shoreview, MN (US); Guoping Wu, Blaine, MN (US); Vassilios Kalabokis, Fridley, MN (US); Jose Fernando Bazan, Stillwater, MN (US)

(73) Assignee: BIO-TECHNE CORPORATION, Minneapolis, MN (US)

( * ) Notice: Subject to any disclaimer, the term of this patent is extended or adjusted under 35 U.S.C. 154(b) by 381 days.

This patent is subject to a terminal disclaimer.

(21) Appl. No.: 16/966,561

(22) PCT Filed: Feb. 1, 2019

(86) PCT No.: PCT/US2019/016301
§ 371 (c)(1),
(2) Date: Jul. 31, 2020

(87) PCT Pub. No.: WO2019/152810
PCT Pub. Date: Aug. 8, 2019

(65) Prior Publication Data
US 2020/0362031 A1 Nov. 19, 2020

Related U.S. Application Data

(60) Provisional application No. 62/627,478, filed on Feb. 7, 2018, provisional application No. 62/625,594, filed on Feb. 2, 2018.

(51) Int. Cl.
C07K 16/28 (2006.01)
C07K 14/705 (2006.01)
(Continued)

(52) U.S. Cl.
CPC ............ C07K 16/28 (2013.01); C07K 14/705 (2013.01); C07K 14/70532 (2013.01);
(Continued)

(58) Field of Classification Search
CPC C07K 16/28; C07K 14/705; C07K 14/70532; C07K 14/78; C07K 16/2827;
(Continued)

(56) References Cited

U.S. PATENT DOCUMENTS 4,439,196 A 3/1984 Higuchi
4,447,224 A 5/1984 DeCant, Jr. et al.
(Continued)

FOREIGN PATENT DOCUMENTS

EP 2275544 A2 1/2011
EP 1176195 B1 5/2013
(Continued)

OTHER PUBLICATIONS

Yang Wei, et al.: "Construction of a versatile expression library for all human single-pass transmembrane proteins for receptor pairings by high throughput screening", Journal of Biotechnology, vol. 260, published Oct. 20, 2017 (Year: 2017).*
(Continued)

Primary Examiner — Adam Weidner
Assistant Examiner — Ashley H. Gao
(74) Attorney, Agent, or Firm — Mueting Raasch Group

(57) ABSTRACT

Described herein are polyclonal and monoclonal antibodies that binds to VSIG3, compounds that modulate the interaction of VISTA and VSIG3, and methods of making and using the polyclonal and monoclonal antibodies and compounds.

(Continued)

Also described herein are methods that include modulating the interaction of VISTA and VSIG3 by introducing a compound that modulates the interaction of VISTA and SIG3.

20 Claims, 25 Drawing Sheets

Specification includes a Sequence Listing.

(51) Int. Cl.
    *C07K 14/78*     (2006.01)
    *A61K 38/00*     (2006.01)

(52) U.S. Cl.
    CPC .......... *C07K 14/78* (2013.01); *C07K 16/2827* (2013.01); *A61K 38/00* (2013.01); *C07K 2317/21* (2013.01); *C07K 2317/76* (2013.01); *C07K 2319/30* (2013.01)

(58) Field of Classification Search
    CPC ............ C07K 2317/21; C07K 2317/76; C07K 2319/30; A61K 38/00
    See application file for complete search history.

(56) References Cited

U.S. PATENT DOCUMENTS

| | | |
|---|---|---|
| 4,447,233 A | 5/1984 | Mayfield |
| 4,486,194 A | 12/1984 | Josso et al. |
| 4,487,603 A | 12/1984 | Harris |
| 4,596,556 A | 6/1986 | Morrow et al. |
| 4,741,900 A | 5/1988 | Alvarez et al. |
| 4,790,824 A | 12/1988 | Morrow et al. |
| 4,941,880 A | 7/1990 | Burn |
| 5,064,413 A | 11/1991 | McKinnon et al. |
| 5,223,409 A | 6/1993 | Ladner et al. |
| 5,283,173 A | 2/1994 | Fields et al. |
| 5,312,335 A | 5/1994 | McKinnon et al. |
| 5,383,851 A | 1/1995 | McKinnon, Jr. et al. |
| 5,399,163 A | 3/1995 | Peterson et al. |
| 5,624,821 A | 4/1997 | Winter et al. |
| 5,648,260 A | 7/1997 | Winter et al. |
| 5,677,425 A | 10/1997 | Bodmer et al. |
| 5,714,350 A | 2/1998 | Co et al. |
| 5,869,045 A | 2/1999 | Hellstrom et al. |
| 5,932,448 A | 8/1999 | Tso et al. |
| 6,121,022 A | 9/2000 | Presta et al. |
| 6,165,745 A | 12/2000 | Ward et al. |
| 6,194,551 B1 | 2/2001 | Idusogie et al. |
| 6,277,375 B1 | 8/2001 | Ward |
| 6,350,861 B1 | 2/2002 | Co et al. |
| 6,562,576 B2 | 5/2003 | Manfredi |
| 6,790,624 B2 | 9/2004 | Mayer |
| 6,982,323 B1 | 1/2006 | Wang et al. |
| 9,381,244 B2 | 7/2016 | Noelle |
| 2004/0110704 A1 | 6/2004 | Yamane et al. |
| 2006/0025576 A1 | 2/2006 | Miller et al. |
| 2006/0034852 A1 | 2/2006 | Rixon et al. |
| 2008/0069820 A1 | 3/2008 | Fuh et al. |
| 2014/0220012 A1 | 8/2014 | Noelle et al. |
| 2014/0341920 A1 | 11/2014 | Noelle |
| 2016/0083472 A1 | 3/2016 | Noelle et al. |
| 2016/0159927 A1 | 6/2016 | Molloy et al. |
| 2019/0194322 A1 | 6/2019 | Kalabokis et al. |
| 2020/0362031 A1 | 11/2020 | Goetz et al. |

FOREIGN PATENT DOCUMENTS

| | | |
|---|---|---|
| WO | WO 90/02809 A1 | 3/1990 |
| WO | WO 91/17271 A1 | 11/1991 |
| WO | WO 92/01047 A1 | 1/1992 |
| WO | WO 92/01288 A1 | 1/1992 |
| WO | WO 92/09690 A3 | 6/1992 |
| WO | WO 92/15679 A1 | 9/1992 |
| WO | WO 92/18619 A1 | 10/1992 |
| WO | WO 92/20791 A1 | 11/1992 |
| WO | WO 99/54342 A1 | 10/1999 |
| WO | WO 00/42072 A3 | 7/2000 |
| WO | WO 01/00814 A3 | 1/2001 |
| WO | WO 02/043478 A2 | 6/2002 |
| WO | WO 02/092780 A3 | 11/2002 |
| WO | WO 03/035835 A2 | 5/2003 |
| WO | WO 03/074679 A2 | 9/2003 |
| WO | WO 06/050247 A2 | 5/2006 |
| WO | WO 06/050262 A2 | 5/2006 |
| WO | WO 13/184912 A2 | 12/2013 |
| WO | 2015/097536 | 7/2015 |
| WO | WO 18/027042 A1 | 2/2018 |
| WO | WO 19/152810 A1 | 8/2019 |

OTHER PUBLICATIONS

McCarthy et al. (J. Immunol. Methods, 251(1-2): 137-149, 2001) (Year: 2001).*
Lin et al. (African Journal of Biotechnology, 10(79):18294-18302, 2011) (Year: 2011).*
Mariuzza (Annu. Rev. Biophys. Biophys. Chem., 16: 139-159, 1987) (Year: 1987).*
International Search Report and Written Opinion for PCT/US19/16301 dated Apr. 18, 2019, 12 pages.
International Preliminary Report on Patentability for PCT/US19/16301 dated Aug. 13, 2020, 10 pages.
Bendig, "Humanization of Rodent Monoclonal Antibodies by CDR Grafting" Methods: A Companion to Methods in Enzymology, 1995; 8:83-93.
Berglund et al., The epitope space of the human proteome. Protein Sci 17, 606-613 (2008).
Chen et al., Epitope-directed antibody selection by site-specific photocrosslinking. Sci Adv 6, eaaz7825 (2020).
Colman, Effects of amino acid sequence changes on antibody-antigen interactions. Res Immunol 145, 33-36 (1994).
Edwards et al., The remarkable flexibility of the human antibody repertoire; isolation of over one thousand different antibodies to a single protein, BLyS. J Mol Biol 334, 103-118 (2003).
Mehta et al., An engineered antibody binds a distinct epitope and is a potent inhibitor of murine and human VISTA. Sci Rep 10, 15171 (2020).
Murphy et al., Enhancing recombinant antibody performance by optimally engineering its format. J Immunol Methods 463, 127-133 (2018).
Padlan, X-ray crystallography of antibodies. Adv Protein Chem 49, 57-133 (1996).
Paul (Ed.), Fundamental Immunology, Third Edition, Raven Press, New York. Title Page, Publisher's Page and pp. 292-295 from Chapter 9.
R & D Systems, "Human/Mouse VSIG3 Antibody" AF4915 Datasheet. Copyright 2021; 6 pages.
Rudikoff et al., Single amino acid substitution altering antigen-binding specificity. Proc Natl Acad Sci U S A 79, 1979-1983 (1982).
Wang et al., VSIG-3 as a ligand of VISTA inhibits human T-cell function. Immunology 156, 74-85 (2019).
Watanabe et al., Identification of immunoglobulin superfamily 11 (IGSF11) as a novel target for cancer immunotherapy of gastrointestinal and hepatocellular carcinomas. Cancer Sci 96, 498-506 (2005).
Yuan et al., VISTA: A Mediator of Quiescence and a Promising Target in Cancer Immunotherapy. Trends Immunol 42, 209-227 (2021).
Horita et al., High-resolution crystal structure of the therapeutic antibody pembrolizumab bound to the human PD-1. *Sci Rep* 6, 35297 (2016).
International Search Report and Written Opinion for PCT/US17/45314 dated Nov. 6, 2017, 15 pages.
International Preliminary Report on Patentability for PCT/US17/45314 dated Feb. 14, 2019, 8 pages.

(56) References Cited

OTHER PUBLICATIONS

Jang et al., Synaptic adhesion molecule IgSF11 regulates synaptic transmission and plasticity. Nat Neurosci 19, 84-93 (2016).
Jones et al., Replacing the complementarity-determining regions in a human antibody with those from a mouse. Nature 321, 522-525 (1986).
Kohler et al., Continuous cultures of fused cells secreting antibody of predefined specificity. Nature 256, 495-497 (1975).
Kohler et al., Derivation of specific antibody-producing tissue culture and tumor lines by cell fusion. Eur J Immunol 6, 511-519 (1976).
Kostelny et al., Formation of a bispecific antibody by the use of leucine zippers. J Immunol 148, 1547-1553 (1992).
Lazar-Molnar et al., Crystal structure of the complex between programmed death-1 (PD-1) and its ligand PD-L2. Proc Natl Acad Sci U S A 105, 10483-10488 (2008).
Lin et al., the PD-1/PD-L1 complex resembles the antigen-binding Fv domains of antibodies and T cell receptors. Proc Natl Acad Sci U S A 105, 3011-3016 (2008).
Liu et al., Immune-checkpoint proteins VISTA and PD-1 nonredundantly regulate murine T-cell responses. Proc Natl Acad Sci U S A 112, 6682-6687 (2015).
Malashkevich et al., The crystal structure of a five-stranded coiled coil in COMP: a prototype ion channel? Science 274, 761-765 (1996).
Meyers et al. (Comput. Appl. Biosci., 4: 11-17 (1988)).
Mueller et al., Humanized porcine VCAM-specific monoclonal antibodies with chimeric IgG2/G4 constant regions block human leukocyte binding to porcine endothelial cells. Mol Immunol 34, 441-452 (1997).
Needleman et al., A general method applicable to the search for similarities in the amino acid sequence of two proteins. J Mol Biol 48, 443-453 (1970).
Swann et al., Considerations for the development of therapeutic monoclonal antibodies. Curr Opin Immunol 20, 493-499 (2008).
Takeda et al., Construction of chimaeric processed immunoglobulin genes containing mouse variable and human constant region sequences. Nature 314, 452-454 (1985).
Tomlinson et al., the repertoire of human germline VH sequences reveals about fifty groups of VH segments with different hypervariable loops. J Mol Biol 227, 776-798 (1992).
Traunecker et al., Bispecific single chain molecules (Janusins) target cytotoxic lymphocytes on HIV infected cells. EMBO J 10, 3655-3659 (1991).
Wang et al., "VSIG-3/IGSF11 is a ligand of VISTA/PD-1H and inhibits human T cell function", J. Immunol, 198 (1 Supplement) 154.1 (May 1, 2017).
Yang et al., Construction of a versatile expression library for all human single-pass transmembrane proteins for receptor pairings by high throughput screening. J Biotechnol 260, 18-30 (2017).
"About Us: R&D Systems" Retrieved on Jan. 19, 2022. Copyright 2022. Retrieved from: www.rndsystems.com/about-us. 2 pages.
"Bio-Techne Corporation Brands" Retrieved on Jan. 19, 2022. Copyright 2022. Retrieved from: www.bio-techne.com/about/bio-techne-brands. 3 pages.
Traunecker et al., Janusin: new molecular design for bispecific reagents. Int J Cancer Suppl 7, 51-52 (1992).
Wang et al., "VSIG-3/IGSF11 is a Ligand of VISTA/PD-1H and Inhibits Human T Cell Function" Abstract 154.1, presented at American Association of Immunology Conference, Washington DC, May 14, 2017; Retrieved from the Internet, Sep. 2021: app.core-apps.com/aai2017/abstract/9a14bff0a8f35af893c384cf61639cf1. 1 page.
Wang et al., "VSIG-3/IGSF11 is a Ligand of VISTA/PD-1H and Inhibits Human T Cell Function" Poster presented at American Association of Immunology conference, Washington DC, May 14, 2017, 1 page.
Goh et al., "Impact of host cell line choice on glycan profile," Critical Reviews in Biotechnology, Vo. 38, No. 6, 2018, pp. 851-867.

Aalberse et al., IgG4 breaking the rules. Immunology 105, 9-19 (2002).
Ailan et al., Identification of target genes of transcription factor activator protein 2 gamma in breast cancer cells. BMC Cancer 9, 279 (2009).
Altschul et al., Basic local alignment search tool. J Mol Biol 215, 403-410 (1990).
Altschul et al., Gapped BLAST and PSI-BLAST: a new generation of protein database search programs. Nucleic Acids Res 25, 3389-3402 (1997).
Angal et al., A single amino acid substitution abolishes the heterogeneity of chimeric mouse/human (IgG4) antibody. Mol Immunol 30, 105-108 (1993).
Bork et al., The immunoglobulin fold. Structural classification, sequence patterns and common core. J Mol Biol 242, 309-320 (1994).
Bushell et al., Large-scale screening for novel low-affinity extracellular protein interactions. Genome Res 18, 622-630 (2008).
Chan et al., Therapeutic antibodies for autoimmunity and inflammation. Nat Rev Immunol 10, 301-316 (2010).
Chothia et al., Canonical structures for the hypervariable regions of immunoglobulins. J Mol Biol 196, 901-917 (1987).
Cox et al., A directory of human germ-line V kappa segments reveals a strong bias in their usage. Eur J Immunol 24, 827-836 (1994).
Eom et al., Melanophore migration and survival during zebrafish adult pigment stripe development require the immunoglobulin superfamily adhesion molecule Igsf11. PLoS Genet 8, e1002899 (2012).
Flies et al., Coinhibitory receptor PD-1H preferentially suppresses CD4(+) T cell-mediated immunity. J Clin Invest 124, 1966-1975 (2014).
Harvey et al., The Hippo pathway and human cancer. Nat Rev Cancer 13, 246-257 (2013).
Holliger et al., "Diabodies": small bivalent and bispecific antibody fragments. Proc Natl Acad Sci U S A 90, 6444-6448 (1993).
Nowak et al., Immunoregulatory functions of VISTA. Immunol Rev 276, 66-79 (2017).
Orlandi et al., Cloning immunoglobulin variable domains for expression by the polymerase chain reaction. Proc Natl Acad Sci U S A 86, 3833-3837 (1989).
Ozkan et al., An extracellular interactome of immunoglobulin and LRR proteins reveals receptor-ligand networks. Cell 154, 228-239 (2013).
Pan et al., IL-1H, an interleukin 1-related protein that binds IL-18 receptor/IL-1Rrp. Cytokine 13, 1-7 (2001).
Presta, Molecular engineering and design of therapeutic antibodies. Curr Opin Immunol 20, 460-470 (2008).
Prodeus et al., VISTA.COMP—an engineered checkpoint receptor agonist that potently suppresses T cell-mediated immune responses. JCI Insight 2, (2017).
Ramos et al., "Mechanisms of Resistance to Immune Checkpoint Antibodies", Handbook of Experimental Pharmacology, (2017).
Rubinstein et al., Functional classification of immune regulatory proteins. Structure 21, 766-776 (2013).
Santus et al., "Osmotic drug delivery: a review of the patent literature" J. Controlled Release, 35(2):1-21 (1995).
Shields et al., High resolution mapping of the binding site on human IgG1 for Fc gamma RI, Fc gamma RII, Fc gamma RIII, and FcRn and design of IgG1 variants with improved binding to the Fc gamma R. J Biol Chem 276, 6591-6604 (2001).
Singer et al., Optimal humanization of 1B4, an anti-CD18 murine monoclonal antibody, is achieved by correct choice of human V-region framework sequences. J Immunol 150, 2844-2857 (1993).
Smith et al., Phage Display. Chem Rev 97, 391-410 (1997).
Smith and Waterman (1981) Advances in Applied Mathematics 2:482-489.
Songsivilai et al., Bispecific antibody: a tool for diagnosis and treatment of disease. Clin Exp Immunol 79, 315-321 (1990).
Stavenhagen et al., Fc optimization of therapeutic antibodies enhances their ability to kill tumor cells in vitro and controls tumor expansion in vivo via low-affinity activating Fcgamma receptors. Cancer Res 67, 8882-8890 (2007).

(56) References Cited

OTHER PUBLICATIONS

Stengel et al., Structure of TIGIT immunoreceptor bound to poliovirus receptor reveals a cell-cell adhesion and signaling mechanism that requires cis-trans receptor clustering. *Proc Natl Acad Sci U S A* 109, 5399-5404 (2012).

\* cited by examiner

FIG. 8A

>VISTA(1-195)-COMP-AlkPhos-Flag/His

| Signal peptide | MGVPTALEAGSWRWGSLLFALFLAASLGPVAA |
|---|---|
| Protein ectodomain | FKVATPYSLYVCPEGQNVTLTCRLLGPVDKGHDVTFYKTWYRSSRGE VQTCSERRPIRNLTFQDLHLHHGGHQAANTSHDLAQRHGLESASDHH GNFSITMRNLTLLDSGLYCCLVVEIRHHHSEHRVHGAMELQVQTGKD APSNCVVYPSSSQESENITAA |
| TEV cleavage site | GSENLYFQG |
| Linker 1 | NSGGGSGGGTG |
| Rat cartilage outer matrix protein (COMP) helix | GGDLAPQMLRELQETNAALQDVRELLRHRVKEITFLKNTVMECDACG |
| Linker 2 | LDRNLPPLAPLGP |
| Alkaline Phosphatase | IIPVEEENPDFWNREAAEALGAAKKLQPAQTAAKNLIIFLGDGMGVS TVTAARILKGQKKDKLGPEIPLAMDRFPYVALSKTYNVDKHVPDSGA TATAYLCGVKGNFQTIGLSAAARFNQCNTTRGNEVISVMNRAKKAGK SVGVVTTTRVQHASPAGTYAHTVNRNWYSDADVPASARQEGCQDIAT QLISNMDIDVILGGGRKYMFRMGTPDPEYPDDYSQGGTRLDGKNLVQ EWLAKRQGARYVWNRTELMQASLDPSVTHLMGLFEPGDMKYEIHRDS TLDPSLMEMTEAALRLLSRNPRGFFLFVEGGRIDHGHHESRAYRALT ETIMFDDAIERAGQLTSEEDTLSLVTADHSHVFSFGGYPLRGSSIFG LAPGKARDRKAYTVLLYGNGPGYVLKDGARPDVTESESGSPEYRQQS AVPLDEETHAGEDVAVFARGPQAHLVHGVQEQTFIAHVMAFAACLEP YTACDLAPPAGTTD |
| Flag | DYKDDDDK |
| 6xHis | HHHHHH |

>VISTA(1-195)-COMP-His

| Signal peptide | MGVPTALEAGSWRWGSLLFALFLAASLGPVAA |
|---|---|
| Protein ectodomain | FKVATPYSLYVCPEGQNVTLTCRLLGPVDKGHDVTFYKTWYRSSRGE VQTCSERRPIRNLTFQDLHLHHGGHQAANTSHDLAQRHGLESASDHH GNFSITMRNLTLLDSGLYCCLVVEIRHHHSEHRVHGAMELQVQTGKD APSNCVVYPSSSQESENITAA |
| TEV cleavage site | GSENLYFQG |
| Linker 1 | NSGGGSGGGTG |
| Rat cartilage outer matrix protein (COMP) helix | GGDLAPQMLRELQETNAALQDVRELLRHRVKEITFLKNTVMECDACG |
| Linker 2 | LDRNLPPLAPLGP |
| 6xHis | HHHHHH |

FIG. 8B

>VSIG3(1-245)-COMP-AlkPhos-Flag/His

| Signal peptide | MTSQRSPLAPLLLLSLHGVAA |
|---|---|
| Protein ectodomain | SLEVSESPGSIQVARGQPAVLPCTFTTSAALINLNVIWMVTPLSNAN QPEQVILYQGGQMFDGAPRFHGRVGFTGTMPATNVSIFINNTQLSDT GTYQCLVNNLPDIGGRNIGVTGLTVLVPPSAPHCQIQGSQDIGSDVI LLCSSEEGIPRPTYLWEKLDNTLKLPPTATQDQVQGTVTIRNISALS SGLYQCVASNAIGTSTCLLDLQVISPQPRNIGLIA |
| TEV cleavage site | GSENLYFQG |
| Linker 1 | NSGGGSGGGTG |
| Rat cartilage outer matrix protein (COMP) helix | GGDLAPQMLRELQETNAALQDVRELLRHRVKEITFLKNTVMECDACG |
| Linker 2 | LDRNLPPLAPLGP |
| Alkaline Phosphatase | IIPVEEENPDFWNREAAEALGAAKKLQPAQTAAKNLIIFLGDGMGVS TVTAARILKGQKKDKLGPEIPLAMDRFPYVALSKTYNVDKHVPDSGA TATAYLCGVKGNFQTIGLSAAARFNQCNTTRGNEVISVMNRAKKAGK SVGVVTTTRVQHASPAGTYAHTVNRNWYSDADVPASARQEGCQDIAT QLISNMDIDVILGGGRKYMFRMGTPDPEYPDDYSQGGTRLDGKNLVQ EWLAKRQGARYVWNRTELMQASLDPSVTHLMGLFEPGDMKYEIHRDS TLDPSLMEMTEAALRLLSRNPRGFFLFVEGGRIDHGHHESRAYRALT ETIMFDDAIERAGQLTSEEDTLSLVTADHSHVFSFGGYPLRGSSIFG LAPGKARDRKAYTVLLYGNGPGYVLKDGARPDVTESESGSPEYRQQS AVPLDEETHAGEDVAVFARGPQAHLVHGVQEQTFIAHVMAFAACLEP YTACDLAPPAGTTD |
| Flag | DYKDDDDK |
| 6xHis | HHHHHH |

>VSIG3(1-245)-COMP-His

| Signal peptide | MTSQRSPLAPLLLLSLHGVAA |
|---|---|
| Protein ectodomain | SLEVSESPGSIQVARGQPAVLPCTFTTSAALINLNVIWMVTPLSNAN QPEQVILYQGGQMFDGAPRFHGRVGFTGTMPATNVSIFINNTQLSDT GTYQCLVNNLPDIGGRNIGVTGLTVLVPPSAPHCQIQGSQDIGSDVI LLCSSEEGIPRPTYLWEKLDNTLKLPPTATQDQVQGTVTIRNISALS SGLYQCVASNAIGTSTCLLDLQVISPQPRNIGLIA |
| TEV cleavage site | GSENLYFQG |
| Linker 1 | NSGGGSGGGTG |
| Rat cartilage outer matrix protein (COMP) helix | GGDLAPQMLRELQETNAALQDVRELLRHRVKEITFLKNTVMECDACG |
| Linker 2 | LDRNLPPLAPLGP |
| 6xHis | HHHHHH |

FIG. 8C

>VSIG8(1-263)-COMP-AlkPhos-Flag/His

| Signal peptide | MRVGGAFHLLLVCLSPALLSA |
|---|---|
| Protein ectodomain | VRINGDGQEVLYLAEGDNVRLGCPYVLDPEDYGPNGLDIEWMQVNSD PAHHRENVFLSYQDKRINHGSLPHLQQRVRFAASDPSQYDASINLMN LQVSDTATYECRVKKTTMATRKVIVTVQARPAVPMCWTEGHMTYGND VVLKCYASGGSQPLSYKWAKISGHHYPYRAGSYTSQHSYHSELSYQE SFHSSINQGLNNGDLVLKDISRADDGLYQCTVANNVGYSVCVVEVKV SDSRRIG |
| TEV cleavage site | GSENLYFQG |
| Linker 1 | NSGGGSGGGTG |
| Rat cartilage outer matrix protein (COMP) helix | GGDLAPQMLRELQETNAALQDVRELLRHRVKEITFLKNTVMECDACG |
| Linker 2 | LDRNLPPLAPLGP |
| Alkaline Phosphatase | IIPVEEENPDFWNREAAEALGAAKKLQPAQTAAKNLIIFLGDGMGVS TVTAARILKGQKKDKLGPEIPLAMDRFPYVALSKTYNVDKHVPDSGA TATAYLCGVKGNFQTIGLSAAARFNQCNTTRGNEVISVMNRAKKAGK SVGVVTTTRVQHASPAGTYAHTVNRNWYSDADVPASARQEGCQDIAT QLISNMDIDVILGGGRKYMFRMGTPDPEYPDDYSQGGTRLDGKNLVQ EWLAKRQGARYVWNRTELMQASLDPSVTHLMGLFEPGDMKYEIHRDS TLDPSLMEMTEAALRLLSRNPRGFFLFVEGGRIDHGHHESRAYRALT ETIMFDDAIERAGQLTSEEDTLSLVTADHSHVFSFGGYPLRGSSIFG LAPGKARDRKAYTVLLYGNGPGYVLKDGARPDVTESESGSPEYRQQS AVPLDEETHAGEDVAVFARGPQAHLVHGVQEQTFIAHVMAFAACLEP YTACDLAPPAGTTD |
| Flag | DYKDDDDK |
| 6xHis | HHHHHH |

>VSIG8(1-263)-COMP-His

| Signal peptide | MRVGGAFHLLLVCLSPALLSA |
|---|---|
| Protein ectodomain | VRINGDGQEVLYLAEGDNVRLGCPYVLDPEDYGPNGLDIEWMQVNSD PAHHRENVFLSYQDKRINHGSLPHLQQRVRFAASDPSQYDASINLMN LQVSDTATYECRVKKTTMATRKVIVTVQARPAVPMCWTEGHMTYGND VVLKCYASGGSQPLSYKWAKISGHHYPYRAGSYTSQHSYHSELSYQE SFHSSINQGLNNGDLVLKDISRADDGLYQCTVANNVGYSVCVVEVKV SDSRRIG |
| TEV cleavage site | GSENLYFQG |
| Linker 1 | NSGGGSGGGTG |
| Rat cartilage outer matrix protein (COMP) helix | GGDLAPQMLRELQETNAALQDVRELLRHRVKEITFLKNTVMECDACG |
| Linker 2 | LDRNLPPLAPLGP |
| 6xHis | HHHHHH |

COMPOUNDS THAT MODULATE THE INTERACTION OF VISTA AND VSIG3 AND METHODS OF MAKING AND USING

CONTINUING APPLICATION DATA

This application is the § 371 U.S. National Stage of International Application No. PCT/US2019/016301, filed Feb. 1, 2019, which claims the benefit of U.S. Provisional Application Ser. No. 62/625,594, filed Feb. 2, 2018, and U.S. Provisional Application Ser. No. 62/627,478, filed Feb. 7, 2018, the disclosures of each of which are incorporated by reference herein in their entireties.

SEQUENCE LISTING

This application contains a Sequence Listing electronically submitted to the United States Patent and Trademark Office as an ASCII text file entitled "0541_000007WO02_ST25.txt" having a size of 51.7 kilobytes and created on Feb. 13, 2023. Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein and does not go beyond the disclosure in the International Application as filed.

BACKGROUND

V-region Immunoglobulin-containing Suppressor of T cell Activation (referred to herein as "VISTA," and also known as V-domain Immunoglobulin Suppressor of T cell Activation, PD-1H, Gi24, Dies1, DD1α, or B7-H5) has been reported to be a receptor that mediates T cell suppression.

SUMMARY OF THE INVENTION

In one aspect, this disclosure describes a compound that modulates the interaction of VISTA and "V-Set and Immunoglobulin domain containing 3" (referred to herein as "VSIG3" or "VSIG-3," also known as IGSF11), and methods that include modulating the interaction of VISTA and VSIG3 by introducing a compound that modulates the interaction of VISTA and VSIG3. VSIG3 is an adhesion protein expressed on epithelial and endothelial cells, and is upregulated in colorectal, intestinal, and hepatocellular carcinomas (Watanabe et al. (2005) *Cancer Sci.* 96:498). In some embodiments, VSIG3 is a VISTA ligand. In some embodiments, VISTA is a VSIG3 ligand.

In some embodiments, the method includes agonizing or antagonizing the interaction of VISTA and VSIG3. In some embodiments, the method includes modulating the multimerization of VISTA or of VSIG3 or of both.

In some embodiments, the compound that modulates the interaction of VISTA and VSIG3 includes an antibody to VSIG3, a VSIG3 polypeptide, a VISTA polypeptide, or a coiled-coil domain of a cartilage oligomeric matrix protein (COMP), or a combination thereof.

In some embodiments, the compound abrogates at least one of VISTA signaling and VSIG3 signaling. In some embodiments, the compound may affect T cell proliferation and/or T cell signaling including, for example, CD3-induced effects.

In another aspect, this disclosure describes treating a subject with a therapeutically effective amount of the compound.

In a further aspect, this disclosure describes antibodies to VSIG3 including monoclonal antibodies.

In an additional aspect, this disclosure describes compositions that include anti-VSIG3 antibodies. In a further aspect, this disclosure describes compositions that include multimerized VSIG3, a multimerized VISTA, and a multimerized VSIG8.

In a further aspect, this disclosure describes polyclonal antibodies raised against the VSIG3 immunogens described in Table 3A.

The term "antibody" as used herein refers to a molecule that contains at least one antigen binding site that immunospecifically binds to a particular antigen target of interest. The term "antibody" thus includes but is not limited to a full length antibody and/or its variants, a fragment thereof, peptibodies and variants thereof, monoclonal antibodies (including full-length monoclonal antibodies), polyclonal antibodies, multispecific antibodies (for example, bispecific antibodies) formed from at least two intact antibodies, human antibodies, humanized antibodies, and antibody mimetics that mimic the structure and/or function of an antibody or a specified fragment or portion thereof, including single chain antibodies and fragments thereof. Binding of an antibody to a target can cause a variety of effects, such as but not limited to where such binding modulates, decreases, increases, antagonizes, agonizes, mitigates, alleviates, blocks, inhibits, abrogates and/or interferes with at least one target activity or binding, or with receptor activity or binding, in vitro, in situ, and/or in vivo. An antibody of the present disclosure thus encompasses antibody fragments capable of binding to a biological molecule (such as an antigen or receptor) or portions thereof, including but not limited to Fab, Fab' and F(ab')$_2$, pFc', Fd, a single domain antibody (sdAb), a variable fragment (Fv), a single-chain variable fragment (scFv) or a disulfide-linked Fv (sdFv); a diabody or a bivalent diabody; a linear antibody; a single-chain antibody molecule; and a multispecific antibody formed from antibody fragments. The antibody may be of any type (for example, IgG, IgE, IgM, IgD, IgA and IgY), class (for example, IgG1, IgG2, IgG3, IgG4, IgA1 and IgA2), or subclass.

The term "monoclonal antibody" as used herein refers to an antibody obtained from a population of substantially homogeneous antibodies, that is, the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which typically include different antibodies directed against different determinants (epitopes), each monoclonal antibody is directed against a single determinant on the antigen. The monoclonal antibodies may be synthesized by hybridoma cells uncontaminated by other immunoglobulin producing cells. Alternatively, the monoclonal antibody may be produced recombinantly including, for example, by cells stably or transiently transfected with the heavy and light chain genes encoding the monoclonal antibody.

The modifier "monoclonal" indicates the character of an antibody, as defined above, as being obtained from a substantially homogeneous population of antibodies and is not to be construed as requiring engineering of the antibody by any particular method. In some embodiments, the term "monoclonal" is used herein to refers to an antibody that is derived from a clonal population of cells, including any eukaryotic, prokaryotic, or phage clone, and not the method by which the antibody was engineered.

As used herein, "isolated" refers to material removed from its original environment (for example, the natural environment if it is naturally occurring), and thus is altered "by the hand of man" from its natural state.

As used herein, "room temperature" is 16° C. to 26° C. or, more preferably, 18° C. to 24° C. In some embodiments, "room temperature" is 20° C. to 22° C.

As used herein "sequence identity" between two polypeptides is determined by comparing the amino acid sequence of one polypeptide to the sequence of a second polypeptide. When discussed herein, whether any particular polypeptide is at least 40 percent (%), at least 45%, at least 50%, at least 55%, at least 60%, at least 65%, at least 70%, at least 75%, at least 80%, at least 85%, at least 90%, at least 95%, at least 96%, at least 97%, at least 98%, or at least 99% identical to another polypeptide may be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman (1981) Advances in Applied Mathematics 2:482-489, to find the best segment of homology between two sequences. When using BESTFIT or any other sequence alignment program to determine whether a particular sequence is, for example, 95% identical to a reference sequence according to the present invention, the parameters are set such that the percentage of identity is calculated over the full length of the reference polypeptide sequence and that gaps in homology of up to 5% of the total number of amino acids in the reference sequence are allowed.

"Binding affinity" or "affinity binding" refers to the strength of the sum total of noncovalent interactions between a single binding site of a molecule (for example, an antibody) and its binding partner (for example, an antigen or antigenic epitope). The affinity of a molecule X for its partner Y is represented by the dissociation constant ($K_D$), which can generally be determined by using methods known in the art, for example, using the BIACORE biosensor, commercially available from BIACORE (GE Healthcare Worldwide, Chicago, IL). In some embodiments, antibodies of the present disclosure may be described in terms of their binding affinity for VSIG3. In some embodiments, antibodies of the present disclosure include antibodies that interact with an antigen wherein the dissociation constant ($K_D$) is less than or equal to $5 \times 10^{-6}$ M, less than or equal to $1 \times 10^{-6}$ M, less than or equal to $5 \times 10^{-7}$ M, less than or equal to $1 \times 10^{-7}$ M, less than or equal to $5 \times 10^{-8}$ M, less than or equal to $1 \times 10^{-8}$ M, less than or equal to $5 \times 10^{-9}$ M, less than or equal to $1 \times 10^{-9}$ M, less than or equal to $5 \times 10^{-10}$ M, less than or equal to $1 \times 10^{-10}$ M, less than or equal to $5 \times 10^{-11}$ M, less than or equal to $1 \times 10^{-11}$ M, less than or equal to $5 \times 10^{-12}$ M, less than or equal to $1 \times 10^{-12}$ M, less than or equal to $5 \times 10^{-13}$ M, less than or equal to $1 \times 10^{-13}$ M, less than or equal to $5 \times 10^{-14}$ M, less than or equal to $1 \times 10^{-14}$ M, less than or equal to $5 \times 10^{-15}$ M, or less than or equal to $1 \times 10^{-15}$ M.

As used herein, the term "subject" includes, but is not limited to, humans and non-human vertebrates. In some embodiments, a subject is a mammal, particularly a human. A subject may be an individual. A subject may be an "individual," "patient," or "host." Non-human vertebrates include livestock animals, companion animals, and laboratory animals. Non-human subjects also include non-human primates as well as rodents, such as, but not limited to, a rat or a mouse. Non-human subjects also include, without limitation, chickens, horses, cows, pigs, goats, dogs, cats, guinea pigs, hamsters, mink, and rabbits.

As used herein "in vitro" is in cell culture and "in vivo" is within the body of a subject.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.). Where a range of values is "up to" or "at least" a particular value, that value is included within the range.

For any method disclosed herein that includes discrete steps, the steps may be conducted in any feasible order. And, as appropriate, any combination of two or more steps may be conducted simultaneously.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 8A shows sequences of VISTA-COMP constructs: VISTA(1-195)-COMP-AlkPhos-Flag/His (SEQ ID NO:7) and VISTA(1-195)-COMP-His (SEQ ID NO:8); FIG. 8B shows sequences of VSIG3-COMP constructs: VSIG3(1-245)-COMP-AlkPhos-Flag/His (SEQ ID NO:9) and VSIG3(1-245)-COMP-His (SEQ ID NO:10); and FIG. 8C shows sequences of VSIG8-COMP constructs: VSIG8(1-263)-COMP-AlkPhos-Flag/His (SEQ ID NO:11) and VSIG8(1-263)-COMP-His (SEQ ID NO:12).

FIG. 9A and FIG. 9C show schematics of the Biacore experiment, where VISTA (FIG. 9A) or VISTA-COMP (FIG. 9C) is captured on the surface of a CM5 chip (GE Healthcare) using an anti-poly His antibody. The analyte, VSIG3-Fc, is flowed over the captured VISTA at concentration ranging between 0.2 nM and 20 μM. FIG. 9B and FIG. 9D show resulting sensorgrams and kinetic fits using a 1:1 model for the monomeric VISTA-VSIG3-Fc interaction (FIG. 9B) and the multimeric VISTA-COMP-VSIG3-Fc interaction (FIG. 9D). For captured monomeric VISTA, the VSIG3-Fc analyte was tested in the range of 0.247 µM to 20 µM. For captured multimeric VISTA-COMP, the VSIG3-Fc analyte was tested in the range of 0.2 nM to 500 nM. The multimeric VISTA-COMP has a ~150-fold higher affinity for VSIG3-Fc, largely due to an increase in the off-rate.

FIG. 17A shows a VISTA-VSIG3 complex having a 4:2 molecular stoichiometry. FIG. 17B shows a VISTA-VSIG3 complex including a VSIG3-VSIG8 heterodimer. FIG. 17C shows the stoichiometry of a PVR-TIGIT complex. FIG. 17D shows the stoichiometry of a PDL1-PD1 or PDL2-PD1 complex.

DETAILED DESCRIPTION OF ILLUSTRATIVE EMBODIMENTS

Figure 1A:
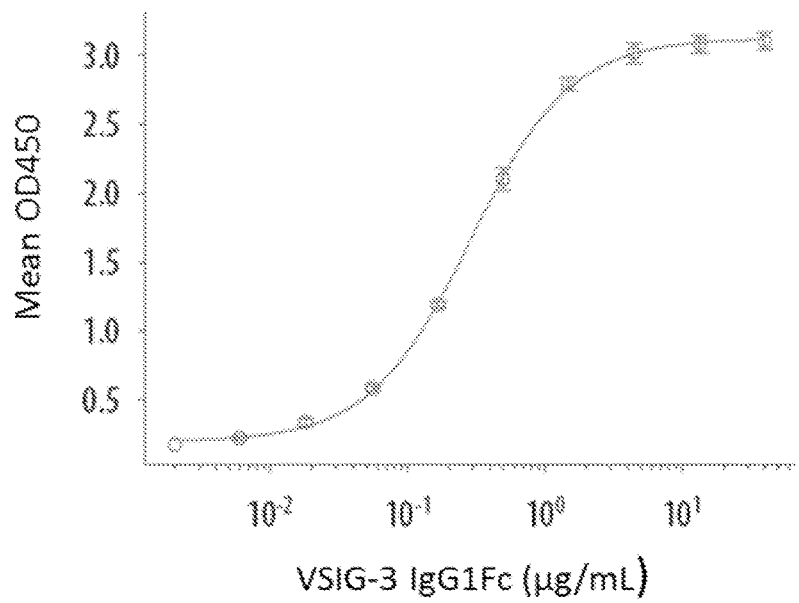
FIG. 1A shows a recombinant human VSIG3 Fc chimera ("rhVSIG3" or "VSIG03 IgG1 Fc") specifically binds to a recombinant human VISTA Fc chimera ("rhVISTA") in an exemplary functional enzyme-linked immunosorbent assay (ELISA) binding assay.

This disclosure describes compounds including antibodies and multimerized proteins capable of specifically binding "V-Set and Immunoglobulin domain containing 3" (referred to herein as "VSIG3" or "VSIG-3," also known as IGSF11); compounds capable of blocking interactions between VSIG3 and its binding partners including, for example, an interaction between VSIG3 and V-region Immunoglobulin-containing Suppressor of T cell Activation (referred to herein as "VISTA," and also known as V-domain Immunoglobulin Suppressor of T cell Activation, PD-1H, Gi24, Dies1, DD1α, or B7-H5); compositions including the compounds describes herein; and methods of making and using those compounds and compositions.

VISTA is a receptor that mediates T cell suppression. VSIG3, as a binding partner for VISTA, likely plays a role in maintaining T cell tolerance. Moreover, the interaction of VSIG3 with VISTA has a suppressive effect on T cell activation, T cell proliferation, and/or T cell cytokine or chemokine production. Therefore, compounds that abrogate a VSIG3-VISTA interaction may allow for altered immune regulation including, for example, an increased immune response.

As previously described in U.S. Provisional Application Ser. No. 62/370,395, filed Aug. 3, 2016, and PCT Application No. PCT/US2017/045314, each of which is incorporated by reference, and as further described herein, VSIG3 has been identified and characterized as a binding partner for VISTA. In some embodiments VSIG3 is a VISTA ligand. In some embodiments, VISTA is a VSIG3 ligand.

As further described herein and in in U.S. Provisional Application Ser. No. 62/370,395, filed Aug. 3, 2016, and PCT Application No. PCT/US2017/045314, blockade of the VSIG3/VISTA interaction with a neutralizing antibody or other compound may be effective in treating oncology and infectious disease and VSIG3/VISTA agonists which promote or enhance a VSIG3/VISTA interaction may be useful in the treatment of autoimmune, allergic, and inflammatory indications, GVHD, transplant or other indications wherein the suppression of T cell activation, T cell proliferation or cytokine production is desired.

Compounds that Modulate a VSIG3-VISTA Interaction and Methods of Using

In some aspects, this disclosure describes a compound that modulates the interaction of VISTA and VSIG3. In some embodiments, the compound may be used to modulate the interaction of VSIG3 and VISTA. In some embodiments, modulation of the interaction of VSIG3 and VISTA can include agonizing or antagonizing the interaction of VSIG3 and VISTA. In some embodiments, modulation of the interaction of VSIG3 and VISTA can include modulation of the multimerization of VSIG3. In some embodiments, modulation of the interaction of VSIG3 and VISTA can include modulation of the multimerization of VISTA. In some embodiments, modulation of the interaction of VSIG3 and VISTA can include abrogation of VISTA signaling or VSIG3 signaling or both. For example, modulation of the interaction may include enhancing or disrupting the downstream effects of VSIG3 or VISTA on at least one of cell proliferation, cytokine production, and chemokine production.

In some embodiments, the compound may include an anti-VSIG3 antibody including, for example, a monoclonal anti-VSIG3 antibody, as further described herein.

In some embodiments, the compound may include an anti-VISTA antibody.

In some embodiments, the compound may include a VSIG3 polypeptide, a VISTA polypeptide, a fusion protein, or a coiled-coil domain, or a combination thereof. In some embodiments, the compound may include an Fc domain.

In some embodiments, the compound may include a soluble fragment of VSIG3 and/or the extracellular region of VSIG3. In some embodiments, the compound may include a soluble fragment of VISTA and/or the extracellular region of VISTA. In some embodiments, the compound may include a protein encoded by at least one of the sequences of Table 1. In some embodiments, the compound may include a protein encoded having at least 80% sequence identity, at least 85% sequence identity, at least 90% sequence identity, at least 95% sequence identity, at least 98% sequence identity, or at least 99% sequence identity to at least one of the sequences of Table 1.

In some embodiments, the compound may include a multimerized VSIG3, a multimerized VISTA, or a multimerized VSIG8, or a combination thereof.

In some embodiments, the compound may affect T cell signaling including, for example, CD3-induced IL-2 production, CD3-induced interferon-γ production, CD3-induced RANTES production, CD3-induced MIP-1 alpha production, CD3-induced IL-17 production, and/or CD3-induced CXCL11 production. In some embodiments, the compound may affect T cell proliferation. Without wishing to be bound by theory, it is believed that VISTA and/or VSIG3 can abrogate these CD3-induced effects. Thus, in some embodiments, the compound can reverse that abrogation.

This disclosure further describes modulating the interaction of VISTA and VSIG3 by introducing a compound that modulates the interaction of VISTA and VSIG3. For example, a subject may be treated with a therapeutically effective amount of the compound. In some embodiments, VSIG3 may be overexpressed in a biological sample obtained from the subject.

Antibodies

In some embodiments, this disclosure describes an antibody that binds to VSIG3 (that is, an anti-VSIG3 antibody). In some embodiments, the antibody binds to human VSIG3 (hVSIG3).

In some embodiments, an antibody that binds to VSIG3 is a monoclonal antibody. In some embodiments, antibodies that bind to VSIG3 include monoclonal antibodies produced by the hybridoma cell lines (also referred to herein as clones) listed in Table 2A and/or by recombinant methods.

In some embodiments, an antibody that binds to VSIG3 is a polyclonal antibody. In some embodiments, the antibodies that bind to VSIG3 include polyclonal antibodies listed in Table 3A. In some embodiments, the antibodies that bind to VSIG3 include polyclonal antibodies raised using the peptide immunogens listed in Table 3A. In some embodiments the peptide immunogen comprises the sequence enumerated in Table 3A with a cysteine modification. In some embodiments the peptide immunogen comprises the sequence enumerated in Table 3A without a cysteine modification.

In some embodiments, the antibody is an isolated antibody. In some embodiments, the antibodies may be isolated or purified by conventional immunoglobulin purification procedures, such as protein A- or G-Sepharose, hydroxylapatite chromatography, gel electrophoresis, dialysis, or affinity chromatography.

In some embodiments, an antibody that binds to VSIG3 recognizes a VSIG3 polypeptide. In some embodiments, the VSIG3 polypeptide is human VSIG3 (SEQ ID NO:1; Uniprot number: Q5DX21; Gene ID: 152404) or a fragment thereof. In some embodiments, the VSIG3 polypeptide is mouse VSIG3 (Uniprot number: P0C673; Gene ID: 207683) or a fragment thereof. In some embodiments, an antibody that binds to VSIG3 recognizes a non-reduced VSIG3 polypeptide.

TABLE 1

| | | | | | | |
|---|---|---|---|---|---|---|
| Full length sequence | mtsqrsplap | llllslhgva | aslevsespg | siqvarggpa | vlpctfttsa | alinlnviwm 60 |
| for human (*homo sapiens*) | vtplsnanqp | eqvilyqggq | mfdgaprfhg | rvgftgtmpa | tnvsifinnt | qlsdtgtyqc 120 |
| VSIG 3 | lvnnlpdigg | rnigvtgltv | lvppsaphcq | iggsgdigsd | villcsseeg | iprptylwek 180 |
| (SEQ ID NO: 1) | ldntlklppt | atqdqvqgtv | tirnisalss | glyqcvasna | igtstclldl | qvispqprni 240 |
| | gliagaigtg | aviiifcial | ilgaffywrs | knkeeeeei | pneireddlp | pkcssakafh 300 |
| | teisssdnnt | ltssnaynsr | ywsnnpkvhr | ntesyshfsd | lggsfsfhsg | nanipsiyan 360 |
| | gthlvpgqhk | tlvvtanrgs | spqvmsrsng | svsrkprpph | thsytishat | lerigavpvm 420 |
| | vpagsragsl | v | | | | 431 |

TABLE 1-continued

| | | | | | | |
|---|---|---|---|---|---|---|
| Extracellular domain sequence listing for human (homo sapiens) VSIG3 (SEQ ID NO: 2) | mtsqrsplap vtplsnanqp lvnnlpdigg ldntlklppt gliag | llllslhgva eqvilyqggq rnigvtgltv atqdqvqgtv | aslevsespg mfdgaprfhg lvppsaphcq tirnisalss | siqvargqta rvgftgtmpa iggsgdigsd glyqcvasna 245 | vlpctfttsa tnvsifinnt villcsseeg igtstclldl | alinlnviwm qlsdtgtyqc iprptylwek qvispqprni | 60 120 180 240 |
| Extracellular domain sequence for human (homo sapiens) VISG3/Fc fusion protein (SEQ ID NO: 3) | levsespgsi dgaprfhgrv ppsaphcqiq rnisalssgl pcpapeaega ktkpreeqyn vytlppsrde skltvdksrw | qvargqtavl gftgtmpatn gsgdigsdvi yqcvasnaig psvflfppkp styrvvsvlt ltknqvsltc qqgnvfscsv | pctfttsaal vsifinntql llcsseegip tstclldlqv kdtlmisrtp vlhqdwlngk lvkgfypsdi mhealhnhyt | inlnviwmvt sdtgtyqclv rptylweklkd ispqprnigl evtcvvvdvs eykckvsnka avewesngqp qkslslspgk | plsnanqpeq nnlpdiggrn ntlklpptat iagiegrmdp hedpevkfnw lpapiektis ennykatppv | vilyqggqmf igvtgltvlv qdqvggtvti kscdkthtcp yvdgvevhna kakgqprepq ldsdgsffly 460 | 60 120 180 240 300 360 420 |
| Full length sequence for human (homo sapiens) VISTA (SEQ ID NO: 4) | mgvptaleag dkghdvtfyk sasdhhgnfs ypsssqdsen enpgfeaspp pvpdspnfev | swrwgsllfa twyrssrgev itmrnltlld itaaalatga aqgipeakvr i | lflaaslgpv qtcserrpir sglycclvve civgilclpl hplsyvagrq | aafkvatpys nltfqdlhlh irhhhsehrv illlvykqrq psesgrhlls 311 | lyvcpegqnv hgghqaants hgamelqvqt aasnrragel epstplsppg | tltcrllgpv hdlaqrhgle gkdapsncvv vrmdsniggi pgdvffpsld | 60 120 180 240 300 |
| Extracellular domain sequence for human (homo sapiens) VISTA (SEQ ID NO: 5) | mgvptaleag dkghdvtfyk sasdhhgnfs ypsssqesen | swrwgsllfa twyrssrgev itmrnltlld itaaiegr | lflaaslgpv qtcserrpir sglycclvve | aafkvatpys nltfqdlhlh irhhhsehrv 198 | lyvcpegqnv hgghqaants hgamelqvqt | tltcrllgpv hdlaqrhgle gkdapsncvv | 60 120 180 |
| Extracellular domain sequence for human (homo sapiens) VISTA/IgG Fc fusion protein (SEQ ID NO: 6) | fkvatpysly tfqdlhlhhg hhhsehrvhg cpapeagap tkpreeqyns ytlppsrdel kltvdksrwq | vcpegqnvtl ghqaantshd amelqvqtgk svflfppkpk tyrvvsvltv tknqvsltcl qgnvfscsvm | tcrllgpvdk laqrhglesa dapsncvvyp dtlmisrtpe lhqdwlngke vkgfypsdia healhnhytq | ghdvtfyktw sdhhgnfsit sssqesenit vtcvvvdvsh ykckvsnkal vewesngqpe kslslspgk | yrssrgevqt mrnltlldsg aaiegrmdpk edpevkfnwy papiektisk nnykatppvl | cserrpirnl lycclvveir scdkthtcpp vdgvevhnak akgqprepqv dsdgsfflys 399 | 60 120 180 240 300 360 |

In some embodiments, an antibody that binds to VSIG3 may include a derivative of an antibody that is modified or conjugated by the covalent attachment of any type of molecule to the antibody. Such antibody derivatives include, for example, antibodies that have been modified by glycosylation, acetylation, pegylation, phosphorylation, amidation, derivatization by known protecting/blocking groups, proteolytic cleavage, toxins, or linkage to a cellular ligand or other protein. Any of numerous chemical modifications may be carried out by known techniques, including, but not limited to, specific chemical cleavage, acetylation, formylation, and metabolic synthesis of tunicamycin. Additionally, the derivatives may contain one or more non-classical amino acids.

An antibody that binds to VSIG3 may be coupled directly or indirectly to a detectable marker by techniques well known in the art. A detectable marker is an agent detectable, for example, by spectroscopic, photochemical, biochemical, immunochemical, or chemical means. Useful detectable markers include, but are not limited to, fluorescent dyes, chemiluminescent compounds, radioisotopes, electron-dense reagents, enzymes, coenzymes, colored particles, biotin, or dioxigenin. A detectable marker often generates a measurable signal, such as radioactivity, fluorescent light, color, or enzyme activity. Antibodies conjugated to detectable agents may be used for diagnostic or therapeutic purposes. Examples of detectable agents include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or indirectly, through an intermediate such as, for example, a linker known in the art, using techniques known in the art. See, for example, U.S. Pat. No. 4,741,900, describing the conjugation of metal ions to antibodies for diagnostic use. Examples of suitable enzymes include horseradish peroxidase, alkaline phosphatase, beta-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; examples of bioluminescent materials include luciferin, and aequorin; and examples of suitable radioactive material include iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{113}$mIn, $^{115}$mIn), technetium ($^{99}$Tc, $^{99}$mTc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, and $^{97}$Ru. Techniques for conjugating such therapeutic moieties to antibodies are well-known.

Also included in the present disclosure are monoclonal antibodies produced by progeny or derivatives of these hybridoma cell lines, monoclonal antibodies produced by equivalent or similar hybridoma cell lines, and/or recombinant derivatives made thereof. In some embodiments, an antibody that binds to VSIG3 includes a recombinantly derived monoclonal antibody including, for example, a rabbit B cell derived monoclonal antibody.

An intact antibody molecule has two heavy (H) chain variable regions (abbreviated herein as $V_H$) and two light (L) chain variable regions (abbreviated herein as $V_L$). The $V_H$ and $V_L$ regions can be further subdivided into regions of hypervariability, termed "complementarity determining regions" ("CDRs"), interspersed with regions that are more conserved, termed "framework regions" ("FRs"). The extent of the FRs and CDRs has been precisely defined (see, Kabat et al. (1991) Sequences of Proteins of Immunological Interest, Fifth Edition, U.S. Department of Health and Human Services, NIH Publication No. 91-3242, and Chothia et al. (1987) *J. Mol. Biol.* 196: 901-917). Each $V_H$ and $V_L$ is composed of three CDRs and four FRs, arranged from amino-terminus to carboxy-terminus in the following order: FR1, CDR1, FR2, CDR2, FR3, CDR3, FR4.

In some embodiments, a monoclonal antibody includes a monoclonal antibody having the same heavy chain as a monoclonal antibody produced by at least one of the clones of Table 2A. In some embodiments, a monoclonal antibody includes a monoclonal antibody having the same light chain as a monoclonal antibody produced by at least one of the clones of Table 2A. In some embodiments, a monoclonal antibody includes a monoclonal antibody having the same heavy chain and the same light chain as a monoclonal antibody produced by at least one of the clones of Table 2A. In some embodiments, a monoclonal antibody can contain one, two, three, four, five, six, or more amino acid substitutions in the heavy and/or the light chains identified above wherein the amino acid substitutions do not substantially affect binding of the antibody to VSIG3.

In some embodiments, a monoclonal antibody includes a monoclonal antibody having the same $V_H$ domain as a monoclonal antibody produced by at least one of the clones of Table 2A. In some embodiments, a monoclonal antibody includes a monoclonal antibody having the same $V_L$ domain as a monoclonal antibody produced by at least one of the clones of Table 2A. In some embodiments, a monoclonal antibody includes a monoclonal antibody having the same $V_H$ domain and the same $V_L$ domain as a monoclonal antibody produced by at least one of the clones of Table 2A. In some embodiments, a monoclonal antibody can contain one, two, three, four, five, six, or more amino acid substitutions in the $V_H$ domains and/or the $V_L$ domains identified above which do not substantially affect binding of the antibody to VSIG3.

In some embodiments, a monoclonal antibody includes an antibody having the same $V_H$ domain as the monoclonal antibody produced by clone 774206 of Table 2A, wherein the $V_H$ domain is included in the following heavy chain sequence:

```
                                                      (SEQ ID NO: 15)
Met Asn Phe Gly Leu Ser Trp Ile Phe Leu Val Pro Val Leu Lys Gly

Val Leu Cys Glu Val Lys Leu Val Glu Ser Gly Arg Gly Leu Val Gln

Pro Gly Gly Ser Leu Lys Leu Ser Cys Ala Ala Ser Gly Phe Thr Phe

Ser Ser Tyr Ser Met Ser Trp Val Arg Gln Thr Pro Glu Lys Arg Leu

Glu Trp Val Ala Tyr Ile Ser Asn Gly Gly Gly Ser Thr Tyr Tyr Pro

Asp Thr Val Lys Gly Arg Phe Thr Ile Ser Arg Asp Asn Ala Lys Asn

Thr Leu Tyr Leu Gln Met Ser Ser Leu Lys Ser Glu Asp Thr Ala Met

Tyr Tyr Cys Ala Arg His Asp Gly Asn Tyr Pro Trp Phe Ala Tyr Trp

Gly Gln Gly Thr Leu Val Thr Val Ser Ala Ala Lys Thr Thr Pro Pro

Ser Val Tyr Pro Leu Ala Pro Gly Cys Gly Asp Thr Thr Gly Ser Ser

Val Thr Leu Gly Cys Leu Val Lys Gly Tyr Phe Pro Glu Ser Leu Glu

Pro Ser Gly Pro Ile Ser Thr Ile Asn Pro Cys Pro Cys Lys Glu

Cys His Lys Cys Pro Ala Pro Asn Leu Glu Gly Gly Pro Ser Val Phe

Ile Phe Pro Pro Asn Ile Lys Asp Val Leu Met Ile Ser Leu Thr Pro

Lys Val Thr Cys Val Val Val Asp Val Ser Glu Asp Asp Pro Asp Val

Gln Ile Ser Trp Phe Val Asn Asn Val Glu Val His Thr Ala Gln Thr

Gln Thr His Arg Glu Asp Tyr Asn Ser Thr Ile Arg Val Val Ser Thr

Leu Pro Ile Gln His Gln Asp Trp Met Ser Gly Lys Glu Phe Lys Cys

Lys Val Asn Asn Lys Asp Leu Pro Ser Pro Ile Glu Arg Thr Ile Ser

Lys Ile Lys Gly Leu Val Arg Ala Pro Gln Val Tyr Ile Leu Pro Pro

Pro Ala Glu Gln Leu Ser Arg Lys Asp Val Ser Leu Thr Cys Leu Val

Gly Phe Asn Pro Gly Asp Ile Ser Val Glu Trp Thr Ser Asn Gly

His Thr Glu Glu Asn Tyr Lys Asp Thr Ala Pro Val Leu Asp Ser Asp

Gly Ser Tyr Phe Ile Tyr Ser Lys Leu Asn Met Lys Thr Ser Lys Trp

Glu Lys Thr Asp Ser Phe Ser Cys Asn Val Arg His Glu Gly Leu Lys

Asn Tyr Tyr Leu Lys Xaa Thr Ile Ser Arg Ser Pro Gly Lys.
```

In some embodiments, a monoclonal antibody includes an antibody having the same $V_L$ domain as the monoclonal antibody produced by clone 774206 of Table 2A, wherein the $V_L$ domain is included in the following light chain sequence:

(SEQ ID NO: 16)
```
Met Asp Phe Gln Val Gln Ile Phe Ser Phe Leu Leu Ile Ser Ala Ser

Val Ile Met Ser Arg Gly Gln Ile Val Leu Ser Gln Ser Pro Ala Ile

Leu Ser Ala Ser Pro Gly Glu Lys Val Thr Met Thr Cys Arg Ala Ser

Ser Ser Val Ser Tyr Met His Trp Tyr Gln Gln Lys Pro Gly Ser Ser

Pro Lys Pro Trp Ile Tyr Ala Thr Ser Asn Leu Ala Ser Gly Val Pro

Ala Arg Phe Ser Gly Ser Gly Ser Gly Thr Ser Tyr Ser Leu Thr Ile

Ser Arg Val Glu Ala Glu Asp Ala Ala Thr Tyr Tyr Cys Gln Gln Trp

Ser Ser Asp Pro Pro Thr Phe Gly Arg Gly Thr Lys Leu Glu Ile Lys

Arg Ala Asp Ala Ala Pro Thr Val Ser Ile Phe Pro Pro Ser Ser Glu

Gln Leu Thr Ser Gly Gly Ala Ser Val Val Cys Phe Leu Asn Asn Phe

Tyr Pro Lys Asp Ile Asn Val Lys Trp Lys Ile Asp Gly Ser Glu Arg

Gln Asn Gly Val Leu Asn Ser Trp Thr Asp Gln Asp Ser Lys Asp Ser

Thr Tyr Ser Met Ser Ser Thr Leu Thr Leu Thr Lys Asp Glu Tyr Glu

Arg His Asn Ser Tyr Thr Cys Glu Ala Thr His Lys Thr Ser Thr Ser

Pro Ile Val Lys Ser Phe Asn Arg Asn Glu.
```

In some embodiments, a monoclonal antibody includes a monoclonal antibody having the same $V_H$ domain and the same $V_L$ domain as the monoclonal antibody produced by clone 774206 of Table 2A. In some embodiments, a monoclonal antibody can contain one, two, three, four, five, six, or more amino acid substitutions in the $V_H$ domains and/or the $V_L$ domains identified above which do not substantially affect binding of the antibody to VSIG3.

In some embodiments, a monoclonal antibody includes a monoclonal antibody having at least one CDR of the $V_H$ domain of a monoclonal antibody produced by at least one of the clones of Table 2A. In some embodiments, a monoclonal antibody includes a monoclonal antibody having at least two CDRs of the $V_H$ domain of a monoclonal antibody produced by at least one of the clones of Table 2A. In some embodiments, a monoclonal antibody includes a monoclonal antibody having at least three CDRs of the $V_H$ domain of a monoclonal antibody produced by at least one of the clones of Table 2A.

In some embodiments, a monoclonal antibody includes a monoclonal antibody having at least one CDR of the $V_H$ domain of the monoclonal antibody produced by clone 774306 of Table 2A, wherein the $V_H$ CDR1 is SYSMS (SEQ ID NO: 17), the $V_H$ CDR2 is YISNGGGSTYYPDTVKG (SEQ ID NO: 18), and the $V_H$ CDR3 is HDGNYPWFAY (SEQ ID NO: 19). In some embodiments, a monoclonal antibody includes a monoclonal antibody having at least two CDRs of the $V_H$ domain of the monoclonal antibody produced by clone 774206 of Table 2A. In some embodiments, a monoclonal antibody includes a monoclonal antibody having at least three CDRs of the $V_H$ domain of the monoclonal antibody produced by clone 774206 of Table 2A.

Additionally or alternatively, in some embodiments, a monoclonal antibody includes a monoclonal antibody having at least one CDR of the $V_L$ domain of a monoclonal antibody produced by at least one of the clones of Table 2A. In some embodiments, a monoclonal antibody includes a monoclonal antibody having at least two CDRs of the $V_L$ domain of a monoclonal antibody produced by at least one of the clones of Table 2A. In some embodiments, a monoclonal antibody includes a monoclonal antibody having at least three CDRs of the $V_L$ domain of a monoclonal antibody produced by at least one of the clones of Table 2A.

Additionally, or alternatively, in some embodiments, a monoclonal antibody includes a monoclonal antibody having at least one CDR of the $V_L$ domain of the monoclonal antibody produced by clone 774206 of Table 2A, wherein the $V_L$ CDR1 is RASSSVSYMH (SEQ ID NO: 20), the $V_L$ CDR2 is ATSNLAS (SEQ ID NO: 21), and the $V_L$ CDR3 is QQWSSDPPT (SEQ ID NO: 22). In some embodiments, a monoclonal antibody includes a monoclonal antibody having at least two CDRs of the $V_L$ domain of the monoclonal antibody produced by clone 774206 of Table 2A. In some embodiments, a monoclonal antibody includes a monoclonal antibody having at least three CDRs of the $V_L$ domain of the monoclonal antibody produced by clone 774206 of Table 2A.

In some embodiments, a monoclonal antibody can contain one, two, three, four, five, six, or more amino acid substitutions in one or more CDRs identified above which do not substantially affect binding of the antibody to VSIG3.

In some embodiments, a monoclonal antibody can contain one, two, three, four, five, six, or more amino acid substitutions in one or more framework regions (FRs). In some embodiments, the substitutions or substitutions in the framework regions (FRs) do not substantially affect binding of the antibody to VSIG3.

In some embodiments, a monoclonal antibody includes a monoclonal antibody having an amino acid sequence at least 70%, at least 80%, at least 85%, at least 90%, at least 95%, at least 96%, at least 97%, at least 98%, or at least 99% identical to an amino acid sequence of at least one CDR of a $V_H$ domain of an antibody produced by one of the clones of Table 2A.

In some embodiments, a monoclonal antibody includes a monoclonal antibody having an amino acid sequence at least 70%, at least 80%, at least 85%, at least 90%, at least 95%, at least 96%, at least 97%, at least 98%, or at least 99% identical to an amino acid sequence of at least two CDRs of a $V_H$ domain of an antibody produced by one of the clones of Table 2A.

In some embodiments, a monoclonal antibody includes a monoclonal antibody having an amino acid sequence at least 70%, at least 80%, at least 85%, at least 90%, at least 95%, at least 96%, at least 97%, at least 98%, or at least 99% identical to an amino acid sequence of at least three CDRs of a $V_H$ domain of an antibody produced by one of the clones of Table 2A.

In some embodiments, a monoclonal antibody includes a monoclonal antibody having an amino acid sequence at least 70%, at least 80%, at least 85%, at least 90%, at least 95%, at least 96%, at least 97%, at least 98%, or at least 99% identical to an amino acid sequence of at least one CDR of a $V_L$ domain of an antibody produced by one of the clones of Table 2A.

In some embodiments, a monoclonal antibody includes a monoclonal antibody having an amino acid sequence at least 70%, at least 80%, at least 85%, at least 90%, at least 95%, at least 96%, at least 97%, at least 98%, or at least 99% identical to an amino acid sequence of at least two CDRs of a $V_L$ domain of an antibody produced by one of the clones of Table 2A.

In some embodiments, a monoclonal antibody includes a monoclonal antibody having an amino acid sequence at least 70%, at least 80%, at least 85%, at least 90%, at least 95%, at least 96%, at least 97%, at least 98%, or at least 99% identical to an amino acid sequence of at least three CDRs of a Vi domain of an antibody produced by one of the clones of Table 2A.

In some embodiments, an anti-VSIG3 antibody includes an antibody that binds to the same VSIG3 epitope as an antibody produced by one of the clones of Table 2A.

In some embodiments, an antibody can contain one, two, three, four, five, six, or more amino acid substitutions relative to an antibody produced by one of the clones of Table 2A, wherein the substitutions do not substantially affect binding of the antibody to VSIG3 and/or the function of the antibody.

In some embodiments, an anti-VSIG3 antibody includes an antibody that interacts with an ABE Ig face of VSIG3 (FIG. 17-18). In some embodiments, an anti-VSIG3 antibody includes an antibody that interacts with an GFC Ig face of VSIG3 (FIG. 17-18).

The antibody may be an antibody from any suitable species. In some embodiments, the antibody may be a mouse antibody. In some embodiments, the antibody may be a rat antibody. In some embodiments, the antibody may be a rabbit antibody.

In some embodiments, the antibody is an IgG antibody. In some embodiments, the antibody may be an antibody or an IgG subclass including, for example, IgG1, IgG2, IgG3 or IgG4. In some embodiments, the antibody may be a mouse IgG of one of the following sub-classes: IgG1, IgG2A, IgG2B, IgG2C and IgG3. In some embodiments, the antibody may be a rat IgG of one of the following sub-classes: IgG1, IgG2A, IgG2B, or IgG2C.

In some embodiments, the antibody may include a kappa light chain. In some embodiments, the antibody may include a lambda light chain.

In some embodiments, the monoclonal antibody includes an antigen-binding fragment including an Fab fragment, an Fab' fragment, an F(ab)$_2$ fragment, and/or an Fv fragment.

A monoclonal antibody may be obtained by any suitable technique. In some embodiments, an antibody that binds to VSIG3 may be made by recombinant DNA methods, produced by phage display, and/or produced by combinatorial methods. DNA encoding an antibody that binds to VSIG3 may be readily isolated and sequenced using conventional procedures. In some embodiments, a hybridoma cell described herein may serve as a source of such DNA. Once isolated, the DNA may be transfected into a host cell (including, for example, simian COS cells, Chinese hamster ovary (CHO) cells, human embryonic kidney cells (HEK), or myeloma cells that do not otherwise produce immunoglobulin protein) or introduced into a host cell by genome editing (for example, using a CRISPR-Cas system) to obtain the synthesis of monoclonal antibodies in a recombinant host cells. The DNA encoding an antibody that binds to VSIG3 may be modified to, for example, humanize the antibody.

In some embodiments, the antibody may be a humanized antibody. An antibody that binds to VSIG3 may be humanized by any suitable method. Techniques for producing humanized monoclonal antibodies may be found, for example, in Jones et al. (1986) *Nature* 321:522 and Singer et al. (1993) *J. Immunol.* 150:2844. For example, humanization of the antibody may include changes to the antibody to reduce the immunogenicity of the antibody when used in humans. In some embodiments, a humanized antibody that binds to VSIG3 may include at least a portion of an immunoglobulin constant region (Fc) of a human immunoglobulin. A humanized antibody that binds to VSIG3 may include, in some embodiments, a human immunoglobulin (recipient antibody) in which residues from one or more complementary determining regions (CDRs) of the recipient antibody are replaced by residues from one or more CDRs of a non-human species antibody (donor antibody), such as mouse, rat, or rabbit antibody, that binds to VSIG3. In some embodiments, Fv framework residues of a human immunoglobulin may be replaced by corresponding non-human residues from an antibody that binds to VSIG3.

In some embodiments, a monoclonal antibody includes a chimeric antibody, that is, an antibody in which different portions are derived from different animal species. A chimeric antibody may be obtained by, for example, splicing the genes from a mouse antibody molecule with appropriate antigen specificity together with genes from a human antibody molecule of appropriate biological specificity. See, for example, Takeda et al. (1985) *Nature* 314:544.

In some embodiments, an antibody includes a bispecific or a bifunctional antibody. A bispecific or bifunctional antibody is an artificial hybrid antibody having two different heavy/light chain pairs and two different binding sites. A bispecific antibody may be produced by a variety of methods including fusion of hybridomas or linking of F(ab') fragments. See, for example, Songsivilai and Lachmann (1990) *Clin. Exp. Immunol.* 79:315; Kostelny et al. (1992) *J. Immunol.* 148:1547. In addition, bispecific antibodies may be formed as "diabodies" (Holliger et al. (1993) *PNAS USA* 90:6444) or "Janusins" (Traunecker et al. (1991) *EMBO J.* 10:3655; Traunecker et al. (1992) *Int. J. Cancer Suppl.* 7:51).

In some embodiments, an antibody is produced by an animal (including, but not limited to, human, mouse, rat, rabbit, hamster, goat, horse, chicken, or turkey), produced by a cell from an animal, chemically synthesized, or recombinantly expressed. The antibody may be purified by any method known in the art for purification of an immunoglobulin molecule, for example, by chromatography (for example, ion exchange, affinity, and sizing column chromatography), centrifugation, differential solubility, or by any other standard technique for the purification of proteins. In addition, an antibody may be fused to a heterologous polypeptide sequence, as described herein or otherwise known in the art, including, for example, to facilitate purification.

A monoclonal antibody may be assayed for immunospecific binding by the methods described herein and by any suitable method known in the art. The immunoassay that may be used includes but is not limited to a competitive and/or a non-competitive assay system using a technique such as BIACORE analysis, fluorescence activated cell sorter (FACS) analysis, immunofluorescence, immunocytochemistry, Western blot, radio-immunoassay, enzyme linked immunosorbent assay (ELISA), "sandwich" immunoassay, immunoprecipitation assay, precipitin reaction, gel diffusion precipitin reaction, immunodiffusion assay, agglutination assay, complement-fixation assay, immunoradiometric assay, fluorescent immunoassay, and protein A immunoassay. Such assays are routine and well known in the art (see for example, Ausubel et al., eds, Current Protocols in Molecular Biology, Vol. 1, John Wiley & Sons, Inc., N.Y. (1994)).

In some embodiments, an antibody that binds to VSIG3 includes an antibody that abrogates binding of VSIG3 to a VSIG3 ligand or a VSIG3 receptor. In some embodiments, the antibody includes an antibody that abrogates binding of VSIG3 to VISTA. In some embodiments the VISTA is human VISTA (SEQ ID NO:4; Uniprot number: Q9H7M9; Gene ID: 64115). In some embodiments, the antibody may decrease the binding of VSIG3 to a VSIG3 ligand (including, for example, VISTA) by at least 10 percent (%), at least 15%, at least 20%, at least 25%, at least 30%, at least 40%, at least 50%, at least 60%, at least 70%, at least 80%, at least 90%, at least 95%, or at least 98%.

In some embodiments, an antibody that binds to VSIG3 includes a monoclonal antibody produced by at least one of the hybridoma cell lines (also referred to as clones or antibody clones) of Table 2.

In some embodiments, an antibody that binds to VSIG3 may be made by immunizing an animal with the extracellular domain of VSIG3. In some embodiments, an antibody that binds to VSIG3 may be made by immunizing an animal with amino acids 1-245 of human VSIG3 (Uniprot number: Q5DX21; Gene ID: 152404). In some embodiments, the animal may be a mammal. For example, the animal may be a rabbit, a mouse, a goat, a sheet, a llama or a rat. In some embodiments, the animal may be a chicken.

In another aspect, this disclosure describes an isolated polynucleotide molecule. In some embodiments, the isolated polynucleotide molecule includes a nucleotide sequence encoding an antibody. In some embodiments, the isolated polynucleotide molecule includes a nucleotide sequence that has at least 75%, at least 80%, at least 85%, at least 90%, at least 95%, at least 96%, at least 97%, at least 98%, or at least 99% sequence identity to nucleotide sequence encoding an antibody described herein. In some embodiments, the isolated polynucleotide molecule includes polynucleotides that hybridize under high stringency to a nucleotide sequence encoding an antibody or a complement thereof. As used herein "stringent conditions" refer to the ability of a first polynucleotide molecule to hybridize, and remain bound to, a second, filter-bound polynucleotide molecule in 0.5 M NaHPO$_4$, 7% sodium dodecyl sulfate (SDS), and 1 mM EDTA at 65° C., followed by washing in 0.2×SSC/0.1% SDS at 42° C. (see Ausubel et al. (eds.), Current Protocols in Molecular Biology, Vol. 1, Green Publishing Associates, Inc., and John Wiley & Sons, Inc., N.Y. (1989), at p. 2.10.3). In some embodiments, the isolated polynucleotide molecule includes polynucleotides that encode one or more of the CDRs or the heavy and/or light chains of a monoclonal antibody of the present invention. General techniques for cloning and sequencing immunoglobulin variable domains and constant regions are well known. See, for example, Orlandi et al. (1989) *Proc. Nat'l Acad. Sci. USA* 86:3833.

In another aspect, this disclosure describes recombinant vectors including an isolated polynucleotide of the present invention. The vector may be, for example, in the form of a plasmid, a viral particle, or a phage. The appropriate DNA sequence may be inserted into a vector by a variety of procedures. In general, the DNA sequence is inserted into an appropriate restriction endonuclease site(s) in a vector by procedures known in the art. Such procedures are deemed to be within the scope of those skilled in the art. Large numbers of suitable vectors and promoters are known to those of skill in the art, and are commercially available. The following vectors are provided by way of example. Bacterial vectors include, for example, pQE70, pQE60, pQE-9, pBS, pD10, phagescript, psiX174, pbluescript SK, pbsks, pNH8A, pNH16a, pNH18A, pNH46A, ptrc99a, pKK223-3, pKK233-3, pDR540, and pRIT5. Eukaryotic vectors include, for example, pWLNEO, pSV2CAT, pOG44, pXT1, pSG, pSVK3, pBPV, pMSG, and pSVL. However, any other plasmid or vector may be used.

In a further aspect, this disclosure also includes a host cell containing at least one of the above-described vectors. The host cell may be a higher eukaryotic cell, such as a mammalian or insect cell, or a lower eukaryotic cell, such as a yeast cell. Or, the host cell may be a prokaryotic cell, such as a bacterial cell, or a plant cell. Introduction of a vector construct into the host cell may be effected by any suitable techniques, such as, for example, calcium phosphate transfection, DEAE-Dextran mediated transfection, or electroporation. (Davis et al., Basic Methods in Molecular Biology (1986)).

Antibodies of the present invention may be expressed in mammalian cells, yeast, bacteria, or other cells under the control of appropriate promoters. Cell-free translation systems may also be employed to produce such proteins using RNAs derived from the DNA constructs of the present invention. Appropriate cloning and expression vectors for use with prokaryotic and eukaryotic hosts are described by Sambrook et al., Molecular Cloning: A Laboratory Manual, Second Edition, Cold Spring Harbor, N.Y. (1989).

Also included in the present invention are phage display libraries expressing one or more hypervariable regions from an antibody of the present invention, and clones obtained from such a phage display library. A phage display library is used to produce antibody derived molecules. Gene segments encoding the antigen-binding variable domains of antibodies are fused to genes encoding the coat protein of a bacteriophage. Bacteriophage containing such gene fusions are used to infect bacteria, and the resulting phage particles have coats that express the antibody-fusion protein, with the antigen-binding domain displayed on the outside of the bacteriophage. Phage display libraries may be prepared, for example, using the PH.D.-7 Phage Display Peptide Library Kit (Catalog #E8100S) or the PH.D.-12 Phage Display Peptide Library Kit (Catalog #E8110S) available from New England Biolabs Inc., Ipswich, MA See, for example, Smith and Petrenko (1997) Chem Rev. 97:391-410.

Hybridoma Cell Lines

This disclosure further describes hybridoma cell lines (also referred to herein as "clones" or "antibody clones") expressing monoclonal antibodies including, for example, the hybridoma cell lines of Table 2A. In some embodiments, a monoclonal antibody produced by a hybridoma cell line binds to VSIG3. In some embodiments, a monoclonal antibody produced by a hybridoma cell line abrogates binding of VSIG3 to VISTA.

Hybridoma cell lines may be obtained by various techniques familiar to those skilled in the art. For example, cells from an animal immunized with a desired antigen are immortalized, commonly by fusion with a myeloma cell (see, for example, Kohler and Milstein (1976) *Eur. J. Immunol.* 6:511; J. Goding in "Monoclonal Antibodies: Principles and Practice," Academic Press, pp 59-103 (1986); and Harlow et al., Antibodies: A Laboratory Manual, page 726 (Cold Spring Harbor Pub. 1988). In some embodiments, the immunized animal is preferably a mammal. In some embodiments, the immunized animal is a rat including, for example, a Wistar rat, or a mouse including, for example, a BALB/C mouse. In some embodiments, the cells from the animal are spleen cells. In some embodiments, the cells from the animal are preferably lymphocytes. In some embodiments, the myeloma cell includes a P3X63Ag8.653 cell.

Other known methods of producing transformed B cell lines that produce monoclonal antibodies may also be used.

Recombinant Antibodies

This disclosure further describes recombinantly-derived monoclonal antibodies. Recombinantly derived monoclonal antibodies may include, for example, rabbit B cell derived monoclonal antibodies. Monoclonal antibodies of the present disclosure may be produced by any suitable recombinant technique including, for example, by phage display or by combinatorial methods. See, for example, U.S. Pat. No. 5,223,409; WO 92/18619; WO 91/17271; WO 92/20791; WO 92/15679; WO 93/01288; WO 92/01047; WO 92/09690; or WO 90/02809. Such methods may be used to generate human monoclonal antibodies.

Uses for the Anti-VSIG3 Antibodies

An antibody that binds to VSIG3, as described herein, may be used for any suitable application. For example, a monoclonal antibody may be used in both in vitro and in vivo diagnostic and therapeutic methods.

In some embodiments, an antibody may be used to determine a level of expression of VSIG3 protein in vitro or in vivo. In some embodiments, an antibody may be used to label a cell in vivo or in vitro. In some embodiments, an antibody may be used to determine a level of expression of VSIG3 protein in a patient sample. In some embodiments, a patient sample may include a mammalian cancer cell.

In some embodiments, the antibody may be labeled. For example, an antibody may be used to label a cell, and the labeled cell may be directly or indirectly imaged via secondary methods. In some embodiments, the cell is a mammalian cell.

In some embodiments, an antibody may be used to identify the presence or absence of VSIG3 protein in a sample from a subject. In some embodiments, identifying the presence of VSIG3 may include identifying an amount of VSIG3 in a sample from a subject.

In some embodiments, the antibody may be used to modulate the interaction of VSIG3 and VISTA. In some embodiments, modulation of the interaction of VSIG3 and VISTA can include agonizing or antagonizing the interaction of VSIG3 and VISTA. In some embodiments, modulation of the interaction of VSIG3 and VISTA can include modulation of the multimerization of VSIG3. In some embodiments, modulation of the interaction of VSIG3 and VISTA can include modulation of the multimerization of VISTA. In some embodiments, the antibody can agonize and/or antagonize the interaction of VSIG3 with VISTA. Such agonism and/or antagonism can produce immunotherapeutic effects.

In some embodiments, VSIG3 or VISTA or both may be expressed on the surface of a cell.

This disclosure further described a kit including an antibody. For example, a kit may include a composition that includes an anti-VSIG3 monoclonal antibody. The antibodies in the kit may be labeled with one or more detectable markers, as described herein.

A kit may include one or more containers filled with one or more of the monoclonal antibodies of the invention. Additionally, the kit may include other reagents such as buffers and solutions needed to practice the invention are also included. Optionally associated with such container(s) may be a notice or printed instructions. As used herein, the phrase "packaging material" refers to one or more physical structures used to house the contents of the kit. The packaging material is constructed by well-known methods, preferably to provide a sterile, contaminant-free environment. As used herein, the term "package" refers to a solid matrix or material such as glass, plastic, paper, foil, and the like, capable of holding within fixed limits a polypeptide.

Compositions Including Antibodies and/or Compounds that Modulate a VSIG3-VISTA Interaction In some embodiments, this disclosure describes a composition including at least one of the antibodies described herein and/or at least one of the compounds that modulate a VSIG3-VISTA interaction described herein.

In some embodiments, the composition may also include, for example, buffering agents to help to maintain the pH in an acceptable range or preservatives to retard microbial growth. A composition may also include, for example, carriers, excipients, stabilizers, chelators, salts, or antimicrobial agents. Acceptable carriers, excipients, stabilizers, chelators, salts, preservatives, buffering agents, or antimicrobial agents, include, but are not limited to, buffers such as phosphate, citrate, and other organic acids; antioxidants including ascorbic acid and methionine; preservatives, such as sodium azide, octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol; polypeptides; proteins, such as serum albumin, gelatin, or non-specific immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (for example, Zinc (Zn)-protein complexes); and/or non-ionic surfactants such as TWEEN, PLURONICS, or polyethylene glycol (PEG).

In some embodiments, the composition is a pharmaceutical composition and includes the monoclonal antibody and a pharmaceutically acceptable carrier, diluent or excipient. In the preparation of the pharmaceutical compositions comprising the antibodies described in the teachings herein, a variety of vehicles and excipients may be used, as will be apparent to the skilled artisan.

The pharmaceutical compositions will generally comprise a pharmaceutically acceptable carrier and a pharmacologically effective amount of an antibody, or mixture of antibodies.

The pharmaceutical composition may be formulated as a powder, a granule, a solution, a suspension, an aerosol, a solid, a pill, a tablet, a capsule, a gel, a topical cream, a suppository, a transdermal patch, and/or another formulation known in the art.

For the purposes described herein, pharmaceutically acceptable salts of an antibody are intended to include any art-recognized pharmaceutically acceptable salts including organic and inorganic acids and/or bases. Examples of salts include but are not limited to sodium, potassium, lithium, ammonium, calcium, as well as primary, secondary, and tertiary amines, esters of lower hydrocarbons, such as methyl, ethyl, and propyl. Other salts include but are not limited to organic acids, such as acetic acid, propionic acid, pyruvic acid, maleic acid, succinic acid, tartaric acid, citric acid, benzoic acid, cinnamic acid, salicylic acid, etc.

As used herein, "pharmaceutically acceptable carrier" comprises any standard pharmaceutically accepted carriers known to those of ordinary skill in the art in formulating pharmaceutical compositions. For example, the antibody may be prepared as a formulation in a pharmaceutically acceptable diluent, including for example, saline, phosphate buffer saline (PBS), aqueous ethanol, or solutions of glucose, mannitol, dextran, propylene glycol, oils (for example, vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or as a solid formulation in an appropriate excipient.

A pharmaceutical composition will often further comprise one or more buffers (for example, neutral buffered saline or phosphate buffered saline), carbohydrates (for example, glucose, sucrose or dextrans), mannitol, proteins, polypeptides or amino acids such as glycine, antioxidants (for example, ascorbic acid, sodium metabisulfite, butylated hydroxytoluene, butylated hydroxyanisole, etc.), bacteriostats, chelating agents such as EDTA or glutathione, adjuvants (for example, aluminium hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

Any suitable carrier known to those of ordinary skill in the art may be employed in a composition including at least one of the antibodies describes herein. Antibody compositions may be formulated for any appropriate manner of administration, including for example, oral, nasal, mucosal, intravenous, intraperitoneal, intradermal, subcutaneous, and intramuscular administration.

Administration and Treatment

The compositions of the present disclosure may be formulated in pharmaceutical preparations in a variety of forms adapted to the chosen route of administration. One of skill will understand that the composition will vary depending on mode of administration and dosage unit. For example, for parenteral administration, isotonic saline may be used. For topical administration a cream, including a carrier such as dimethylsulfoxide (DMSO), or other agents typically found in topical creams that do not block or inhibit activity of the peptide, may be used. Other suitable carriers include, but are not limited to alcohol, phosphate buffered saline, and other balanced salt solutions. The compounds of this invention may be administered in a variety of ways, including, but not limited to, intravenous, topical, oral, subcutaneous, intraperitoneal, and intramuscular delivery. In some aspects, the compounds of the present invention may be formulated for controlled or sustained release. In some aspects, a formulation for controlled or sustained release is suitable for subcutaneous implantation. In some aspects, a formulation for controlled or sustained release includes a patch. A compound may be formulated for enteral administration, for example, formulated as a capsule or tablet.

Administration may be as a single dose or in multiple doses. In some embodiments, the dose is an effective amount as determined by the standard methods, including, but not limited to, those described herein. Those skilled in the art of clinical trials will be able to optimize dosages of particular compounds through standard studies. Additionally, proper dosages of the compositions may be determined without undue experimentation using standard dose-response protocols. Administration includes, but is not limited to, any of the dosages and dosing schedules, dosing intervals, and/or dosing patterns described in the examples included herewith.

The composition including an antibody according to the present disclosure may be administered by any suitable means including, but not limited to, for example, oral, rectal, nasal, topical (including transdermal, aerosol, buccal and/or sublingual), vaginal, parenteral (including subcutaneous, intramuscular, and/or intravenous), intradermal, intravesical, intra-joint, intra-arteriole, intraventricular, intracranial, intraperitoneal, intranasal, by inhalation, or intralesional (for example, by injection into or around a tumor).

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that may be employed will be known to those of skill in the art. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the FDA. Such preparations may be pyrogen-free.

Many suitable formulations are known, including polymeric or protein microparticles encapsulating drug to be released, ointments, gels, or solutions which may be used topically or locally to administer drug, and even patches, which provide controlled release over a prolonged period of time. These may also take the form of implants. Such an implant may be implanted within the tumor.

The compounds of the present invention may also be provided in a lyophilized form. Such compositions may include a buffer, for example, bicarbonate, for reconstitution prior to administration, or the buffer may be included in the lyophilized composition for reconstitution with, for example, water. The lyophilized composition may further comprise a suitable vasoconstrictor, for example, epinephrine. The lyophilized composition may be provided in a syringe, optionally packaged in combination with the buffer for reconstitution, such that the reconstituted composition may be immediately administered to a patient.

As used herein "treating" or "treatment" may include therapeutic and/or prophylactic treatments. "Treating a disorder," as used herein, is not intended to be an absolute term.

Treatment may lead to an improved prognosis or a reduction in the frequency or severity of symptoms. A "therapeutically effective" concentration or amount as used herein is an amount that provides some improvement or benefit to the subject. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. Likewise, the term "preventing," as used herein, is not intended as an absolute term. Instead, prevention refers to delay of onset, reduced frequency of symptoms, or reduced severity of symptoms associated with a disorder. Prevention therefore refers to a broad range of prophylactic measures that will be understood by those in the art. In some circumstances, the frequency and severity of symptoms is reduced to non-pathological levels. In some circumstances, the symptoms of an individual receiving the compositions of the invention are only 90%, 80%, 70%, 60%, 50%, 40%, 30%, 20%, 10%, 5%, or 1% as frequent or severe as symptoms experienced by an untreated individual with the disorder.

Therapeutically effective concentrations and amounts may be determined for each application herein empirically by testing the compounds in known in vitro and in vivo systems, such as those described herein, dosages for humans or other animals may then be extrapolated therefrom.

It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

Toxicity and therapeutic efficacy of the compositions may be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and it may be expressed as the ratio between $LD_{50}$ and $ED_{50}$. Compositions that exhibit high therapeutic indices may be preferred. The data obtained from cell culture assays and animal studies may be used in formulating a range of dosage for use in humans. The dosage of such compositions may preferably lie within a range of circulating concentrations that include the $ED_{50}$ with little or no toxicity. The dosage may vary within this range depending upon the dosage form employed and the route of administration utilized. The exact formulation, route of administration and dosage may be chosen by the individual physician in view of the patient's condition.

A composition as described herein may be administered at once, or may be divided into a number of smaller doses to be administered at intervals of time. For example, compositions may be administered repeatedly, for example, at least 2, 3, 4, 5, 6, 7, 8, or more times, or may be administered by continuous infusion. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

In some therapeutic embodiments, an "effective amount" of an agent is an amount that results in a reduction of at least one pathological parameter. Thus, for example, in some aspects of the present disclosure, an effective amount is an amount that is effective to achieve a reduction of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% compared to the expected reduction in the parameter in an individual not treated with the agent.

In some aspects of the methods of the present disclosure, a method further includes the administration of one or more additional therapeutic agents. One or more additional therapeutic agents may be administered before, after, and/or coincident to the administration of a monoclonal antibody as described herein. An additional therapeutic agent may include, for example, chemotherapy, radiation therapy, etc. Additional therapeutic agents may be administered separately or as part of a mixture or cocktail. In some aspects of the present disclosure, the administration of an antibody may allow for the effectiveness of a lower dosage of other therapeutic modalities when compared to the administration of the other therapeutic modalities alone, providing relief from the toxicity observed with the administration of higher doses of the other modalities.

In some aspects of the methods of the present disclosure, the administration of a composition as described herein and the at least one additional therapeutic agent demonstrate therapeutic synergy. In some aspects of the methods of the present disclosure, a measurement of response to treatment observed after administering both an antibody as described herein and the additional therapeutic agent is improved over the same measurement of response to treatment observed after administering either the antibody or the additional therapeutic agent alone.

Identification and Methods of Using a VSIG3/VISTA Agonist and/or a VSIG3/VISTA Antagonist The interaction between VSIG3 and VISTA can be used to identify agonists or antagonists that agonize or antagonize binding of VISTA and VISIG and/or agonize or antagonize an effect of a VSIG3/VISTA interaction. In some embodiments, the VSIG3/VISTA interaction is a VSIG3/VISTA interaction on T cell immunity. In some embodiments, the VSIG3/VISTA interaction includes VISTA signaling. In certain cases, a VSIG3/VISTA antagonist will substantially inhibit or prevent the suppressive effects of VISTA on cell proliferation. In certain cases, a VSIG3 and/or VISTA antagonist will substantially inhibit or prevent the interaction of VSIG3 and VISTA. In certain cases, a VSIG3 and/or VISTA antagonist will result in inhibition of CD3-induced MIP-1 alpha, CD3-induced Rantes (CCL5), CD3-induced CXCL11, CD3-induced Interferon (IFN)-γ, IL-2 and/or IL-17 (also known as IL-17A) production. Such production may be decreased in peripheral blood mononuclear cells (PBMCs) and/or T cells. This inhibition may be detected using in vitro cell based assays with cells that express VISTA and/or VSIG3. Conversely, in certain cases, a VSIG3/VISTA agonist will substantially potentiate or enhance the suppressive effects of VISTA on immunity. This potentiation can also be detected using in vitro using cell based assays with cells that express VISTA and/or VSIG3.

In some embodiments, a VSIG3/VISTA agonist or a VSIG3/VISTA antagonist agonizes or antagonizes the interaction of VSIG3 and VISTA. In some embodiments, a VSIG3/VISTA agonist or a VSIG3/VISTA antagonist agonizes or antagonizes the interaction of VSIG3 and VISTA when at least one of VSIG3 and VISTA is expressed on the surface of a cell. In some embodiments, a VSIG3/VISTA agonist or a VSIG3/VISTA antagonist can agonize or antagonize the multimerization of VSIG3. The multimerization of VSIG3 may include homodimerization of VSIG3 and/or heterodimerization of VSIG3 including, for example, with VSIG8.

In some embodiments, an VSIG3/VISTA agonist or VSIG3/VISTA antagonist can include an antibody. In some embodiments, the VSIG3/VISTA agonist or VSIG3/VISTA antagonist includes an anti-VISTA antibody. In some embodiments, the VSIG3/VISTA agonist or VSIG3/VISTA antagonist includes an anti-VSIG3 antibody.

VSIG3/VISTA agonists and VSIG3/VISTA antagonists can be formulated for use in human therapy. For example, in some cases, a composition can be provided that includes a VSIG3/VISTA agonist or VSIG3/VISTA antagonist in combination with one or more suitable carriers, excipients, stabilizers, chelators, salts, or antimicrobial agents. In addition, the VSIG3/VISTA agonist or VSIG3/VISTA antagonist in the composition can be modified to enhance in vivo stability. For example, in some cases, the VSIG3/VISTA agonist or VSIG3/VISTA antagonist can be attached to one or more desired moieties such as one or more water-soluble polymers such as polyethylene glycol polymers. Also, in some cases, the composition can include more than one VSIG3/VISTA agonist or VSIG3/VISTA antagonist.

In some cases, compositions are provided containing a VSIG3/VISTA agonist to inhibit T cell immunity in conditions where this is therapeutically desirable, such as autoimmunity, allergy or inflammatory conditions. Such compositions can comprise an amount of a VSIG3/VISTA agonist effective to suppress T cell activation or proliferation in a subject in need thereof. Exemplary autoimmune, inflammatory and allergic conditions include but are not limited to arthritic conditions such as RA, psoriatic arthritis, scleroderma, multiple sclerosis, lupus, IBD, ITP, diabetes, sarcoidosis, allergic asthma, and the like.

In other cases, compositions are provided containing a VSIG3/VISTA antagonist to promote T cell immunity and to treat conditions where this is therapeutically desirable, such as cancer and infectious disease conditions. Such compositions can comprise an amount of an antagonist effective to promote T cell activation or proliferation in a subject in need thereof, e.g. a subject with a cancer.

The VSIG3/VISTA antagonist can be provided in compositions used to treat a cancer. The cancer can include but is not limited to melanoma, lymphoma, leukemia, lung cancer, ovarian cancer, cervical cancer, testicular cancer, digestive cancers, esophageal cancer, liver cancers, pancreatic cancer, kidney cancer and skin cancer. Applicant has also discovered that VSIG3 is highly expressed in colon cancer tissue and liver cancer tissue compared to healthy tissue. Thus, in some cases, a VSIG3/VISTA antagonist can be provided in compositions used to treat colon cancer. Also, in some cases, a VSIG3/VISTA antagonist can be provided in compositions used to treat liver cancer. In certain cases, a VSIG3/VISTA antagonist can be provided in compositions used to treat cancer by blocking interaction of VSIG3 and VISTA to prevent inhibition of MIP-1 alpha, Rantes (CCL5), CXCL11, and IL-17 secretion in PBMCs, which in turn allows for infiltration of T cells, monocytes, dendritic cells and macrophages into cancerous tissues.

Cancers include cancers that express or do not express VSIG3 and/or VISTA and further include non-metastatic or non-invasive as well as invasive or metastatic cancers wherein VSIG3 and/or VISTA expression by immune, stromal or diseased cells suppress antitumor responses and anti-invasive immune responses, and those characterized by vascularized tumors.

The VSIG3/VISTA antagonist can also be provided in compositions used to treat infectious diseases including but not limited to viral diseases such as HIV, HPV, EBV, encephalitis, herpes, other pox viruses, and other known human viruses, parasitic diseases, bacterial diseases, fungal or yeast associated diseases.

It should be understood that the disease conditions identified herein are intended to be exemplary and not exhaustive. In addition, the VSIG3/VISTA agonist or VSIG3/VISTA antagonist can be combined with other therapeutics which can be administered in the same or different compositions, at the same or different time. For example, the VSIG3/VISTA agonist or VSIG3/VISTA antagonist can be administered in a therapeutic regimen that includes the administration of a PD-1 or PD-L1 agonist or antagonist, CTLA4-Ig, a cytokine, a cytokine agonist or antagonist, or another receptor agonist or antagonist.

Multimerization

Without wishing to be bound by theory, it is believed that, in some embodiments, the VSIG3/VISTA interaction described herein may include a multimerized complex. For example, FIG. 17 shows a predicted, minimal VISTA-VSIG3 binding assembly that is consistent with a high-affinity interaction (~17 nM) as measured by Biacore shown in FIG. 9 and resembling the avidity-based extracellular interaction screen (AVEXIS) interaction assay shown in FIG. 7 and FIG. 10 with results in FIG. 11 to FIG. 14. This multimeric interaction further illustrates how the assembly of such a complex could be disrupted by the binding of anti-VSIG3 antibodies. The AVEXIS screen showed that a multimerized VISTA ectodomain (ECD) could bind a dimer of VSIG3 ECDs—but in the converse situation, pitting a penta-VSIG3 against a VISTA dimer, a binding event was not detected.

Without wishing to be bound by theory, these results are suggestive of a 4:2 stoichiometry between VISTA and VSIG3 molecules, wherein four VISTA ECDs engage two VSIG3 ECDs. This interaction is reminiscent of the binding complex captured by X-ray crystallography of the PVR-TIGIT structure (Stengel et al. (2012) *Proc. Natl. Acad. Sci. USA* 109:5399-5404) which shows a 2:2 stoichiometry of stably bound PVR and TIGIT ECDs, as shown in FIG. 17C. The PVR-TIGIT complex illustrates that the immunoglobulin (Ig) domains of TIGIT first need to associate as a homodimer in a back-to-back fashion, employing the 'ABE' or back face of the Ig domain β-sandwich (that is typically comprised of seven to nine β-strands, labeled A-G) (Bork et al. (1994) *J. Molec. Biol.* 242:309-320). The TIGIT ECD homodimer can then bind a pair of PVR ECDs, via respective front-to-front or 'GFC' face interactions. These GFC face-mediated Ig domain interactions are the most common way for Ig domains to bind, and have been captured by X-ray crystallography, in nearly every minimal binding complex between cell surface immunoregulatory receptors (Stengel et al. (2012) *Proc. Natl. Acad. Sci. USA* 109:5399-5404), and even antibodies and T-cell receptor (TCR) complexes (Lin et al. (2008) *Proc. Natl. Acad. Sci. USA* 105:3011-3016).

Figure 17A:
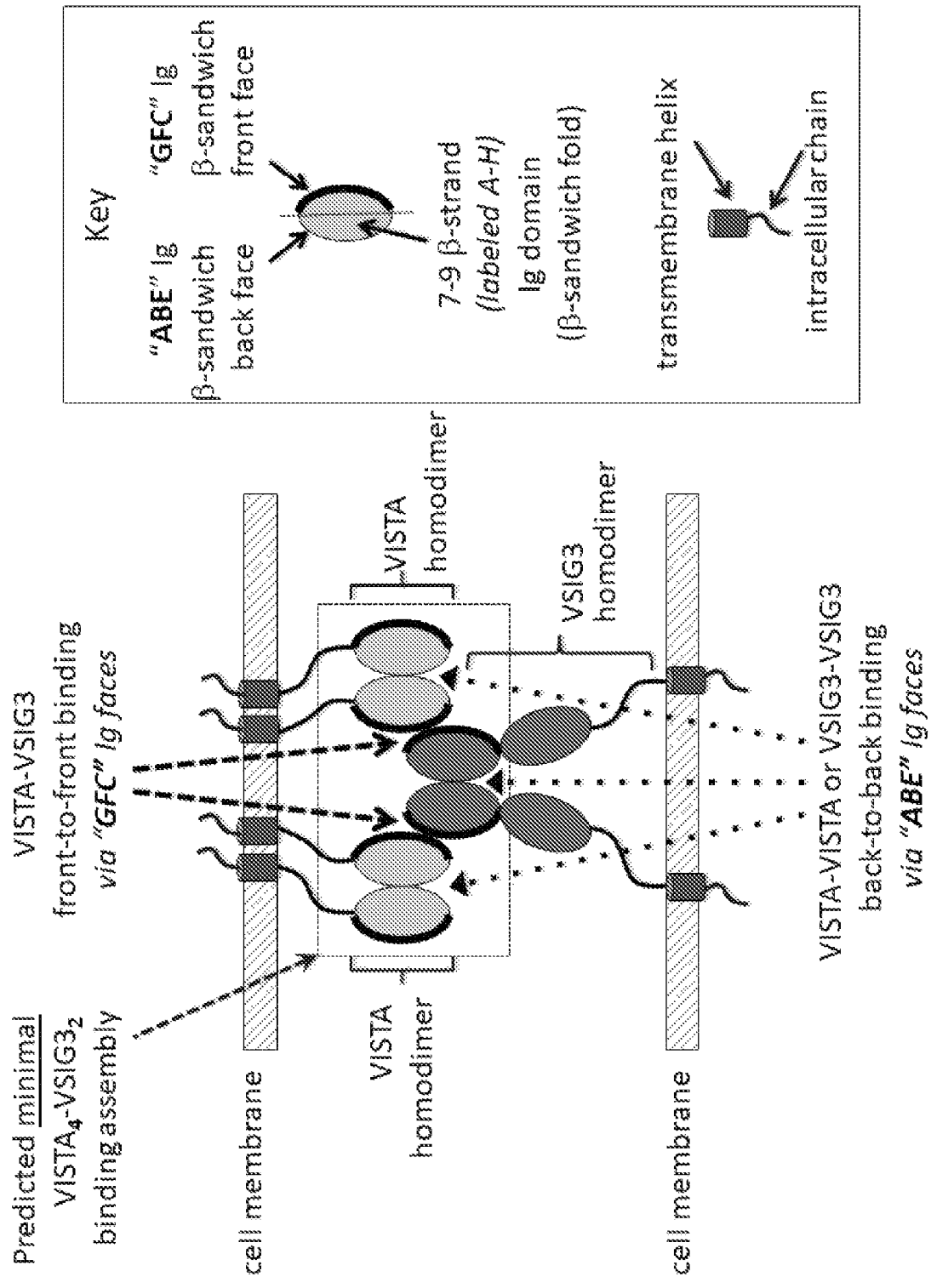
FIG. 17A-FIG. 17D show exemplary schematic models of VSIG3-VISTA interactions and complexes of related compounds.
Figure 17B:
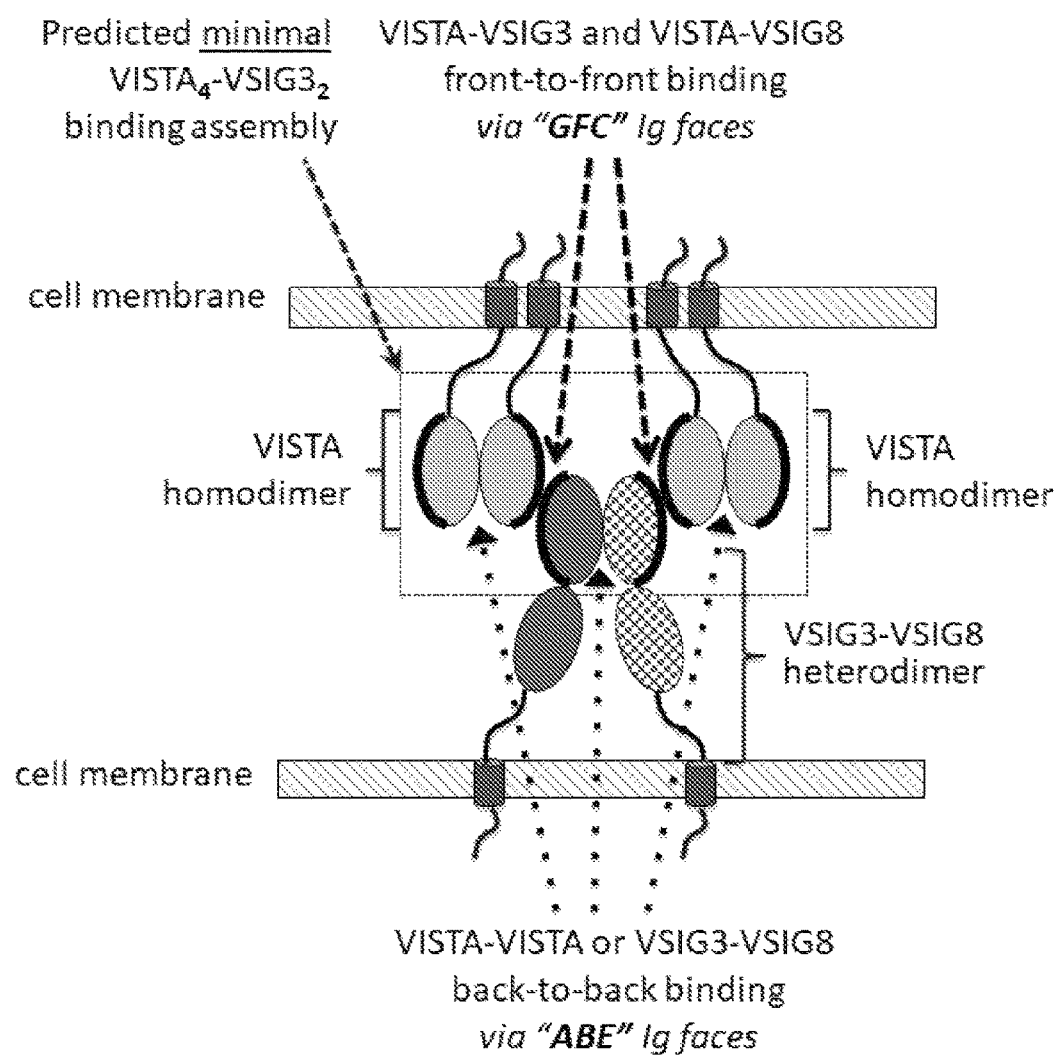
Figure 17C:
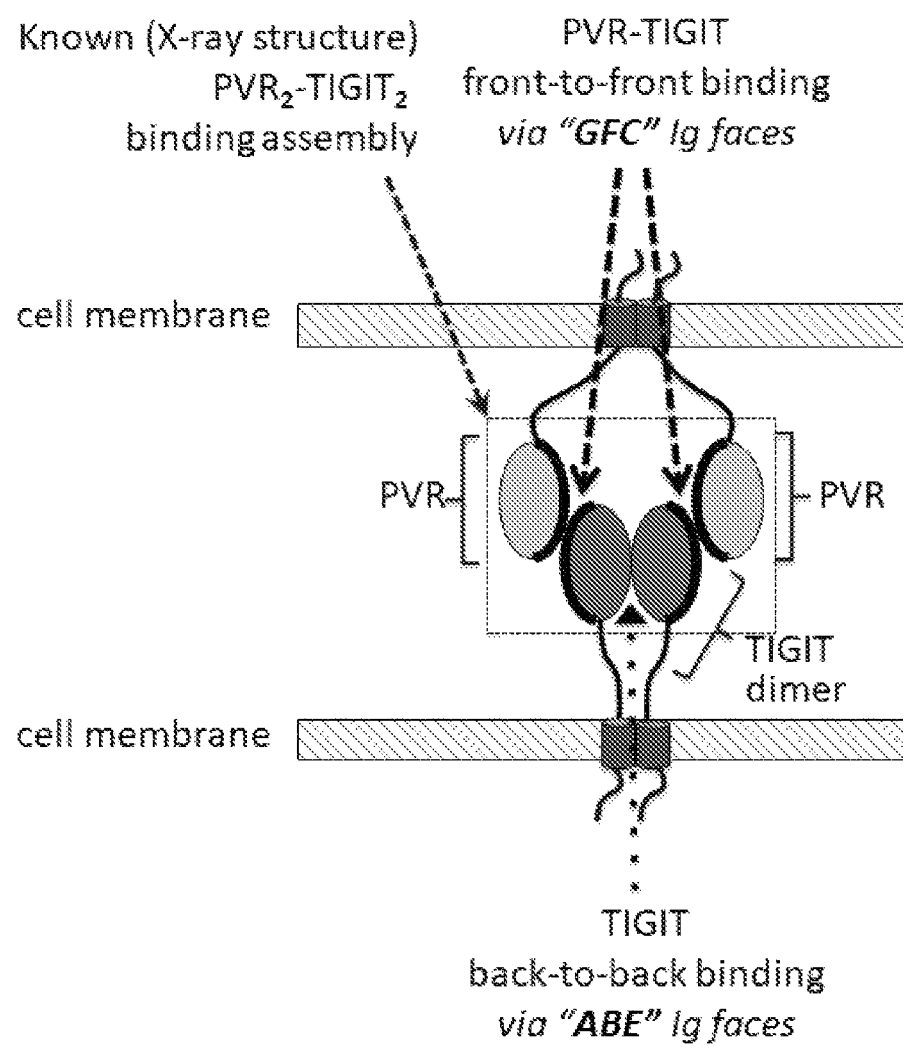
Figure 17D:
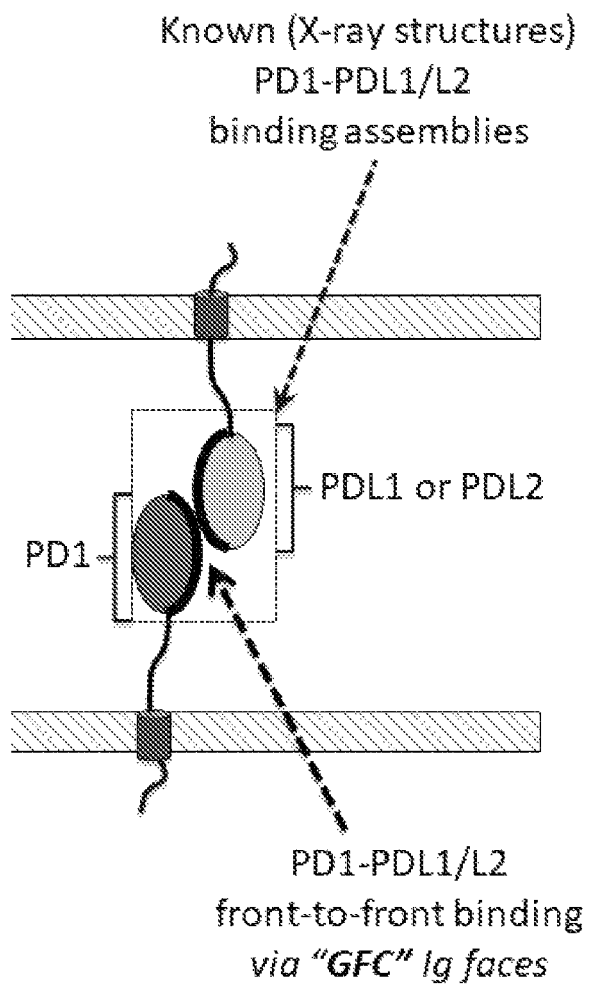

Similarly, FIG. 17D shows the 1:1 binding complex between PD-1 and both of its ligands, PD-L1 and PD-L2, that respectively utilize the same front-to-front (or GFC) faces of interacting Ig ECDs (Lin et al. (2008) Proc. Natl. Acad. Sci. USA 105:3011-3016; Lazar-Molnar et al. (2008) Proc. Natl. Acad. Sci. USA 105:10483-10488).

By analogy, VSIG3 may first form a back-to-back (ABE face) homodimer, as shown in FIG. 17A, or possibly a VSIG3-VSIG8 heterodimer, as shown in FIG. 17B (when both are present on the same cell surface). VSIG3 and VSIG8 are Ig superfamily proteins with very similar architectures (both of their respective ECDs reveal a pair of Ig domains, where only their N-terminal domains are predicted to be involved in intercellular binding to the VISTA ECD), and both cluster close together in the same Ig subfamily, drawing from a sensitive sequence-based classification of Ig immuoregulatory proteins (Rubinstein et al. (2013) *Structure* 21(5):766-776). This close sequence and structural relationship between VSIG3 and VSIG8 could allow their heterodimer formation and joint VISTA binding. As seen with PVR-TIGIT, the central VSIG3 homodimer engages VISTA ECDs through a front-to-front (or GFC face) interaction, shown in FIG. 17A and FIG. 17B. Differently from PVR-TIGIT, however, VISTA does not appear to engage VSIG3 as a monomer, but perhaps due to its unusual, nearly 20 amino acid insert in the middle of its Ig domain (which could destablize the folding of the VISTA Ig β-sandwich) (Nowak et al. (2017) *Immunol. Rev.* 276:66-79), needs to itself be stabilized via a back-to-back VISTA homodimer—and therefore four VISTA ECDs (in two pairs of back-to-back homodimers) are minimally used to grasp the VSIG3 homodimer (or VSIG3-VSIG8 heterodimer) in respective front-to-front interactions, as shown in FIG. 17A and FIG. 17B. By contrast, as shown in FIG. 17C, PVR is stable as a monomer ECD with a conventional Ig structure, and therefore only two PVRs are needed to engage the TIGIT homodimer.

Thus, as further described herein, blocking antibodies directed against VSIG3 may, in some embodiments disrupt the assembly of a 4:2 VISTA-VSIG3 complex (or VISTA4-VSIG32, as shown in FIG. 17A).

Multimerized VSIG3 or Multimerized VISTA and Methods of Making and Using

In some embodiments, this disclosure describes a multimerized VSIG3, a multimerized VISTA, and a multimerized VSIG8; methods of making multimerized VSIG3, multimerized VISTA, and multimerized VSIG8; and methods of using multimerized VSIG3, multimerized VISTA, and multimerized VSIG8.

In some embodiments, multimerized VSIG3, multimerized VISTA, and/or multimerized VSIG8 may include a coiled-coil domain. In some embodiments, the coiled-coil domain may be a pentameric coiled-coil domain. In some embodiments, the coiled-coil domain may be covalently linked to VSIG3, VISTA, or VSIG8. In some embodiments, the coiled-coil domain may be the coiled-coil domain of a cartilage oligomeric matrix protein (COMP). In some embodiments, the COMP protein may be a human protein. In some embodiments, the COMP protein may be a rat protein.

In some embodiments, the multimerized VSIG3, multimerized VISTA, and/or multimerized VSIG8 may include a linker domain. In some embodiments, the linker domain may be at least 10 amino acids, at least 11 amino acids, at least 12 amino acids, or at least 13 amino acids. In some embodiments, the linker domain may be up to 12 amino acids, up to 13 amino acids, up to 14 amino acids, up to 15 amino acids, or up to 20 amino acids. In some embodiments, the linker domain may include NSGGGSGGGTG (SEQ ID NO:13) or LDRNLPPLAPLGP (SEQ ID NO:14) or both.

In some embodiments, multimerized VSIG3, multimerized VISTA, and/or multimerized VSIG8 may include an alkaline phosphatase. The alkaline phosphatase may be used for enzymatic detection in an avidity-based extracellular interaction screen (AVEXIS) assay.

In some embodiments, multimerized VSIG3, multimerized VISTA, and/or multimerized VSIG8 may include a protein tag including, for example, a His tag.

In some embodiments, multimerized VSIG3, multimerized VISTA, and/or multimerized VSIG8 may include a TEV cleavage site. In some embodiments, a TEV cleavage site may include GSENLYFQG.

In some embodiments, multimerized VSIG3, multimerized VISTA, and/or multimerized VSIG8 may include all or a portion of each of the sequences disclosed in FIG. 8.

Without wishing to be bound by theory, the interactions between VSIG3 and VISTA and VSIG8 and VISTA are believed to exhibit a complex stoichiometry greater than the 1:1 interaction typically observed in receptor-ligand interactions (e.g., the interaction between PD-1 and PD-L1). For example, the interaction between VSIG3 and VISTA may have a 4:2 stoichiometry. Thus, the multimerization of VISTA, VSIG3, and VSIG8 can be useful to replicate, disrupt, or improve the detection the interaction between VSIG3 and VISTA or between VSIG8 and VISTA.

In some embodiments, a multimerized protein (e.g., multimerized VSIG3, multimerized VISTA, and/or multimerized VSIG8) may be used to modulate the interaction of VSIG3 and VISTA or VSIG8 and VISTA. In some embodiments, modulation of the interaction of VSIG3 and VISTA can include agonizing or antagonizing the interaction of VSIG3 and VISTA. In some embodiments, modulation of the interaction of VSIG8 and VISTA can include agonizing or antagonizing the interaction of VSIG8 and VISTA. In some embodiments, modulation of the interaction of VSIG3 and VISTA can include modulation of the multimerization of VSIG3. In some embodiments, modulation of the interaction of VSIG3 and VISTA can include modulation of the multimerization of VISTA. In some embodiments, modulation of the interaction of VSIG8 and VISTA can include modulation of the multimerization of VISTA. In some embodiments, modulation of the interaction of VSIG8 and VISTA can include modulation of the multimerization of VSIG8.

In some embodiments, multimerized VSIG3, multimerized VISTA, and/or multimerized VSIG8 may be used in a screening assay in vitro or in vivo. For example, multimerized VSIG3, multimerized VISTA, and/or multimerized VSIG8 may be used to screen for binding partners of VSIG3, VISTA, and/or VSIG8. Additionally or alternatively, multimerized VSIG3, multimerized VISTA, and/or multimerized VSIG8 may be used to screen for compounds that modulate the interaction of VSIG3 and VISTA; to screen for compounds that modulate the interaction of VSIG8 and VISTA; to screen for compounds that modulate the interaction of VSIG3 with a ligand of VSIG3; or to screen for compounds that modulate the interaction of VISTA with a ligand of VISTA. In some embodiments, multimerized VSIG3, multimerized VISTA, and/or multimerized VSIG8 may be used to measure the binding affinity and kinetics of a VISTA/VSIG interaction. In some embodiments, the multimer can be used in the development and/or characterization of VSIG3 agonists and/or VSIG3 antagonists. In some embodiments, using multimerized VSIG3, multimerized VISTA, and/or multimerized VSIG8 can increase detection sensitivity in a screening assay relative to a screening assay using non-multimerized proteins.

In some embodiments, multimerized VSIG3, multimerized VISTA, and/or multimerized VSIG8 may be used to modulate VSIG3, VSIG8, and/or VISTA signaling. For example, a VSIG3 multimerized VSIG3, multimerized VISTA, and/or multimerized VSIG8 may be used to inhibit or prevent the suppressive effects of VSIG3, VSIG8, or VISTA on T cells including, for example, on T cell signaling or on T cell proliferation. Additionally or alternatively, multimerized VSIG3, multimerized VISTA, and/or multimerized VSIG8 may be used to inhibit or prevent the interaction of VSIG3 and VISTA.

Figure 15:
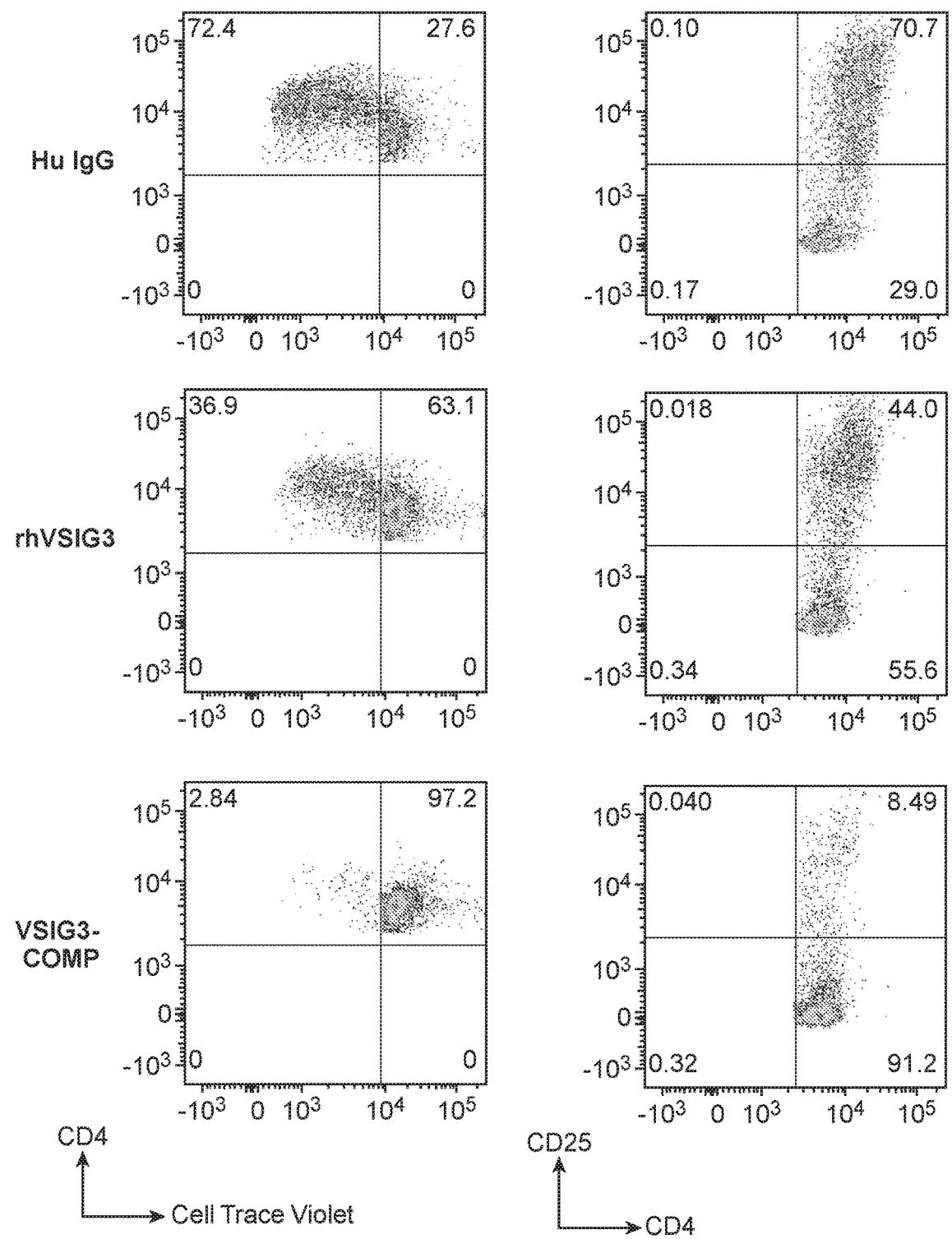
FIG. 15 shows VSIG3 COMP blocks T cell proliferation and activation. rhVSIG3 can partially inhibit anti-CD3-induced CD25 upregulation and proliferation of normal human peripheral blood T cells, while VSIG3-COMP can completely inhibit anti-CD3-induced CD25 expression and proliferation.

In certain cases, a VSIG3-COMP and/or VISTA-COMP antagonist will result in inhibition of CD3-induced signaling including, for example, CD3-induced MIP-1 alpha, CD3-induced Rantes (CCL5), CD3-induced CXCL11, CD3-induced Interferon (IFN)-γ, IL-2 and/or IL-17 (also known as IL-17A) production. Such CD3-induced signaling may be decreased in peripheral blood mononuclear cells (PBMCs) and/or T cells. This inhibition may be detected using in vitro cell-based assays with cells that express VISTA, VSIG3 and/or VSIG8. For example, as shown in FIG. 15, VSIG3-COMP blocks T cell proliferation and activation.

Method Embodiments

1. A method comprising modulating the interaction of VISTA and VSIG3, the method comprising introducing a compound that modulates the interaction of VISTA and VSIG3.
2. The method of embodiment 1, wherein the modulation of the interaction of VISTA and VSIG3 comprises agonizing or antagonizing the interaction of VISTA and VSIG3.
3. The method of either of embodiments 1 or 2, wherein modulating the interaction of VISTA and VSIG3 comprises modulating the multimerization of VISTA or VSIG3 or both.
4. The method of any one of embodiments 1 to 3, wherein
    VISTA is expressed on the surface of a cell,
    VSIG3 is expressed on the surface of a cell, or
    both VISTA and VISG3 are expressed on the surface of a cell.
5. The method of any one of embodiments 1 to 4, wherein the compound comprises an anti-VSIG3 antibody.
6. The method of embodiment 5, the anti-VSIG3 antibody comprising
    an antibody that binds to the same VSIG3 epitope as an antibody produced by one of the clones of Table 2A; or
    an antibody produced by one of the clones of Table 2A.
7. The method of either of embodiments 5 or 6, wherein an anti-VSIG3 antibody comprises
    at least one of
        a heavy chain variable region of an antibody produced by one or more of the clones of Table 2A; or
        a light chain variable region of an antibody produced by one or more of the clones of Table 2A.
8. The method of any one of embodiments 5 to 7, wherein an anti-VSIG3 antibody comprises
    at least one of
        a heavy chain variable region comprising one or more complementary determining regions (CDRs) of the heavy chain variable regions of an antibody produced by one of the clones of Table 2A; or
        a light chain variable region comprising one or more CDRs of the light chain variable regions of an antibody produced by one of the clones of Table 2A.
9. The method of any one of embodiments 5 to 8, wherein the anti-VSIG3 antibody comprises an antibody produced by one or more of the clones of Table 2A.
10. The method of any one of embodiments 5 to 9, the compound further comprising an anti-VISTA antibody.
11. The method of any one of embodiments 5 to 10, wherein the compound comprises an antigen-binding fragment.
12. The method of any one of embodiments 1 to 11, wherein the compound comprises a VSIG3 polypeptide.
13. The method of any one of embodiments 1 to 12, wherein the compound comprises a protein having at least 80% sequence identity to SEQ ID NO: 1, SEQ ID NO: 2, or SEQ ID NO:3.
14. The method of either of embodiments 12 or 13, wherein the compound comprises a soluble fragment of VSIG3.
15. The method of any one of embodiments 12 to 14, wherein the compound comprises the extracellular region of VSIG3.
16. The method of embodiment 15, wherein the compound comprises SEQ ID NO:2.
17. The method of either of embodiments 15 or 16, wherein the compound comprises a fusion protein.
18. The method of any one of embodiments 15 to 17, wherein the compound comprises an Fc domain.
19. The method of embodiment 18, wherein the compound comprises SEQ ID NO:3.
20. The method of any one of embodiments 1 to 19, wherein the compound comprises a VISTA polypeptide.
21. The method of embodiment 20, wherein the compound comprises a protein having at least 80% sequence identity to SEQ ID NO:4, SEQ ID NO: 5, or SEQ ID NO:6.
22. The method of either of embodiments 20 or 21, wherein the compound comprises a soluble fragment of VISTA.
23. The method of any one of embodiments 20 to 23, wherein the compound comprises the extracellular region of VISTA.
24. The method of embodiment 23, wherein the compound comprises SEQ ID NO:5.
25. The method of any one of embodiments 20 to 24, wherein the compound comprises a fusion protein.
26. The method of any one of embodiments 20 to 25, wherein the compound comprises an Fc domain.
27. The method of embodiment 26, wherein the compound comprises SEQ ID NO:6.
28. The method of any one of embodiments 1 to 27, wherein the compound comprises a coiled-coil domain of a cartilage oligomeric matrix protein (COMP).
29. The method of embodiment 28, wherein the COMP comprises a rat COMP or a human COMP.
30. The method of either of embodiments 28 or 29, wherein the coiled-coil domain comprises a pentameric coiled coil domain.
31. The method of any one of embodiments 28 to 30, wherein the coiled-coil domain is covalently linked to a VSIG3 polypeptide or a VISTA polypeptide or both.
32. The method of embodiment 31, wherein the compound comprises a linker domain.
33. The method of embodiment 32, wherein the linker domain comprises NSGGGSGGGTG (SEQ ID NO:13) or LDRNLPPLAPLGP (SEQ ID NO:14) or both.
34. The method of any one of embodiments 28 to 33, wherein the compound comprises an alkaline phosphatase.
35. The method of any one of embodiments 28 to 34, wherein the compound comprises a TEV cleavage site.

36. The method of any one of embodiments 1 to 35, wherein the compound abrogates the binding of VISTA and VSIG3.
37. The method of any one of embodiments 1 to 36, wherein the compound abrogates VISTA signaling.
38. The method of any one of embodiments 1 to 37, wherein the compound abrogates VSIG3 signaling.
39. The method of any one of embodiments 1 to 38, wherein the compound affects CD3-induced IL-2 production, CD3-induced interferon-γ production, CD3-induced RANTES production, CD3-induced MIP-1 alpha production, CD3-induced IL-17 production, or CD3-induced CXCL11 production, or a combination thereof.
40. The method of any one of embodiments 1 to 39, wherein the compound affects T cell proliferation.
41. The method of any one of embodiments 1 to 40, the method further comprising treating a subject with a therapeutically effective amount of the compound.
42. The method of embodiment 41 wherein VSIG3 is overexpressed in a biological sample obtained from the subject.

Antibody Embodiments

1. A monoclonal antibody that binds to VSIG3.
2. The anti-VSIG3 antibody of embodiment 1, wherein the antibody blocks a VSIG3-VISTA interaction, a VSIG3-VSIG8 interaction, multimerization of VSIG3, or multimerization of VISTA, or a combination thereof.
3. The anti-VSIG3 antibody of either of embodiments 1 or 2, the antibody comprising
    an antibody that binds to the same VSIG3 epitope as an antibody produced by one of the clones of Table 2A; or
    an antibody produced by one of the clones of Table 2A.
4. The anti-VSIG3 antibody of any one of embodiments 1 to 3, wherein an anti-VSIG3 antibody comprises
    at least one of
        a heavy chain variable region of an antibody produced by one or more of the clones of Table 2A; or
        a light chain variable region of an antibody produced by one or more of the clones of Table 2A.
5. The anti-VSIG3 antibody of any one of embodiments 1 to 4, wherein an anti-VSIG3 antibody comprises
    at least one of
        a heavy chain variable region comprising one or more complementary determining regions (CDRs) of the heavy chain variable regions of an antibody produced by one of the clones of Table 2A; or
        a light chain variable region comprising one or more CDRs of the light chain variable regions of an antibody produced by one of the clones of Table 2A.
6. The anti-VSIG3 antibody of any one of embodiments 1 to 5, wherein an anti-VSIG3 antibody comprises an antibody produced by one or more of the clones of Table 2A.
7. A monoclonal antibody produced by one or more of the clones of Table 2A.
8. A monoclonal antibody, wherein the monoclonal antibody comprises
    at least one of
        a heavy chain variable region of an antibody produced by one or more of the clones of Table 2A; or
        a light chain variable region of an antibody produced by one or more of the clones of Table 2A.
9. A monoclonal antibody, wherein the monoclonal antibody comprises
    at least one of
        a heavy chain variable region comprising one or more complementary determining regions (CDRs) of the heavy chain variable regions of an antibody produced by one of the clones of Table 2A; or
        a light chain variable region comprising one or more CDRs of the light chain variable regions of an antibody produced by one of the clones of Table 2A.
10. A monoclonal antibody, wherein the monoclonal antibody comprises
    each of the complementary determining regions (CDRs) of a heavy chain variable region of a monoclonal antibody produced by one of the clones of Table 2A, or
    each of the CDRs of a light chain variable region of a monoclonal antibody produced by one of the clones of Table 2A, or
    each of the CDRs of a heavy chain variable region of a monoclonal antibody produced by one of the clones of Table 2A and each of the CDRs of a light chain variable region of a monoclonal antibody produced by one of the clones of Table 2A.
13. A monoclonal antibody, wherein the monoclonal antibody comprises an amino acid sequence that is
    at least 80% identical to one or more complementary determining regions (CDRs) of the heavy chain variable region of a monoclonal antibody produced by a clone of Table 2A; or
    at least 80% identical to one or more CDRs of the light chain variable region of a monoclonal antibody produced by a clone of Table 2A, or
    at least 80% identical to one or more CDRs of the heavy chain variable region of a monoclonal antibody produced by a clone of Table 2A and at least 80% identical to one or more CDRs of the light chain variable region of a monoclonal antibody produced by a clone of Table 2A.
14. The monoclonal antibody of any one of embodiments 7 to 13, wherein the monoclonal antibody binds to VSIG3.
15. The monoclonal antibody of any one of embodiments 7 to 14, wherein the monoclonal antibody comprises an IgG antibody.
16. The monoclonal antibody of any one of embodiments 7 to 15, wherein the monoclonal antibody abrogates the binding of VSIG3 to a VSIG3 ligand.
17. The monoclonal antibody of any one of embodiments 7 to 16, wherein the monoclonal antibody abrogates the binding of VSIG3 to VISTA.
18. The monoclonal antibody of any one of embodiments 7 to 17, wherein the monoclonal antibody comprises an antigen-binding fragment comprising a Fab fragment, a Fab' fragment, a F(ab)$_2$ fragment, or a FIT fragment, or a combination thereof.
19. A composition comprising the monoclonal antibody or anti-VSIG3 antibody of any one of embodiments 1 to 18.
20. A kit comprising the monoclonal antibody or anti-VSIG3 antibody of any one of embodiments 1 to 18.

Compound Embodiments

1. A compound that modulates the interaction of VISTA and VSIG3.
2. The compound of embodiment 1 comprising an anti-VSIG3 antibody.
3. The compound of embodiment 2, wherein the anti-VSIG3 antibody comprises
    an antibody that binds to the same VSIG3 epitope as an antibody produced by one of the clones of Table 2A; or
    an antibody produced by one of the clones of Table 2A.

4. The compound of any one of embodiments 1 to 3, wherein an anti-VSIG3 antibody comprises
at least one of
a heavy chain variable region of an antibody produced by one or more of the clones of Table 2A; or
a light chain variable region of an antibody produced by one or more of the clones of Table 2A.
5. The compound of any one of embodiments 1 to 4, wherein an anti-VSIG3 antibody comprises
at least one of
a heavy chain variable region comprising one or more complementary determining regions (CDRs) of the heavy chain variable regions of an antibody produced by one of the clones of Table 2A; or
a light chain variable region comprising one or more CDRs of the light chain variable regions of an antibody produced by one of the clones of Table 2A.
6. The compound of any one of embodiments 1 to 5, wherein an anti-VSIG3 antibody comprises an antibody produced by one or more of the clones of Table 2A.
7. The compound of any one of embodiments 2 to 6, wherein the compound comprises an antigen-binding fragment.
8. The compound of any one of embodiments 1 to 7, wherein the compound abrogates the binding of VISTA and VSIG3.
9. The compound of any one of embodiments 1 to 8, wherein the compound modulates the multimerization of VSIG3.
10. The compound of any one of embodiments 1 to 9, wherein the compound abrogates VISTA signaling.
11. The compound of any one of embodiments 1 to 10, wherein the compound abrogates VSIG3 signaling.
12. The compound any one of embodiments 1 to 11, wherein the compound affects CD3-induced IL-2 production, CD3-induced interferon-γ production, CD3-induced RANTES production, CD3-induced MIP-1 alpha production, CD3-induced IL-17 production, or CD3-induced CXCL11 production, or a combination thereof.
13. The compound any one of embodiments 1 to 12, wherein the compound affects T cell proliferation.
14. The compound of any one of embodiments 1 to 13, wherein the compound comprises a VSIG3 polypeptide.
15. The compound of embodiment 14, wherein the compound comprises protein having at least 80% sequence identity to SEQ ID NO: 1, SEQ ID NO: 2, or SEQ ID NO:3.
16. The compound of embodiment 14 or 15, wherein the compound comprises a soluble fragment of VSIG3.
17. The compound of any one of embodiments 14 to 16, wherein the compound comprises the extracellular region of VSIG3.
18. The compound of embodiment 17, wherein the compound comprises SEQ ID NO:2.
19. The compound of any one of embodiments 17 to 18, wherein the compound comprises a fusion protein.
20. The compound of any one of embodiments 14 to 19, wherein the compound comprises an Fc domain.
21. The compound of embodiment 20, wherein the compound comprises SEQ ID NO:3.
22. The compound of any one of embodiments 1 to 21, wherein the compound comprises a VISTA polypeptide.
23. The compound of embodiment 22, wherein the compound comprises a protein having at least 80% sequence identity to SEQ ID NO:4, SEQ ID NO: 5, or SEQ ID NO:6.
24. The compound of embodiment 22 or 23, wherein the compound comprises a soluble fragment of VISTA.
25. The compound of any one of embodiments 22 to 24, wherein the compound comprises the extracellular region of VISTA.
26. The compound of embodiment 25, wherein the compound comprises SEQ ID NO:5.
27. The compound of any one of embodiments 1 to 26, wherein the compound comprises a fusion protein.
28. The compound of any one of embodiments 1 to 27, wherein the compound comprises an Fc domain.
29. The compound of embodiment 28, wherein the compound comprises SEQ ID NO:6.
30. The compound of any one of embodiments 1 to 29, wherein the compound comprises a coiled-coil domain of a cartilage oligomeric matrix protein (COMP).
31. The compound of embodiment 30, wherein the COMP comprises a rat COMP or a human COMP.
32. The compound of either of embodiments 30 or 31, wherein the coiled-coil domain comprises a pentameric coiled coil domain.
33. The compound of any one of embodiments 30 to 32, wherein the coiled-coil domain is covalently linked to a VSIG3 polypeptide or a VISTA polypeptide or both.
34. The compound of embodiment 33, wherein the compound comprises a linker domain.
35. The compound of embodiment 34, wherein the linker domain comprises NSGGGSGGGTG (SEQ ID NO:13) or LDRNLPPLAPLGP (SEQ ID NO:14) or both.
36. The compound of any one of embodiments 30 to 35, wherein the compound comprises an alkaline phosphatase.
37. The compound of any one of embodiments 30 to 36, wherein the compound comprises TEV cleavage site.
38. The compound of any one of embodiments 1 to 37, wherein the compound abrogates the binding of VISTA and VSIG3.
39. A composition comprising the compound of any of embodiments 1 to 38.
40. A kit comprising the compound of any one of embodiments 1 to 38.
41. A method comprising treating a subject with a therapeutically effective amount of the compound of any one of embodiments 1 to 38.
42. The method of embodiment 41 wherein VSIG3 is overexpressed in a biological sample obtained from the subject.

Composition Embodiments

1. A composition comprising two or more anti-VSIG3 antibodies, wherein at least one anti-VSIG3 antibody comprises an antibody produced by a clone of Table 2A.
2. The composition of embodiment 1, wherein each anti-VSIG3 antibody blocks one or more of a VSIG3-VISTA interaction, a VSIG3-VISTA8 interaction, multimerization of VSIG3, and multimerization of VISTA.
3. The composition of either of embodiments 1 or 2, wherein the two or more anti-VSIG3 antibodies bind to different epitopes.
4. The composition of any of embodiments 1 to 3 wherein at least one of the anti-VSIG3 antibodies interacts with an ABE Ig face of VSIG.
5. The composition of any of embodiments 1 to 4 wherein at least one of the anti-VSIG3 antibodies interacts with an GFC Ig face of VSIG.
6. A composition comprising an anti-VSIG3 antibody and an anti-VISTA antibody wherein the composition blocks a VSIG3-VISTA interaction, a VSIG3-VISTA8 interaction, multimerization of VSIG3, or multimerization of VISTA, or a combination thereof; and wherein the anti-VSIG3 antibody comprises an antibody produced by one or more of the clones of Table 2A.

7. A composition comprising a multimerized VSIG3, a multimerized VISTA, or a multimerized VSIG8, or a combination thereof.

Polyclonal Antibody Embodiments

1. A polyclonal antibody generated by immunizing with an immunogen, wherein the immunogen comprises a polypeptide, the polypeptide comprising one or more of the polypeptides described in Table 3A.
2. A polyclonal antibody generated by immunizing with an immunogen, wherein the immunogen comprises a polypeptide, the polypeptide consisting of one or more of the polypeptides described in Table 3A.
3. A polyclonal antibody generated by immunizing with an immunogen, wherein the immunogen comprises a polypeptide, the polypeptide consisting of a polypeptide described in Table 3A.
4. A polyclonal antibody generated by immunizing with a polypeptide, the polypeptide consisting of a peptide described in Table 3A.
5. The polyclonal antibody of any one of embodiments 1 to 4, wherein the polyclonal antibody binds VSIG3.

The present invention is illustrated by the following examples. It is to be understood that the particular examples, materials, amounts, and procedures are to be interpreted broadly in accordance with the scope and spirit of the invention as set forth herein.

EXAMPLES

Unless otherwise indicated, all incubations in the following examples were at room temperature and all reagents, starting materials, and solvents used were purchased from commercial suppliers (such as Sigma-Aldrich, St. Louis, MO) and were used without further purification.

Example 1—Monoclonal Antibodies

Recombinant human VSIG3 Fc Chimera ("rhVSIG3"— encoded by SEQ ID NO:3; see Table 1) specifically binds to a recombinant human VISTA Fc Chimera ("rhVISTA"— encoded by SEQ ID NO:6; see Table 1) on a functional ELISA binding assay. rhVISTA was coated on the wells of a ELISA microtiter plate at 2 µg/ml in a 100 µL volume. Following blocking of the wells with 1% BSA, varying amounts of rhVSIG3 labeled with biotin was added. Biotin label associated with the plate due to the rhVSIG3-rhVISTA interaction was detected with streptavidin-HRP. As shown in FIG. 1A, when rhVISTA is immobilized on wells of a microtiter plate at 2 µg/mL in a 100 volume per well, the concentration of rhVSIG3 that produces 50% of the optimal binding response is approximately 0.25 µg/mL. The non-specific binding is subtracted and in all cases was less than 5% of the total signal.

Monoclonal anti-VSIG3 antibodies were developed and specificity was tested with a direct ELISA test using a coating with His-tagged rhVSIG3 protein at 250 ng/mL. Results for antibodies produced by the clones of Table 2 are shown in the right-most column of Table 2A.

Figure 1B:
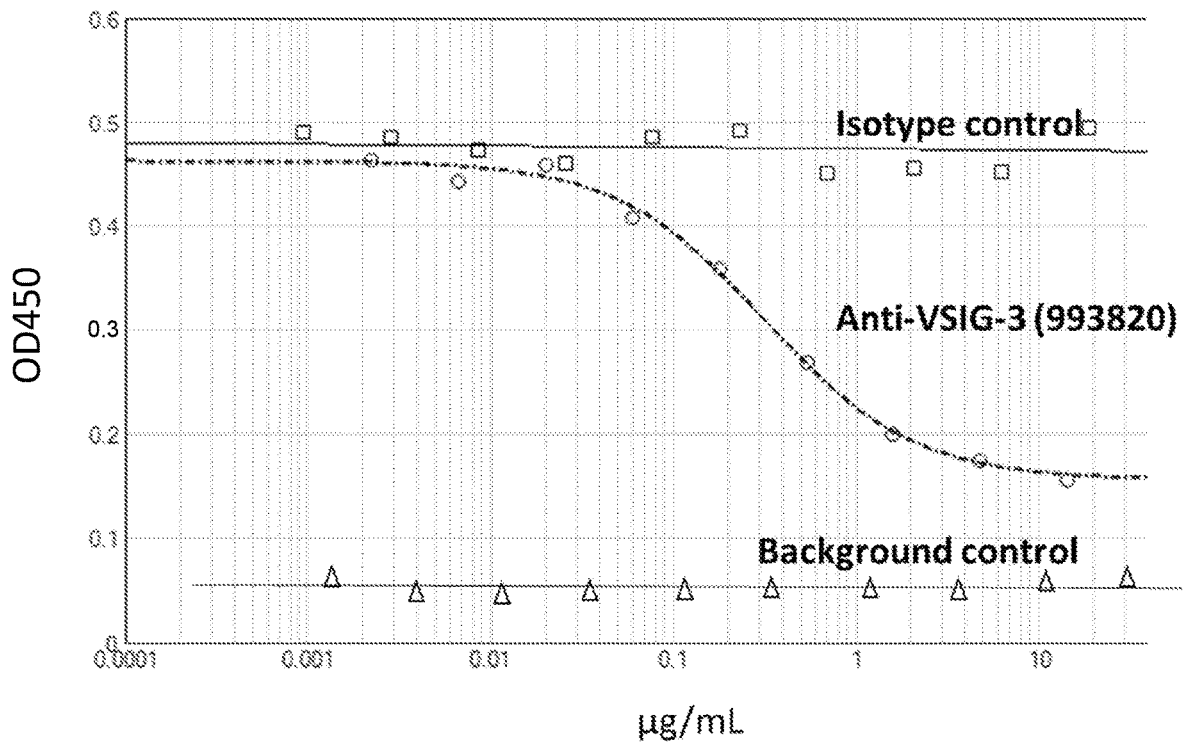
FIG. 1B shows a representative result of the effect of an anti-VSIG3 antibody on the binding of rhVSIG3 and rhVSIG3 protein. Antibody Isotype control (□—open squares) showed no blocking; antibody clone 993820 (○—open circles) showed 8% blocking of the binding between VSIG3 and VISTA with an ED50 of 0.32 μg/mL. The ED50 reflects the concentration of an antibody needed to retrieve 50% of maximal blocking

To test the effect of the monoclonal anti-VSIG3 antibodies (including the antibodies produced by one of the clones of Table 2A) on the rhVSIG3-rhVISTA interaction, ELISA plates were coated with rhVSIG3 at 2 µg/ml in a 100 µL volume overnight at 2-8° C. Following blocking with 1% BSA, varying amounts of ms×human VSIG3 was added and pretreated for 2 hours at room temperature. Biotinylated rhVISTA protein was added at 7.5 µg/ml in a 100 µL volume to each well. The rhVSIG3-rhVISTA interaction was detected using streptavidin-HRP and followed by a color reaction. FIG. 1B shows a representative result.

Additional results indicating the specificity of the interaction between rhVSIG3 and rhVISTA as tested using the ELISA assay in the presence of antibodies specific for VISTA are summarized in Table 2B. Thirty monoclonal anti-human VSIG3 antibodies were tested using functional ELISA binding assay. As shown in Table 2B, 26 of 30 monoclonal antibodies to VSIG3 tested blocked the interaction between rhVSIG3 and rhVISTA.

TABLE 2A

| Antibody Clone | Alternate name | Immunogen | Type | rhVSIG-3/his-1 |
|---|---|---|---|---|
| 774206 | 774206.111 | rhVSIG-3 aa1-245/His | mouse mono | yes |
| 774208 | 774208.111 | rhVSIG-3 aa1-245/His | mouse mono | yes |
| 774211 | 774211.111 | rhVSIG-3 aa1-245/His | mouse mono | yes |
| 774213 | 774213.111 | rhVSIG-3 aa1-245/His | mouse mono | yes |
| 774220 | 774220.111 | rhVSIG-3 aa1-245/His | mouse mono | yes |
| 774221 | 774221.111 | rhVSIG-3 aa1-245/His | mouse mono | yes |
| 774225 | 774225.111 | rhVSIG-3 aa1-245/His | mouse mono | yes |
| 774226 | 774226.111 | rhVSIG-3 aa1-245/His | mouse mono | yes |
| 774232 | 774232.111 | rhVSIG-3 aa1-245/His | mouse mono | yes |
| 774234 | 774234.111 | rhVSIG-3 aa1-245/His | mouse mono | yes |
| 973401 | 973401.111 | rhVSIG-3 aa1-245/His | mouse mono | yes |
| 973404 | 973404.111 | rhVSIG-3 aa1-245/His | mouse mono | yes |
| 973408 | 973408.111 | rhVSIG-3 aa1-245/His | mouse mono | yes |
| 973422 | 973422.111 | rhVSIG-3 aa1-245/His | mouse mono | yes |
| 973423 | 973423.111 | rhVSIG-3 aa1-245/His | mouse mono | yes |
| 973428 | 973428.111 | rhVSIG-3 aa1-245/His | mouse mono | yes |
| 973433 | 973433.111 | rhVSIG-3 aa1-245/His | mouse mono | yes |
| 973435 | 973435.111 | rhVSIG-3 aa1-245/His | mouse mono | yes |
| 973436 | 973436.111 | rhVSIG-3 aa1-245/His | mouse mono | yes |
| 993501 | 993501.1 or .111 | rhVSIG-3 aa1-245/His | mouse mono | weak |
| 993502 | 993502.1 or .111 | rhVSIG-3 aa1-245/His | mouse mono | yes |
| 993503 | 993503.1 or .111 | rhVSIG-3 aa1-245/His | mouse mono | not detected |
| 993505 | 993505.1 or .111 | rhVSIG-3 aa1-245/His | mouse mono | yes |
| 993508 | 993508.1 or .111 | rhVSIG-3 aa1-245/His | mouse mono | yes |
| 993512 | 993512.1 or .111 | rhVSIG-3 aa1-245/His | mouse mono | yes |
| 993515 | 993515.1 or .111 | rhVSIG-3 aa1-245/His | mouse mono | yes |
| 993517 | 993517.1 or .111 | rhVSIG-3 aa1-245/His | mouse mono | not detected |

TABLE 2A-continued

| Antibody Clone | Alternate name | Immunogen | Type | rhVSIG-3/his-1 |
|---|---|---|---|---|
| 993518 | 993518.1 or .111 | rhVSIG-3 aa1-245/His | mouse mono | yes |
| 993521 | 993521.1 or .111 | rhVSIG-3 aa1-245/His | mouse mono | not detected |
| 993523 | 993523.1 or .111 | rhVSIG-3 aa1-245/His | mouse mono | not detected |
| 993527 | 993527.1 or .111 | rhVSIG-3 aa1-245/His | mouse mono | not detected |
| 993611 | 993611.1 or .111 | rhVSIG-3 aa1-245/His | mouse mono | yes |
| 993619 | 993619.1 or .111 | rhVSIG-3 aa1-245/His | mouse mono | yes |
| 993620 | 993620.1 or .111 | rhVSIG-3 aa1-245/His | mouse mono | yes |
| 993621 | 993621.1 or .111 | rhVSIG-3 aa1-245/His | mouse mono | yes |
| 993622 | 993622.1 or .111 | rhVSIG-3 aa1-245/His | mouse mono | not detected |
| 993623 | 993623.1 or .111 | rhVSIG-3 aa1-245/His | mouse mono | not detected |
| 993625 | 993625.1 or .111 | rhVSIG-3 aa1-245/His | mouse mono | yes |
| 993626 | 993626.1 or .111 | rhVSIG-3 aa1-245/His | mouse mono | yes |
| 993627 | 993627.1 or .111 | rhVSIG-3 aa1-245/His | mouse mono | yes |
| 993628 | 993628.1 or .111 | rhVSIG-3 aa1-245/His | mouse mono | yes |
| 993629 | 993629.1 or .111 | rhVSIG-3 aa1-245/His | mouse mono | yes |
| 993630 | 993630.1 or .111 | rhVSIG-3 aa1-245/His | mouse mono | not detected |
| 993804 | 993804.1 or .111 | rhVSIG-3 aa1-245/His | rat mono | not detected |
| 993810 | 993810.1 or .111 | rhVSIG-3 aa1-245/His | rat mono | yes |
| 993817 | 993817.1 or .111 | rhVSIG-3 aa1-245/His | rat mono | weak |
| 993820 | 993820.1 or .111 | rhVSIG-3 aa1-245/His | rat mono | yes |
| 993821 | 993821.1 or .111 | rhVSIG-3 aa1-245/His | rat mono | yes |
| 993822 | 993822.1 or .111 | rhVSIG-3 aa1-245/His | rat mono | not detected |
| 993824 | 993824.1 or .111 | rhVSIG-3 aa1-245/His | rat mono | not detected |
| 993825 | 993825.1 or .111 | rhVSIG-3 aa1-245/His | rat mono | yes |
| 993826 | 993826.1 or .111 | rhVSIG-3 aa1-245/His | rat mono | yes |
| 993832 | 993832.1 or .111 | rhVSIG-3 aa1-245/His | rat mono | weak |
| 993835 | 993835.1 or .111 | rhVSIG-3 aa1-245/His | rat mono | yes |
| 993836 | 993836.1 or .111 | rhVSIG-3 aa1-245/His | rat mono | yes |
| 993839 | 993839.1 or .111 | rhVSIG-3 aa1-245/His | rat mono | yes |
| 993843 | 993843.1 or .111 | rhVSIG-3 aa1-245/His | rat mono | yes |
| 993848 | 993848.1 or .111 | rhVSIG-3 aa1-245/His | rat mono | not detected |
| 993851 | 993851.1 or .111 | rhVSIG-3 aa1-245/His | rat mono | weak |

TABLE 2B

| Antibody clone # | Immunogen | Antibody type | Blocking VSIG-3 and VISTA binding |
|---|---|---|---|
| 973404 | rhVSIG-3(1-245) | Mouse mono | 80% blocking, ND50: 0.526 µg/mL |
| 973422 | rhVSIG-3(1-245) | Mouse mono | 90% blocking, ND50: 0.519 µg/mL |
| 973423 | rhVSIG-3(1-245) | Mouse mono | 75% blocking, ND50: 0.309 µg/mL |
| 973436 | rhVSIG-3(1-245) | Mouse mono | 80% blocking, ND50: 0.439 µg/mL |
| 973435 | rhVSIG-3(1-245) | Mouse mono | No blocking |
| 993501 | rhVSIG-3(1-245) | Mouse mono | 60% blocking, ND50: 0.433 µg/mL |
| 993502 | rhVSIG-3(1-245) | Mouse mono | 60% blocking, ND50: 0.455 µg/mL |
| 993508 | rhVSIG-3(1-245) | Mouse mono | 60% blocking, ND50: 0.448 µg/mL |
| 993512 | rhVSIG-3(1-245) | Mouse mono | 60% blocking, ND50: 0.471 µg/mL |
| 993515 | rhVSIG-3(1-245) | Mouse mono | 60% blocking, ND50: 0.388 µg/mL |
| 993518 | rhVSIG-3(1-245) | Mouse mono | 60% blocking, ND50: 0.665 µg/mL |
| 993521 | rhVSIG-3(1-245) | Mouse mono | 60% blocking, ND50: 0.255 µg/mL |
| 993527 | rhVSIG-3(1-245) | Mouse mono | No blocking |
| 993611 | rhVSIG-3(1-245) | Mouse mono | 80% blocking, ND50: 2.87 µg/mL |
| 993619 | rhVSIG-3(1-245) | Mouse mono | 80% blocking, ND50: 2.46 µg/mL |
| 993620 | rhVSIG-3(1-245) | Mouse mono | 80% blocking, ND50: 2.66 µg/mL |
| 993622 | rhVSIG-3(1-245) | Mouse mono | 60% blocking, ND50: 2.15 µg/mL |
| 993625 | rhVSIG-3(1-245) | Mouse mono | 80% blocking, ND50: 5.12 µg/mL |
| 993626 | rhVSIG-3(1-245) | Mouse mono | 60% blocking, ND50: 2.03 µg/mL |
| 993628 | rhVSIG-3(1-245) | Mouse mono | 80% blocking, ND50: 3.18 µg/mL |
| 993630 | rhVSIG-3(1-245) | Mouse mono | No blocking |
| 993820 | rhVSIG-3(1-245) | Rat mono | 80% blocking, ND50: 0.32 µg/mL |
| 993821 | rhVSIG-3(1-245) | Rat mono | 80% blocking, ND50: 0.381 µg/mL |
| 993822 | rhVSIG-3(1-245) | Rat mono | 80% blocking, ND50: 0.153 µg/mL |
| 993826 | rhVSIG-3(1-245) | Rat mono | 80% blocking, ND50: 0.396 µg/mL |
| 993836 | rhVSIG-3(1-245) | Rat mono | 80% blocking, ND50: 0.315 µg/mL |
| 993839 | rhVSIG-3(1-245) | Rat mono | 80% blocking, ND50: 0.406 µg/mL |
| 993843 | rhVSIG-3(1-245) | Rat mono | 80% blocking, ND50: 0.416 µg/mL |
| 993848 | rhVSIG-3(1-245) | Rat mono | 80% blocking, ND50: 0.279 µg/mL |
| 993851 | rhVSIG-3(1-245) | Rat mono | No blocking |

Example 2—Polyclonal Antibodies

Rabbit polyclonal anti-human VSIG-3 antibodies were generated using the polypeptides listed in Table 3A and were tested as described in Example 1. Briefly, rhVSIG-3 was coated on the wells of a ELISA microtiter plate at 2 µg/ml in a 100 µL volume overnight at 2-8° C. Following blocking of the wells with 1% BSA, varying amounts of polyclonal rabbit anti-hVSIG-3 peptide antibodies were added and pretreated for 2 hours at room temperature. Then biotinylated rhVISTA at 7.5 µg/mL was added into each well in a 100 µL volume.

Figure 2:
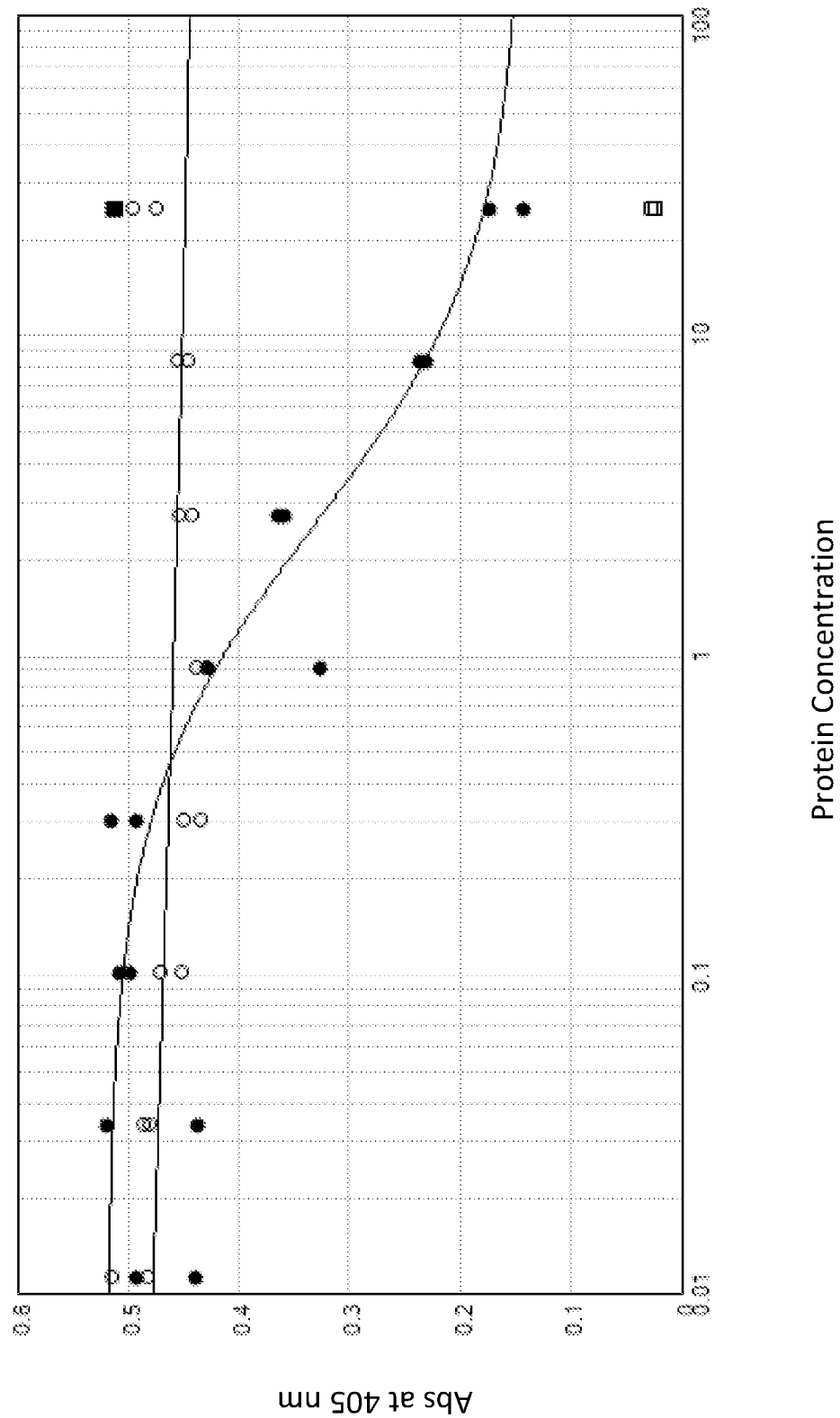
FIG. 2 shows a representative result for a polyclonal rabbit anti-human VSIG3 peptide antibody blocking the binding of rhVSIG3 to rhVISTA. The rhVSIG3-rhVISTA interaction was detected using streptavidin-HRP followed by a color reaction. Antibody I205 (○—open circles) showed no blocking; rabbit antibody G129 (●-filled circles) showed 70% blocking the binding between VSIG-3 and VISTA with an ED50 of 2.59 ug/mL. The ED50 reflects the concentration of an antibody needed to retrieve 50% of maximal blocking.

Exemplary results are shown in FIG. 2 and Table 3. As shown in Table 3B, six of the 16 rabbit polyclonal antibodies tested blocked the interaction between rhVSIG3 and rhVISTA. The ED50 reflects the concentration of an antibody needed to retrieve 50% of maximal blocking

TABLE 3A

| Antibody | Peptide Immunogen | Antibody type |
| --- | --- | --- |
| Q111 | Q111 to C120 | rabbit poly |
| H89 | H89 to M98 plus C | rabbit poly |
| L138 | L138 to C149 | rabbit poly |
| I205 | I205 to C215 | rabbit poly |
| V216 | V216 to C226 | rabbit poly |
| Y176 | C plus Y176 to K186 | rabbit poly |
| G129 | G129 to L138 plus C | rabbit poly |
| C44 | C44 to L55 | rabbit poly |
| S154 | S154 to C165 | rabbit poly |
| D194 | D194 to N204 plus C | rabbit poly |
| G78 | G78 to F88 plus C | rabbit poly |
| C120 | C120 to N132 | rabbit poly |
| Q33 | Q33 to C44 | rabbit poly |
| N66 | N66 to Q77 plus C | rabbit poly |
| C165 | C165 to T175 | rabbit poly |
| K186 | C plus K186 to Q195 | rabbit poly |

TABLE 3B

| Antibody | Peptide Immunogen | Antibody type | Blocking activity |
| --- | --- | --- | --- |
| Q111 | Q111 to C120 | Rabbit poly | No blocking |
| H89 | H89 to M98 plus C | Rabbit poly | No blocking |
| L138 | L138 to C149 | Rabbit poly | No blocking |
| I205 | I205 to C215 | Rabbit poly | No blocking |
| V216 | V216 to C226 | Rabbit poly | No blocking |
| Y176 | C plus Y176 to K186 | Rabbit poly | No blocking |
| G129 | G129 to L138 plus C | Rabbit poly | 70% blocking, ED50 = 2.59 ug/mL |
| C44 | C44 to L55 | Rabbit poly | No blocking |
| S154 | S154 to C165 | Rabbit poly | 50% blocking, ED50 = 6.59 ug/mL |
| D194 | D194 to N204 plus C | Rabbit poly | 40% blocking, ED50 = 3.78 ug/mL |
| G78 | G78 to F88 plus C | Rabbit poly | No blocking |
| C120 | C120 to N132 | Rabbit poly | 40% blocking, ED50 = 10.0 ug/mL |
| Q33 | Q33 to C44 | Rabbit poly | 40% blocking, ED50 = 10.1 ug/mL |
| N66 | N66 to Q77 plus C | Rabbit poly | 40% blocking, ED50 = 6.06 ug/mL |
| C165 | C165 to T175 | Rabbit poly | No blocking |
| K186 | C plus K186 to Q195 | Rabbit poly | No blocking |

Example 3—Effect of Monoclonal and Polyclonal Antibodies on T Cell Functions

IL-2 Secretion

Figure 3:
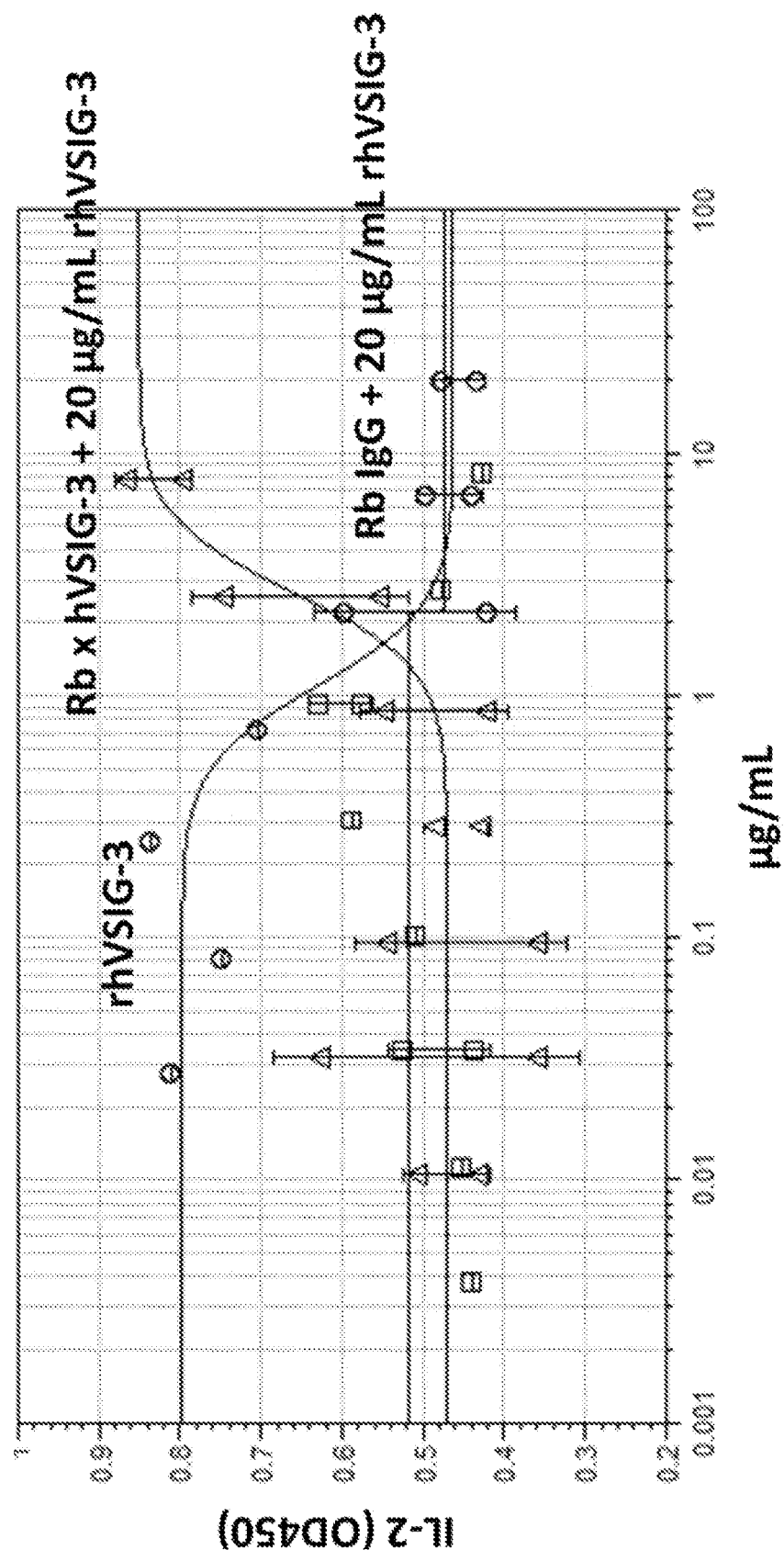
FIG. 3 shows an exemplary rabbit polyclonal anti-human VSIG3 antibody attenuates the ability of VSIG3 protein to inhibit IL-2 secretion from activated T cells. Mouse anti-human CD3 antibody was coated on a 96 well plate at 1 μg/mL overnight at 2-8° C. Recombinant human VSIG3 (rhVSIG3) protein was immobilized on the assay plates in a serial dilution (○—open circles) or at 20 μg/mL and incubated for 3 hours at 37° C. Serially diluted polyclonal rabbit anti-human VSIG3 (N66) or an isotype control (rabbit IgG) were added and co-incubated with the 20 μg/mL rhVSIG3 protein for 1-2 hours at room temperature. Human T cells were isolated from human PBMCs using MagCellect Human CD3+ Isolation Kit (R&D Systems, Minneapolis, MN), and isolated human T cells were added to the plate $(2\times10^5/\text{well})$ and cultured for 24 hours at 37° C. in the presence of 5% $CO_2$. Secreted IL-2 was measured in the cell culture supernatant using QUANTIKINE human IL-2 ELISA Kit (R&D Systems, Minneapolis, MN). Antibody Isotype control, rabbit IgG (□—open squares) showed no blocking of VSIG3's effect on IL-2 secretion; polyclonal antibody clone N66 (Δ—triangle) showed blocking of VSIG3's effect on IL-2 secretion.

As shown in FIG. 3, rhVSIG3 significantly inhibited anti-CD3-induced IL-2 production by T cells in a dose dependent manner. A rabbit polyclonal anti-human VSIG3 antibody (N66) blocked the ability of VSIG3 to inhibit IL-2 secretion from activated T cells.

Mouse anti-human CD3 antibody was coated on a 96 well plate at 1 μg/mL overnight at 2-8° C. rhVSIG-3 protein was then immobilized on the assay plates in a serial dilution (open circles) or at 20 μg/mL and incubated for 3 hours at 37° C. Serially diluted polyclonal rabbit anti-human VSIG-3 (N66) or an isotype control (rabbit IgG) were added and co-incubated with the 20 μg/mL rhVSIG-3 protein for 1-2 hours at room temperature. Human T cells were isolated from human PBMCs using MagCellect Human CD3+ Isolation Kit (R&D Systems, Minneapolis, MN), and isolated human T cells were added to the plate ($2\times10^5$/well) and cultured for 24 hours at 37° C. in the presence of 5% $CO_2$. Secreted IL-2 was measured in the cell culture supernatant using QUANTIKINE human IL-2 ELISA Kit (R&D Systems, Minneapolis, MN). Results are shown in FIG. 3.

The observed ND50 for N66 was about 2.67 μg/mL and is expected to depend on the concentration of immobilized rhVSIG-3.

T cell Proliferation and Activation

Figure 4:
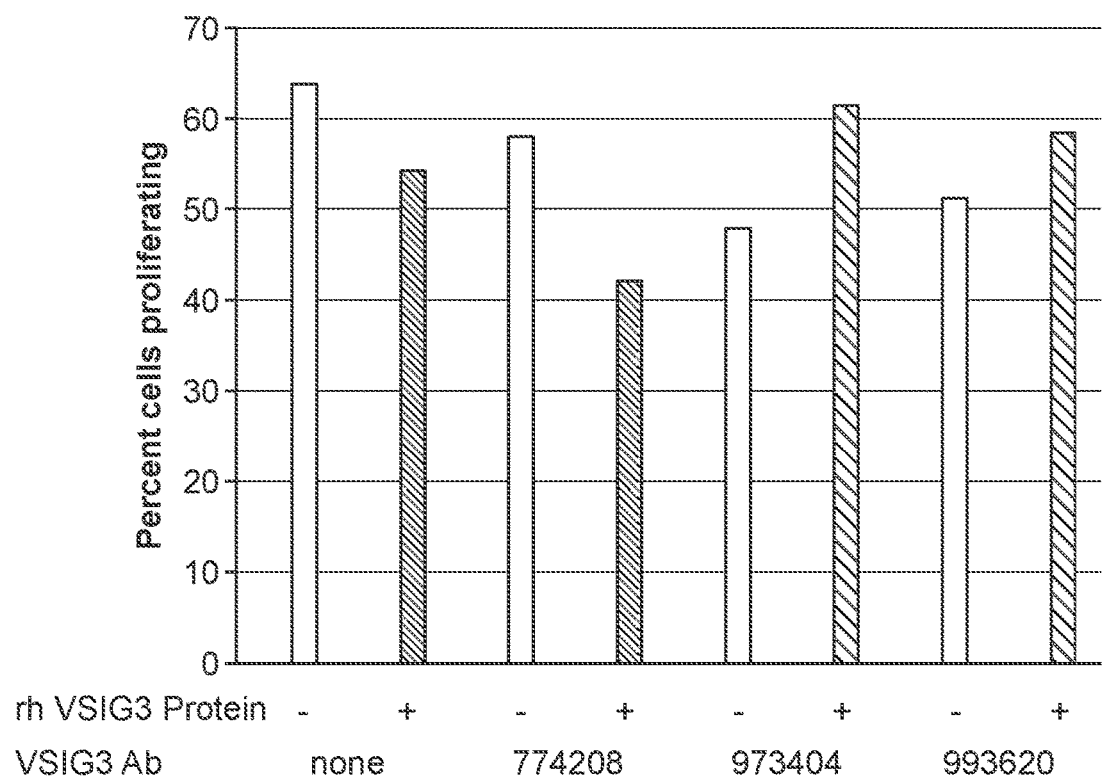
FIG. 4 shows rhVSIG3 protein can inhibit anti-CD3-induced cell proliferation of normal human peripheral blood T cells. This inhibition can be reversed by monoclonal anti-human VSIG3 antibody clones 973404 and 993620. Monoclonal antibody clone 774208 showed no effect on the proliferation of T-cells and represents a negative control.

As shown in FIG. 4 and Table 4, rhVSIG3 protein inhibits anti-CD3-induced cell proliferation and activation of normal human peripheral blood T cells, and anti-VSIG3 antibodies can block this inhibition.

Anti-human CD3 (1-5 μg/mL; R&D Systems, clone UCHT1, MAB100) and human IgG (control protein; 1-5 μg/mL; R&D Systems 100-HG) or rhVSIG3 protein (10-50 μg/ml) were coated onto 96 well plates together with the indicated anti-human VSIG3 antibody (1-10 μg/ml) by incubating overnight at 4° C. Plates were washed with PBS and blocked with 2.5% human AB serum (Innovative Research, Novi, MI) in PBS for 30 minutes. CD3+ T cells were negatively selected from human PBMC using a CD3+ T cell isolation kit (R&D Systems, MAGH101) labeled with Cell Trace Violet proliferation dye (Life Technologies per manufacturers specifications), and added to the wells ($5\times10^4$-$2\times10^5$ cells per well) in 200 μL of RPMI+10% human AB serum. Plates were incubated at 37° C. for 72-96 hours, then cells were harvested, and proliferation/cell activation was analyzed by flow cytometry.

As shown in FIG. 4 and Table 4, anti-CD3-induced proliferation of human T cells (FIG. 4, first grey bar) was inhibited by rhVSIG3 protein (hatched bar). Co-culture with monoclonal anti-human VSIG3 Ab 774208 did not affect this inhibition. However, culture with monoclonal anti-human VSIG3 antibody clones 973404 and 993620 was able to reverse rhVSIG3-mediated inhibition, indicating that these antibodies block VSIG3-induced inhibition of T cell proliferation. Additionally, polyclonal antibodies G129 and C120 were also able to reverse rhVSIG3-mediated inhibition, indicating that these antibodies block VSIG3-induced inhibition of T cell proliferation.

TABLE 4

| Antibody | Immunogen | Blocks inhibition of T cell proliferation |
| --- | --- | --- |
| 774208 | rhVSIG3 (1-245) | No |
| 973404 | rhVSIG3 (1-245) | Yes |
| 993620 | rhVSIG3 (1-245) | Yes |

Interferon-γ Secretion

Figure 5:
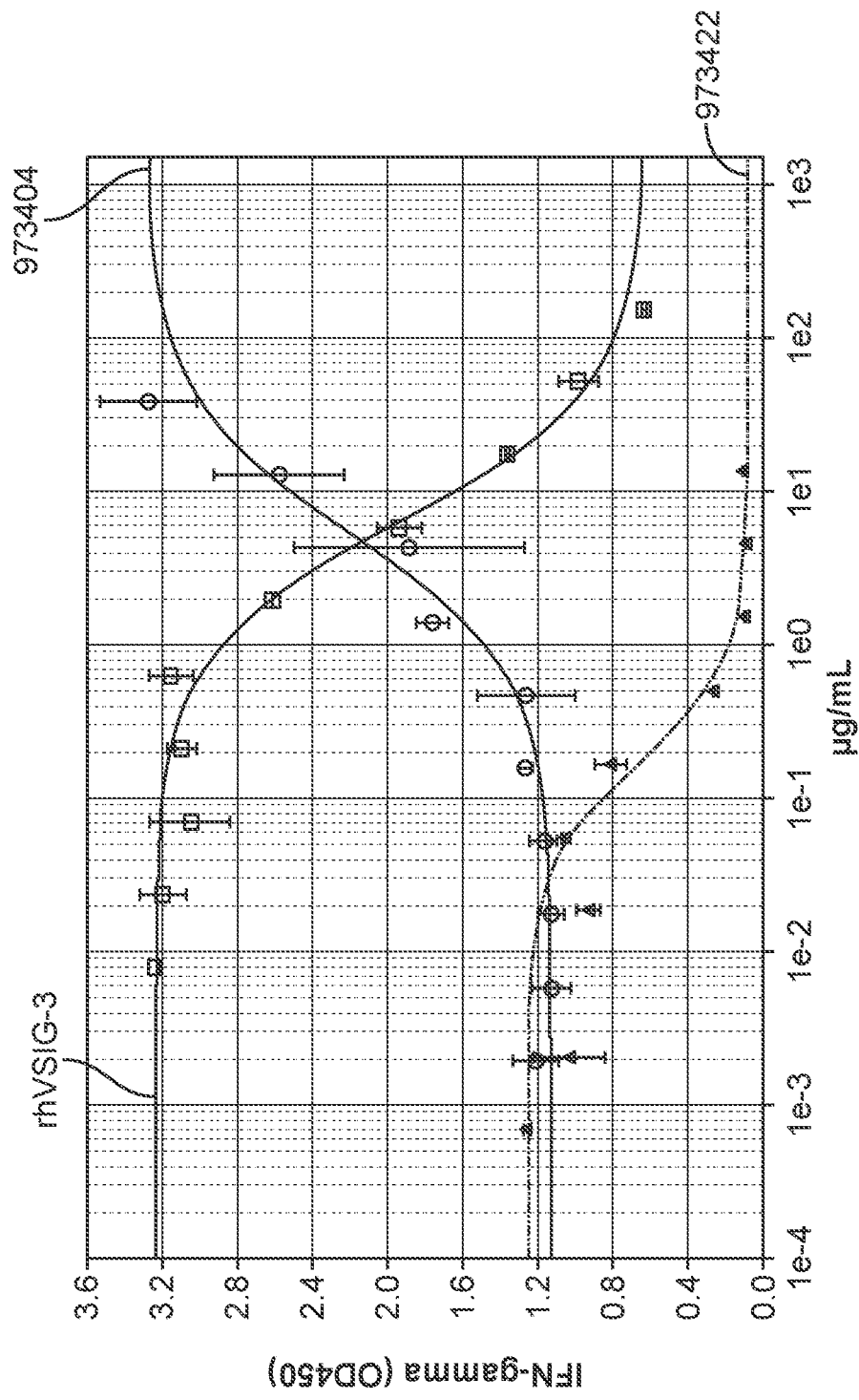
FIG. 5 shows an exemplary monoclonal anti-human VSIG3 antibody attenuates the ability of VSIG3 protein to inhibit interferon-γ secretion from activated T cells. Mouse anti-human CD3 antibody was coated on a 96 well plate at 1 μg/mL overnight at 2-8° C. Recombinant human VSIG3 (rhVSIG3) protein was immobilized on the assay plates in a serial dilution (□—open squares) or at 20 μg/mL and incubated for 3 hours at 37° C. Serial diluted monoclonal anti-human VSIG3 (973404 or 973422 clones) were added and co-incubated with the 20 μg/mL rhVSIG3 protein for 1-2 hours at room temperature. Human T cells were isolated from human PBMCs using MagCellect Human CD3+ T Cell Isolation Kit (R&D Systems, Minneapolis, MN). Isolated human T cells $(2\times10^5/\text{well})$ were added to the plate and cultured for 24 hours at 37° C. in the presence of 5% $CO_2$. Secreted interferon-γ was measured in the cell culture supernatant using QUANTIKINE human interferon-γ ELISA Kit (R&D Systems, Minneapolis, MN). Monoclonal antibody clone 973404 (°—open circles) showed blocking of VSIG3's effect on interferon-γ secretion. However Monoclonal antibody clone #973422 (Δ—triangles) showed further enhancement of VSIG3's effect on interferon-γ secretion.

As shown in FIG. 5, rhVSIG3 significantly inhibited anti-CD3-induced interferon-γ production by T cells in a dose dependent manner. An exemplary monoclonal anti-human VSIG-3 antibody (973404) blocked the ability of VSIG3 to inhibit interferon-γ secretion from activated T cells.

Mouse anti-human CD3 antibody was coated on a 96 well plate at 1 μg/mL overnight at 2-8° C. rhVSIG-3 protein was then immobilized on the assay plates in a serial dilution (□—open squares) or at 20 μg/mL and incubated for 3 hours at 37° C. Serial diluted monoclonal anti-human VSIG-3 (973404 or 973422) were added and co-incubated with the 20 μg/mL rhVSIG-3 protein for 1-2 hours at room temperature. During the immobilization, human T cells were isolated using MagCellect Human CD3+ T Cell Isolation Kit (R&D Systems, Minneapolis, MN) following the insert instruction from kit. Isolated human T cells (2×10⁵/well) were added to the plate and cultured for 24 hours at 37° C. in the presence of 5% CO2. Secreted interferon-γ was measured in the cell culture supernatant using QUANTIKINE human interferon-γ ELISA Kit (R&D Systems, Minneapolis, MN). Results are shown in FIG. 5.

The observed ND50 for 973404 (°—open circle) was about 6.7 µg/ml and is expected to depend on the concentration of immobilized rhVSIG3.

Example 4—Fusion Proteins

Figure 6:
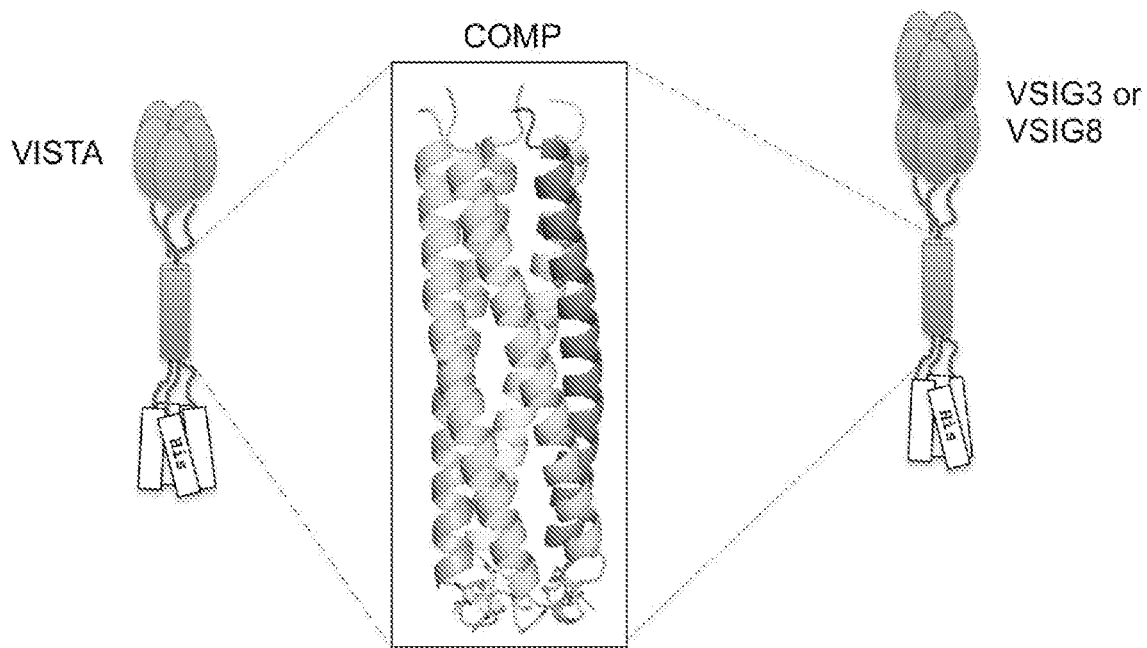
FIG. 6 shows a schematic of extracellular domains from VISTA (left), VSIG3 or VSIG8 (right) fused to the pentameric coiled-coil domain of rat cartilage oligomeric matrix protein (COMP, residues 26-72, middle), followed by a 6×His tag.

As shown schematically in FIG. 6, VISTA, VSIG3, or VSIG8 was fused to the pentameric coiled-coil domain of rat cartilage oligomeric matrix protein (COMP, residues 26-72). Sequences are shown in Table 5 and FIGS. 8A-8C.

Figure 7:
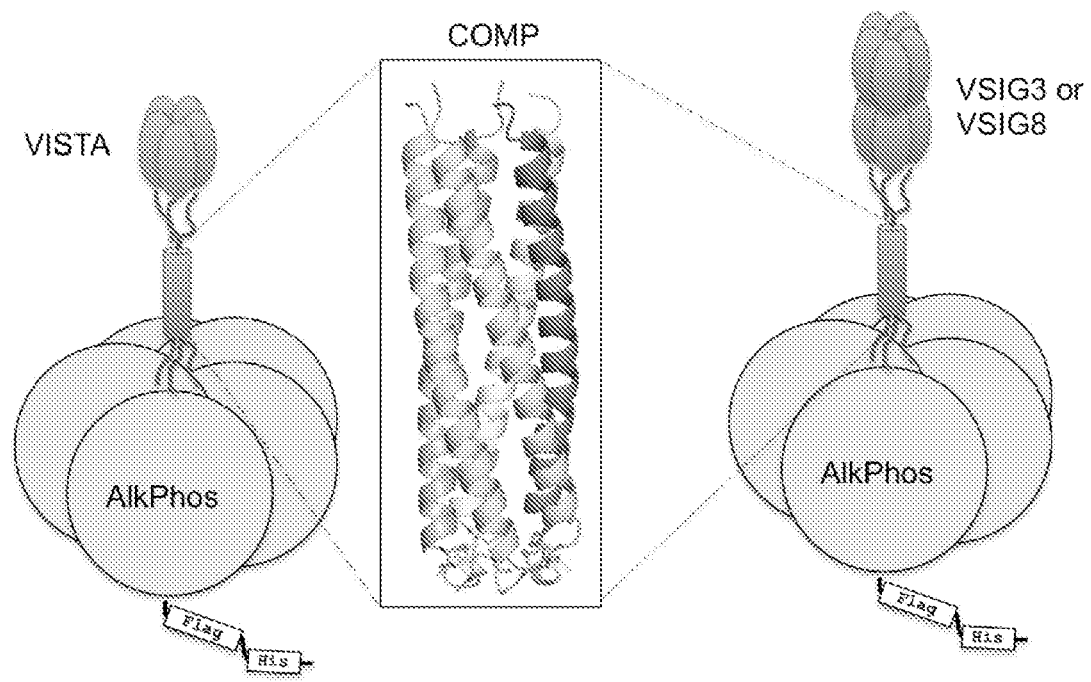
FIG. 7 shows a schematic of VISTA (left), VSIG3 or VSIG8 (right) fused to the pentameric coiled-coil domain of rat cartilage oligomeric matrix protein (COMP, residues 26-72, middle), followed by alkaline phosphatase, Flag, and 6×His tags. Linker residues are shown in green. The alkaline phosphatase can be used for enzymatic detection in the AVEXIS assay, and total protein can be normalized using an anti-poly His antibody.
Figure 9A:
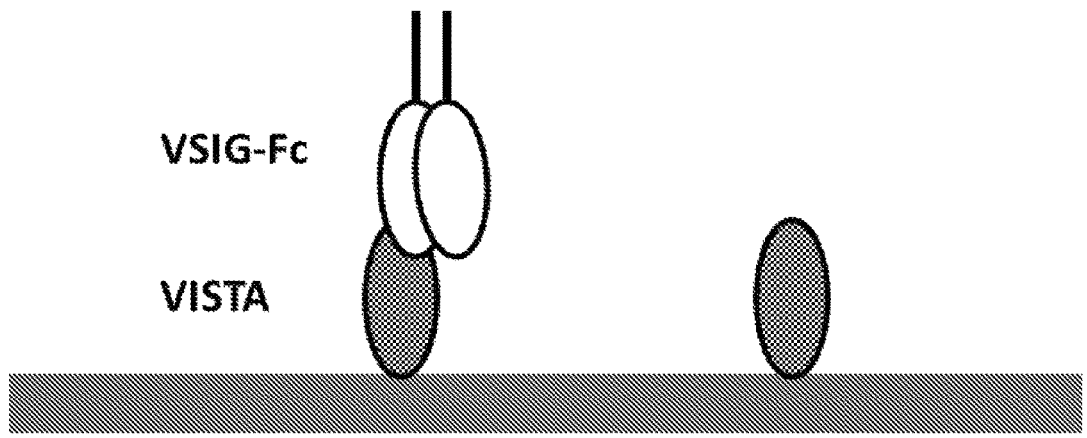
FIG. 9A-FIG. 9D show schematics and quantification of the kinetics and affinity of the VISTA-VSIG3 interaction by surface plasmon resonance (Biacore) using monomeric VISTA and multimeric VISTA-COMP.
Figure 9C:
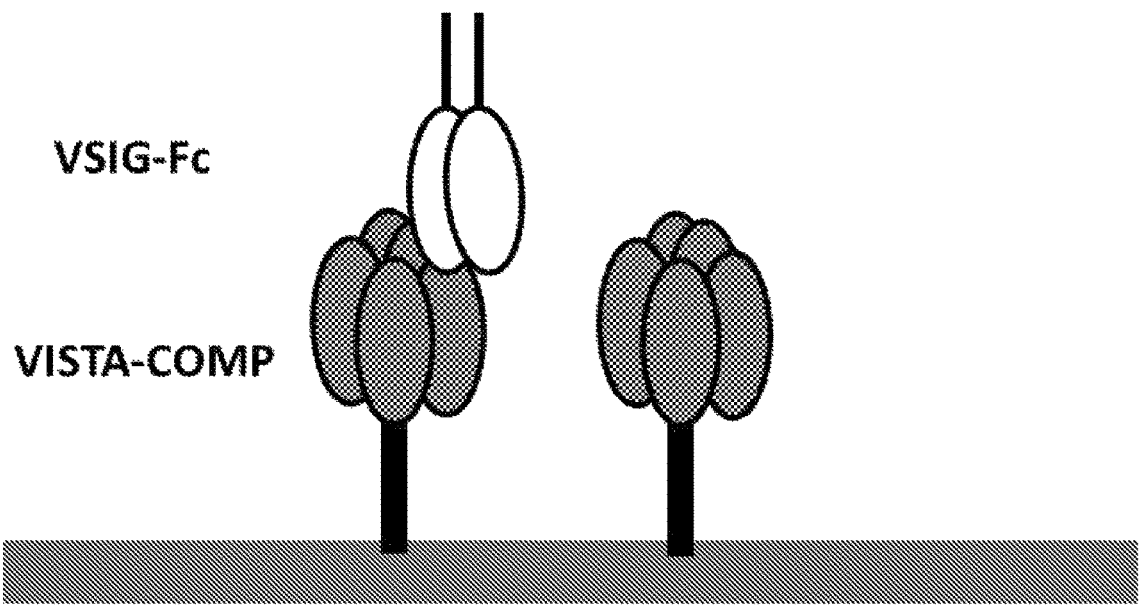
Figure 9B:
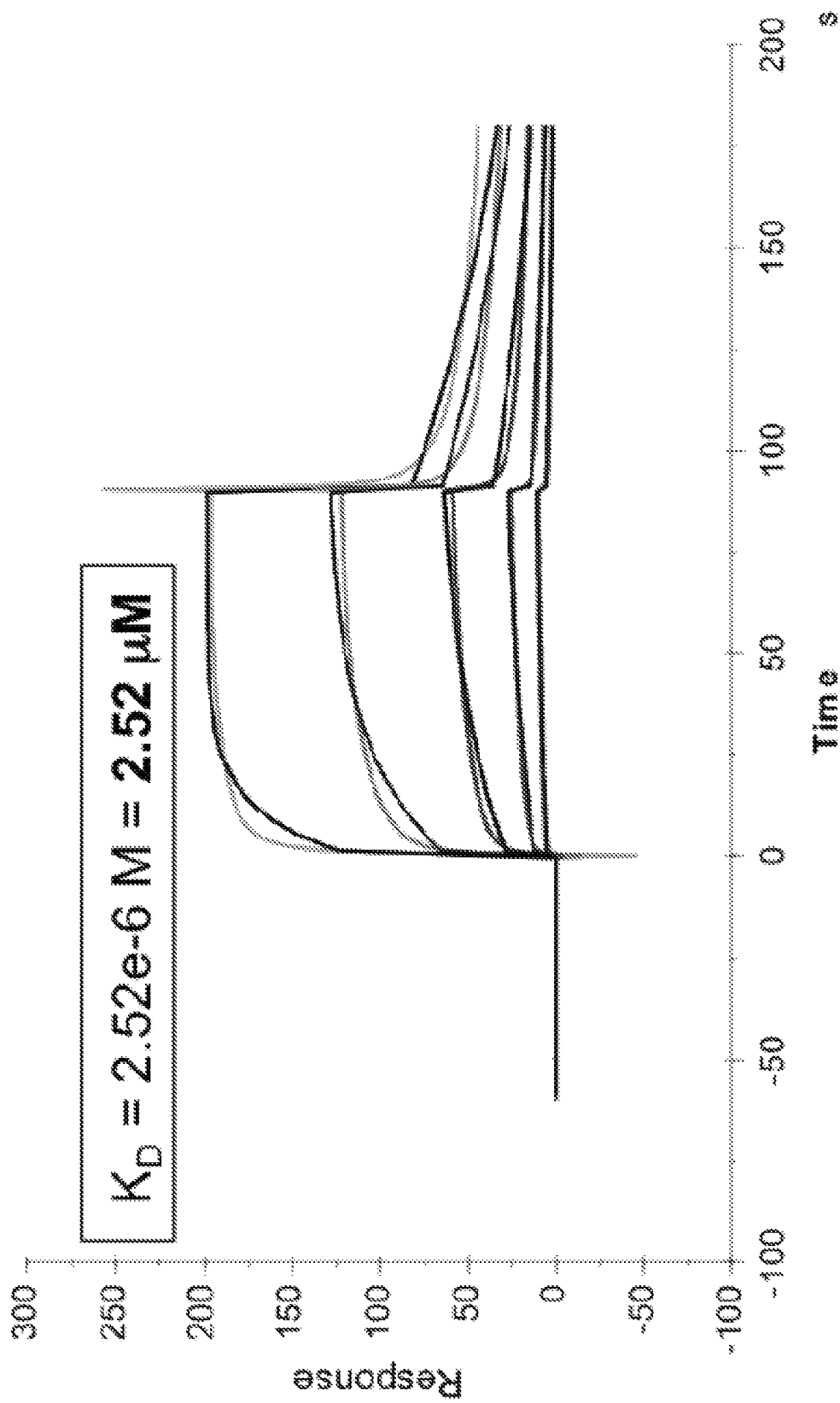
Figure 9D:
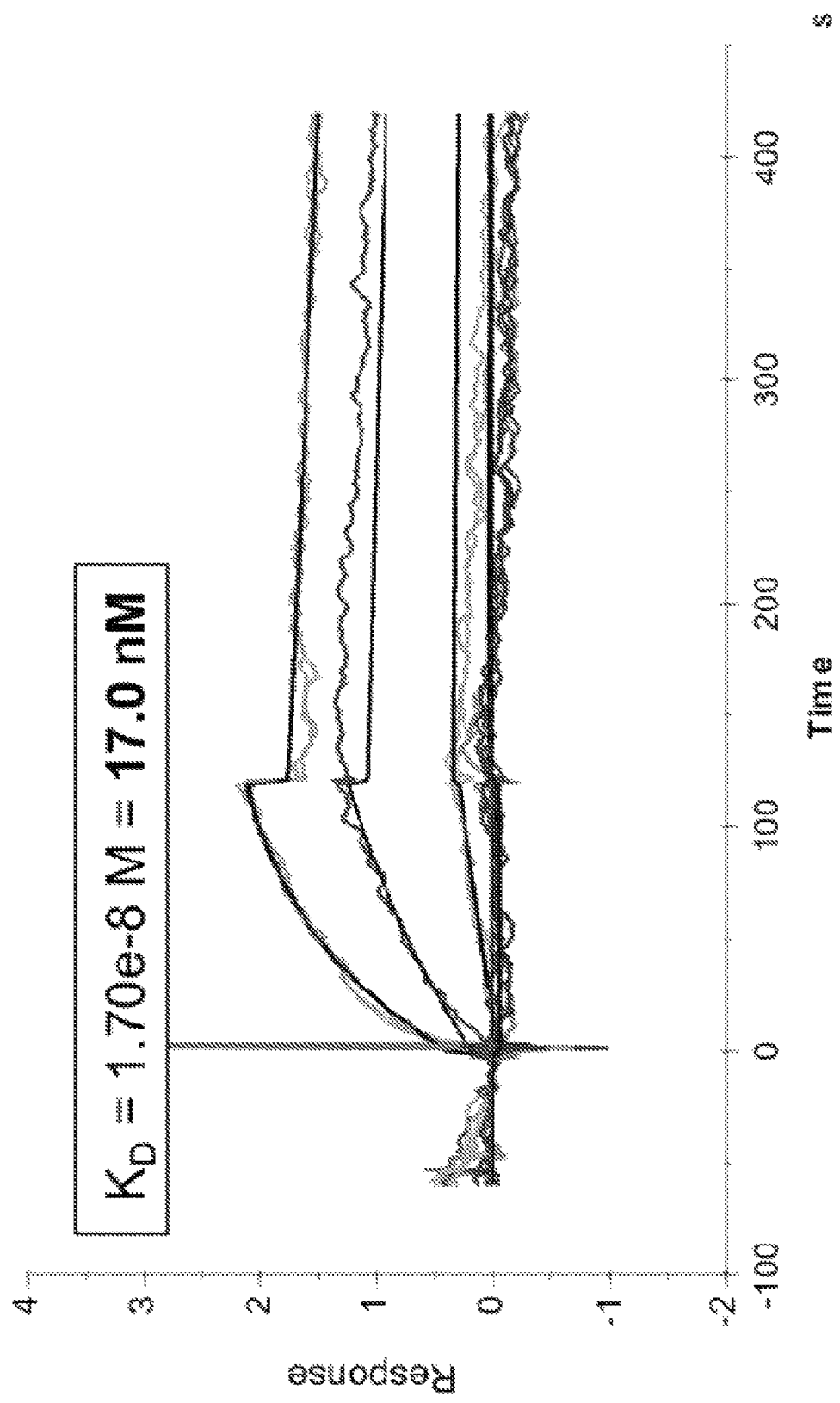

As shown schematically in FIG. 7, VISTA, VSIG3, or VSIG8 was fused to the pentameric coiled-coil domain of rat cartilage oligomeric matrix protein (COMP, residues 26-72), followed by alkaline phosphatase, Flag, and 6×His tags. Linker residues are shown in green. The alkaline phosphatase can be used for enzymatic detection in an avidity-based extracellular interaction screen (AVEXIS) assay, and total protein can be normalized using an anti-poly His antibody. Sequences are shown in Table 5 and FIGS. 8A-8C.

These fusion proteins have a high degree of multimerization and are highly stable resulting from a relative high number of subunits (similar constructs nearly all contain 2-3 subunits instead of 5) and tethering via disulfide bonds.

TABLE 5

| | |
|---|---|
| VISTA(1-195)-COMP-AlkPhos-Flag/His (SEQ ID NO: 7) | MGVPTALEAGSWRWGSLLFALFLAASLGPVAAFKVATPYSLYVCPEGQNVTLTCRLLGPV DKGHDVTFYKTWYRSSRGEVQTCSERRPIRNLTFQDLHLHHGGHQAANTSHDLAQRHGLE SASDHHGNFSITMRNLTLLDSGLYCCLVVEIRHHHSEHRVHGAMELQVQTGKDAPSNCVV YPSSSQESENITAAGSENLYFQGNSGGGSGGGTGGGDLAPQMLRELQETNAALQDVRELL RHRVKEITFLKNTVMECDACGLDRNLPPLAPLGPIIPVEEENPDFWNREAAEALGAAKKL QPAQTAAKNLIIFLGDGMGVSTVTAARILKGQKKDKLGPEIPLAMDRFPYVALSKTYNVD KHVPDSGATATAYLCGVKGNFQTIGLSAAARFNQCNTTRGNEVISVMNRAKKAGKSVGVV TTTRVQHASPAGTYAHTVNRNWYSDADVPASARQEGCQDIATQLISNMDIDVILGGGRKY MFRMGTPDPEYPDDYSQGGTRLDGKNLVQEWLAKRQGARYVWNRTELMQASLDPSVTHLM GLFEPGDMKYEIHRDSTLDPSLMEMTEAALRLLSRNPRGEFLEVEGGRIDHGHHESRAYR ALTETIMFDDAIERAGQLTSEEDTLSLVTADHSHVFSFGGYPLRGSSIFGLAPGKARDRK AYTVLLYGNGPGYVLKDGARPDVTESESGSPEYRQQSAVPLDEETHAGEDVAVFARGPQA HLVHGVQEQTFIAHVMAFAACLEPYTACDLAPPAGTTDDYKDDDDKHHHHHH |
| VISTA(1-195)-COMP-His (SEQ ID NO: 8) | MGVPTALEAGSWRWGSLLFALFLAASLGPVAAFKVATPYSLYVCPEGQNVTLTCRLLGPV DKGHDVTFYKTWYRSSRGEVQTCSERRPIRNLTFQDLHLHHGGHQAANTSHDLAQRHGLE SASDHHGNFSITMRNLTLLDSGLYCCLVVEIRHHHSEHRVHGAMELQVQTGKDAPSNCVV YPSSSQESENITAAGSENLYFQGNSGGGSGGGTGGGDLAPQMLRELQETNAALQDVRELL RHRVKEITFLKNTVMECDACGLDRNLPPLAPLGPHHHHHH |
| VSIG3(1-245)-COMP-AlkPhos-Flag/His (SEQ ID NO: 9) | MTSQRSPLAPLLLLSLHGVAASLEVSESPGSIQVARGQPAVLPCTFTTSAALINLNVIWM VTPLSNANQPEQVILYQGGQMEDGAPREHGRVGFTGTMPATNVSIFINNTQLSDTGTYQC LVNNLPDIGGRNIGVTGLTVLVPPSAPHCQIQGSQDIGSDVILLCSSEEGIPRPTYLWEK LDNTLKLPPTATQDQVQGTVTIRNISALSSGLYQCVASNAIGTSTCLLDLQVISPQPRNI GLIAGSENLYFQGNSGGGSGGGTGGGDLAPQMLRELQETNAALQDVRELLRHRVKEITFL KNTVMECDACGLDRNLPPLAPLGPIIPVEEENPDFWNREAAEALGAAKKLQPAQTAAKNL IIFLGDGMGVSTVTAARILKGQKKDKLGPEIPLAMDRFPYVALSKTYNVDKHVPDSGATA TAYLCGVKGNFQTIGLSAAARFNQCNTTRGNEVISVMNRAKKAGKSVGVVTTTRVQHASP AGTYAHTVNRNWYSDADVPASARQEGCQDIATQLISNMDIDVILGGGRKYMFRMGTPDPE YPDDYSQGGTRLDGKNLVQEWLAKRQGARYVWNRTELMQASLDPSVTHLMGLFEPGDMKY EIHRDSTLDPSLMEMTEAALRLLSRNPRGEFLEVEGGRIDHGHHESRAYRALTETIMFDD AIERAGQLTSEEDTLSLVTADHSHVESEGGYPLRGSSIFGLAPGKARDRKAYTVLLYGNG PGYVLKDGARPDVTESESGSPEYRQQSAVPLDEETHAGEDVAVFARGPQAHLVHGVQEQT FIAHVMAFAACLEPYTACDLAPPAGTTDDYKDDDDKHHHHHH |
| VSIG3(1-245)-COMP-His (SEQ ID NO: 10) | MTSQRSPLAPLLLLSLHGVAASLEVSESPGSIQVARGQPAVLPCTFTTSAALINLNVIWM VTPLSNANQPEQVILYQGGQMFDGAPREHGRVGFTGTMPATNVSIFINNTQLSDTGTYQC LVNNLPDIGGRNIGVTGLTVLVPPSAPHCQIQGSQDIGSDVILLCSSEEGIPRPTYLWEK LDNTLKLPPTATQDQVQGTVTIRNISALSSGLYQCVASNAIGTSTCLLDLQVISPQPRNI GLIAGSENLYFQGNSGGGSGGGTGGGDLAPQMLRELQETNAALQDVRELLRHRVKEITFL KNTVMECDACGLDRNLPPLAPLGPHHHHHH |
| VSIG8(1-263)-COMP-AlkPhos-Flag/His (SEQ ID NO: 11) | MRVGGAFHLLLVCLSPALLSAVRINGDGQEVLYLAEGDNVRLGCPYVLDPEDYGPNGLDI EWMQVNSDPAHHRENVFLSYQDKRINHGSLPHLQQRVRFAASDPSQYDASINLMNLQVSD TATYECRVKKTTMATRKVIVTVQARPAVPMCWTEGHMTYGNDVVLKCYASGGSQPLSYKW AKISGHHYPYRAGSYTSQHSYHSELSYQESFHSSINQGLNNGDLVLKDISRADDGLYQCT VANNVGYSVCVVEVKVSDSRRIGGSENLYFQGNSGGGSGGGTGGGDLAPQMLRELQETNA ALQDVRELLRHRVKEITFLKNTVMECDACGLDRNLPPLAPLGPIIPVEEENPDFWNREAA EALGAAKKLQPAQTAAKNLIIFLGDGMGVSTVTAARILKGQKKDKLGPEIPLAMDRFPYV ALSKTYNVDKHVPDSGATATAYLCGVKGNFQTIGLSAAARFNQCNTTRGNEVISVMNRAK KAGKSVGVVTTTRVQHASPAGTYAHTVNRNWYSDADVPASARQEGCQDIATQLISNMDID VILGGGRKYMFRMGTPDPEYPDDYSQGGTRLDGKNLVQEWLAKRQGARYVWNRTELMQAS LDPSVTHLMGLFEPGDMKYEIHRDSTLDPSLMEMTEAALRLLSRNPRGEFLEVEGGRIDH GHHESRAYRALTETIMFDDAIERAGQLTSEEDTLSLVTADHSHVESEGGYPLRGSSIFGL APGKARDRKAYTVLLYGNGPGYVLKDGARPDVTESESGSPEYRQQSAVPLDEETHAGEDV AVFARGPQAHLVHGVQEQTFIAHVMAFAACLEPYTACDLAPPAGTTDDYKDDDDKHHHHH H |

TABLE 5-continued

| | |
|---|---|
| VSIG8(1-263)-COMP-His<br>(SEQ ID NO: 12) | MRVGGAFHLLLVCLSPALLSAVRINGDGQEVLYLAEGDNVRLGCPYVLDPEDYGPNGLDI<br>EWMQVNSDPAHHRENVFLSYQDKRINHGSLPHLQQRVRFAASDPSQYDASINLMNLQVSD<br>TATYECRVKKTTMATRKVIVTVQARPAVPMCWTEGHMTYGNDVVLKCYASGGSQPLSYKW<br>AKISGHHYPYRAGSYTSQHSYHSELSYQESFHSSINQGLNNGDLVLKDISRADDGLYQCT<br>VANNVGYSVCVVEVKVSDSRRIGGSENLYFQGNSGGGSGGGTGGGDLAPQMLRELQETNA<br>ALQDVRELLRHRVKEITFLKNTVMECDACGLDRNLPPLAPLGPHHHHHH |

Example 5—Quantification of the Kinetics and Affinity of the VISTA-VSIG3 Interaction by Surface Plasmon Resonance VISTA or VISTA-COMP (each prepared as described in Example 4) was covalently immobilized to the surface of a CM5 chip (GE Healthcare, US) using an anti-poly His antibody. Dilutions of VSIG3 Fc-fusion were then flowed over the surface at concentration ranging between 0.2 nM and 20 μM and the double reference subtracted data fit to a 1:1 Langmuir binding model with Biacore T200 Evaluation Software version 3.1

As shown in FIG. 9, multimeric VISTA-COMP has an approximately 150-fold higher affinity for VSIG3-Fc (~17 nM) than for monomeric VISTA (~2.5 μM). This increase is largely due to an increase in the off-rate.

Example 6—Avidity-Based Extracellular Interaction Screens

Figure 10:
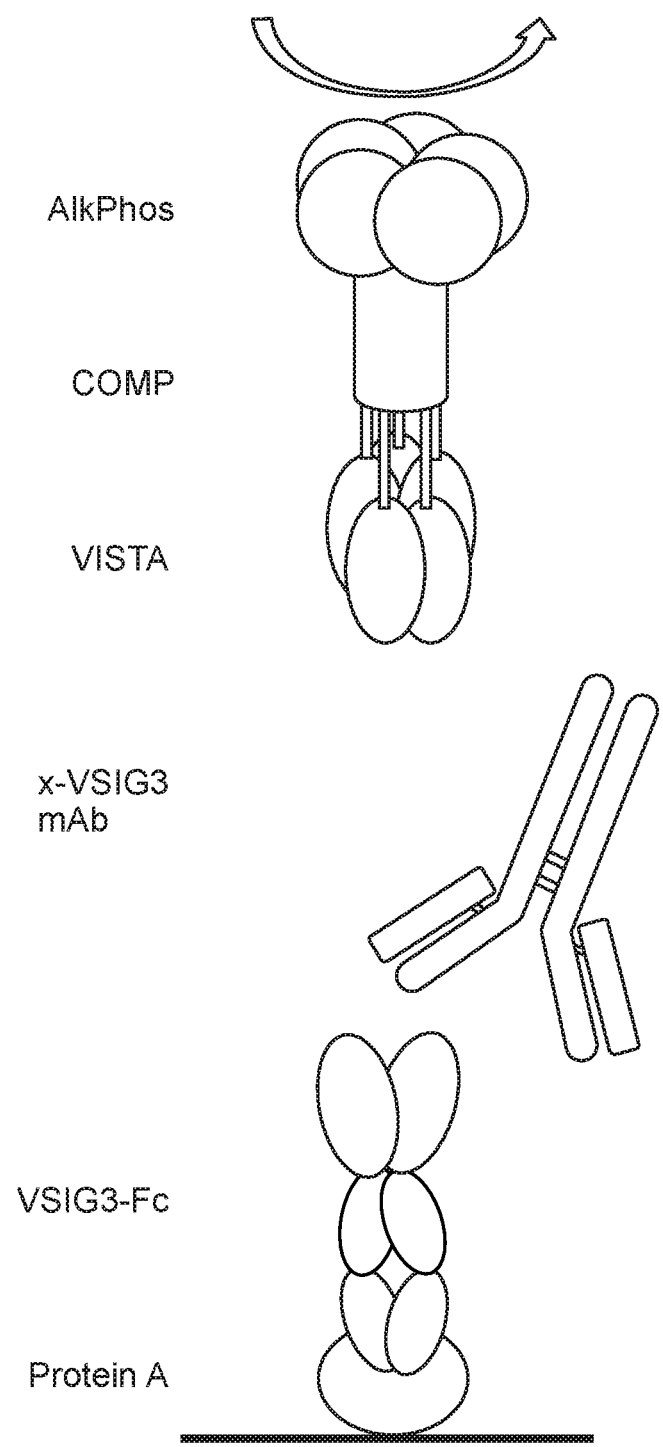
FIG. 10 shows a schematic of an exemplary avidity-based extracellular interaction screen (AVEXIS) modified to test for blocking antibodies against VSIG3. VSIG3-Fc was coated on Protein A plates, blocked, and incubated with individual mAbs from a panel of monoclonal antibodies against VSIG3. The VISTA ectodomain (ECD) coupled to a pentamerizing rat cartilage oligomeric matrix protein (COMP) helix and alkaline phosphatase was added, and the interaction between VSIG3 and VISTA was measured based on alkaline phosphatase activity.

The avidity-based extracellular interaction screen (AVEXIS) was modified to screen for antibodies against VSIG3 that block the interaction between recombinant human VSIG3 (rhVSIG3) and VISTA. A schematic of the assay is shown in FIG. 10. Briefly, purified recombinant Fc-fusion proteins (that is, bait proteins including, for example VSIG3-Fc) were captured individually on protein A-coated plates (Thermo Fisher Scientific, Waltham, MA) and subsequently blocked with 1% BSA blocking buffer. After capturing VSIG3-Fc bait on protein A coated plates, wells were incubated individually with a monoclonal antibody against VSIG3. Conditioned media containing the oligomeric prey protein fused to the COMP helical oligomer and alkaline phosphatase was then added, incubated, and washed, and the interaction was quantitatively measured by detection of alkaline phosphatase activity using the BLUE-PHOS reagent (KPL/Sera Care, Milford, MA).

Figure 11:
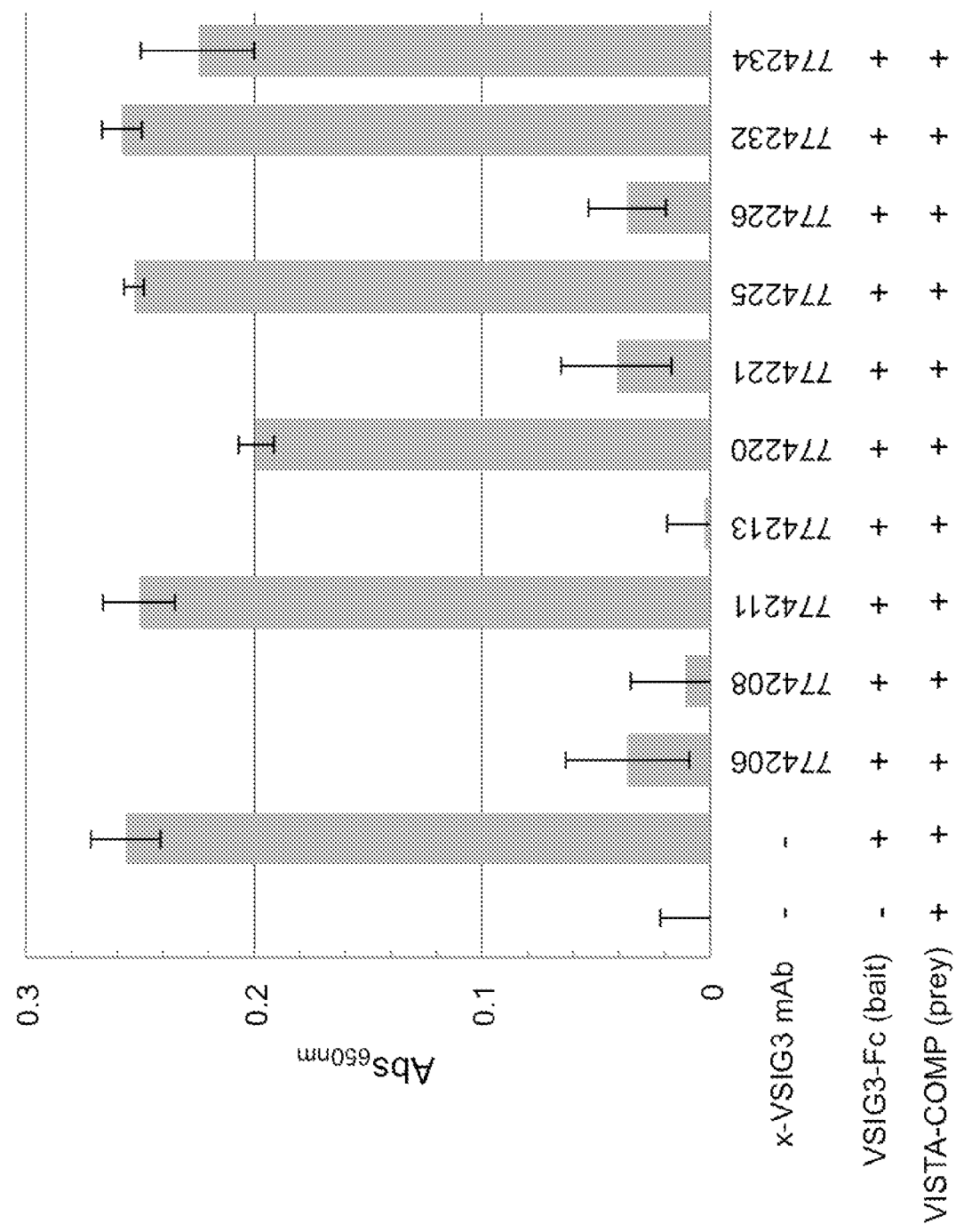
FIG. 11 shows exemplary results from an AVEXIS assay screening for antibodies against VSIG3 that block the interaction between VSIG3 and VISTA measured using Blue-Phos reagent. Results were quantified using an absorbance of 650 nm with background subtracted. Antibodies tested are mouse monoclonals raised against rhVSIG3 (1-245). Shown is the mean absorbance at 650 nm±standard deviation of at least three replicates. Antibody clones 774206 and 774208, which block to near background levels, are used as positive controls in FIG. 12-FIG. 14.
Figure 12:
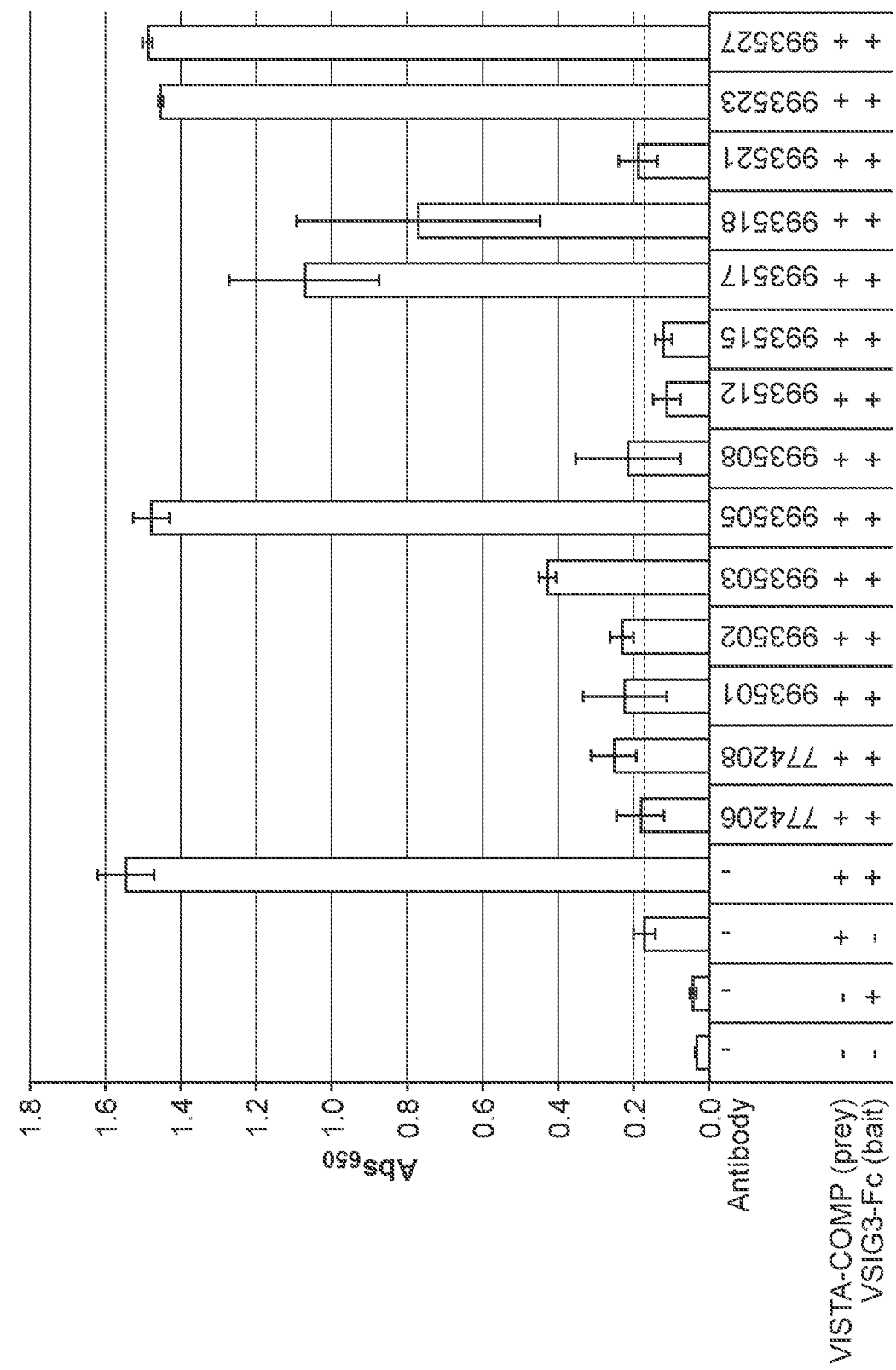
FIG. 12 shows exemplary results from an AVEXIS assay screening for antibodies against VSIG3 that block the interaction between VSIG3 and VISTA measured using Blue-Phos reagent. Results were quantified using an absorbance of 650 nm with background subtracted. Antibodies tested are mouse monoclonals raised against rhVSIG3 (1-245). Shown is the mean absorbance at 650 nm±standard deviation of at least three replicates. Antibody clones 774206 and 774208 were used as positive controls, and the background is shown by the red dashed line.
Figure 13:
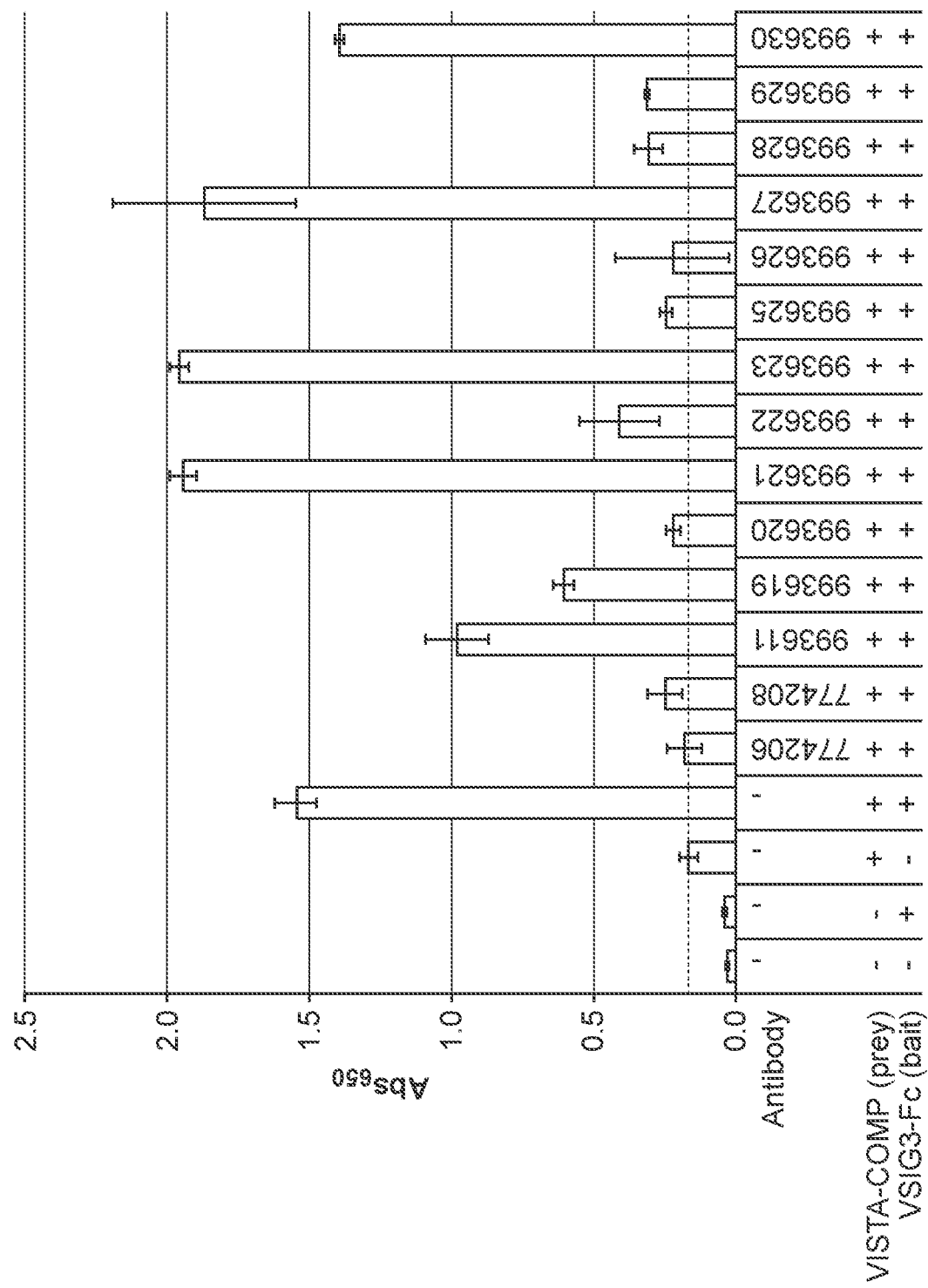
FIG. 13 shows exemplary results from an AVEXIS assay screening for antibodies against VSIG3 that block the interaction between VSIG3 and VISTA measured using Blue-Phos reagent. Results were quantified using an absorbance of 650 nm with background subtracted. Antibodies tested are mouse monoclonals raised against rhVSIG3 (1-245). Shown is the mean absorbance at 650 nm±standard deviation of at least three replicates. Antibody clones 774206 and 774208 were used as positive controls, and the background is shown by the red dashed line.
Figure 14:
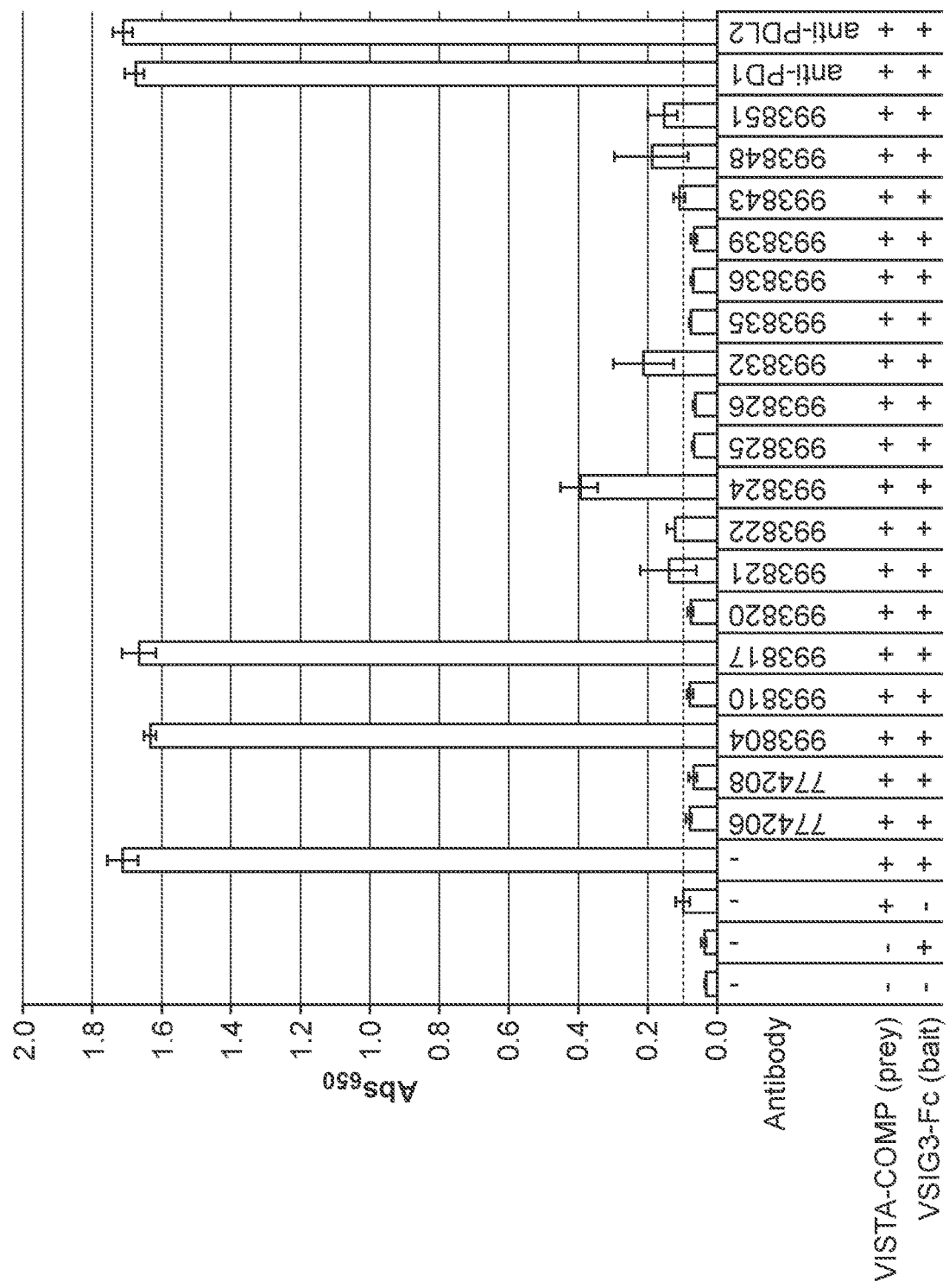
FIG. 14 shows exemplary results from an AVEXIS assay screening for antibodies against VSIG3 that block the interaction between VSIG3 and VISTA measured using Blue-Phos reagent. Results were quantified using an absorbance of 650 nm with background subtracted. Antibodies tested are mouse monoclonals raised against rhVSIG3 (1-245). Shown is the mean absorbance at 650 nm±standard deviation of at least three replicates. Antibody clones 774206 and 774208 were used as positive controls, and the background is shown by the red dashed line. Antibodies against PD-1 and PD-L2 were used as negative controls and show no disruption of the interaction.

Rat and mouse monoclonal antibodies recognizing human VSIG3 were generated and tested for their ability to block a VSIG3-VISTA interaction. AVEXIS assay screening for antibody blockade of the VSIG3-VISTA interaction was conducted as described above. Briefly, the bait protein, VSIG3-Fc, was captured on Protein A coated plates and blocked without or with antibodies at 10 μg/mL. Antibodies from clones 774206 and 74208 were found to block the VISTA-VSIG3 interaction to near background levels, as shown in FIG. 11, and were used as a positive control in FIG. 12, FIG. 13, and FIG. 14. The prey protein, multimeric VISTA with alkaline phosphatase, was incubated in the presence of anti-VSIG3 antibodies. After washing, the interaction between VSIG3 and VISTA was measured using alkaline phosphatase substrate and quantified by measuring the absorbance at 650 nm. Results are shown in FIG. 12, FIG. 13, and FIG. 14 and are summarized in Table 6.

Example 7—VSIG3-COMP Blocks T Cell Proliferation and Activation

Combinations of anti-human CD3 (1-5 μg/ml), and rhVSIG3 (10-25 μg/mL), or VSIG3-COMP (10-25 μg/ml) were coated onto 96 well plates, overnight, at 4° C. Plates were washed with PBS. CD3+ T cells were negatively selected from human PBMC using a CD3+ T cell isolation kit (R&D Systems, MAGH101), labeled with Cell Trace Violet proliferation dye (Life Technologies per manufacturers specifications), and added to the wells ($5 \times 10^4$–$2 \times 10^5$ cells per well) in 200 μl RPMI+10% human AB serum. Plates were incubated at 37° C. for 4-6 days, then cells were harvested, and CD25 expression and cell proliferation were analyzed by flow cytometry. Results are shown in FIG. 15.

As shown in FIG. 15, anti-CD3 induced proliferation of CD4+ human T cells (upper left) was partially inhibited when cells were cultured in the presence of rhVSIG3, and completely inhibited in the presence of VSIG3-COMP (left column dot plots). CD25 expression as another indication of T cell activation was similarly inhibited in the presence of rhVSIG3 or VSIG3-COMP (right column dot plots). These results indicate that multimerized VSIG3 is able to effect T cell activation and proliferation more strongly than rhVSIG3.

Figure 16A:
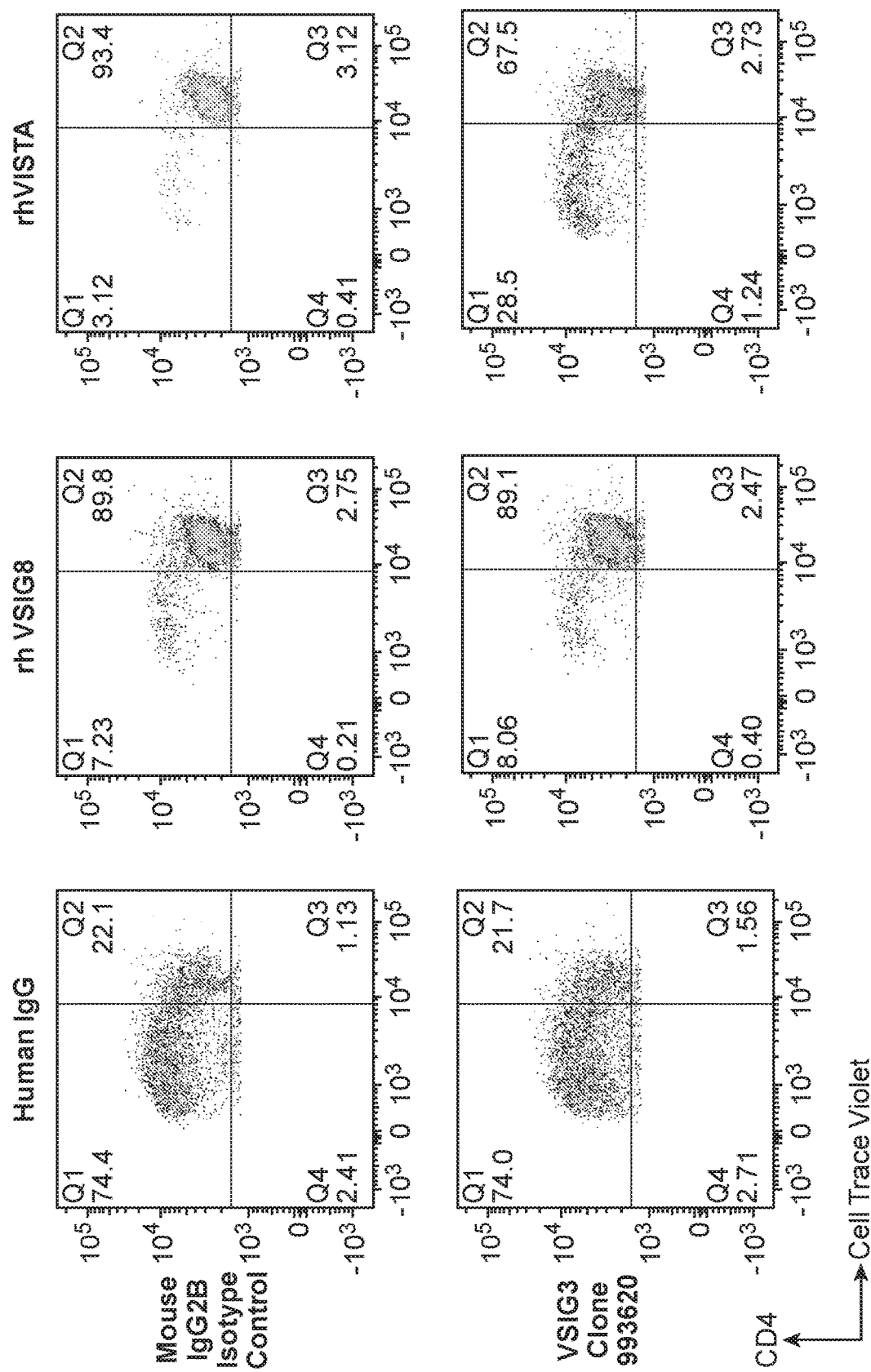
FIG. 16A shows rhVISTA can inhibit anti-CD3-induced proliferation of normal human peripheral blood T cells, and this inhibition can be reversed by anti-human VSIG3 antibody (993620). Recombinant human VSIG8 (rhVSIG8) protein can also inhibit anti-CD3-induced proliferation, but a VSIG3 specific antibody does not affect this inhibition.
Figure 16B:
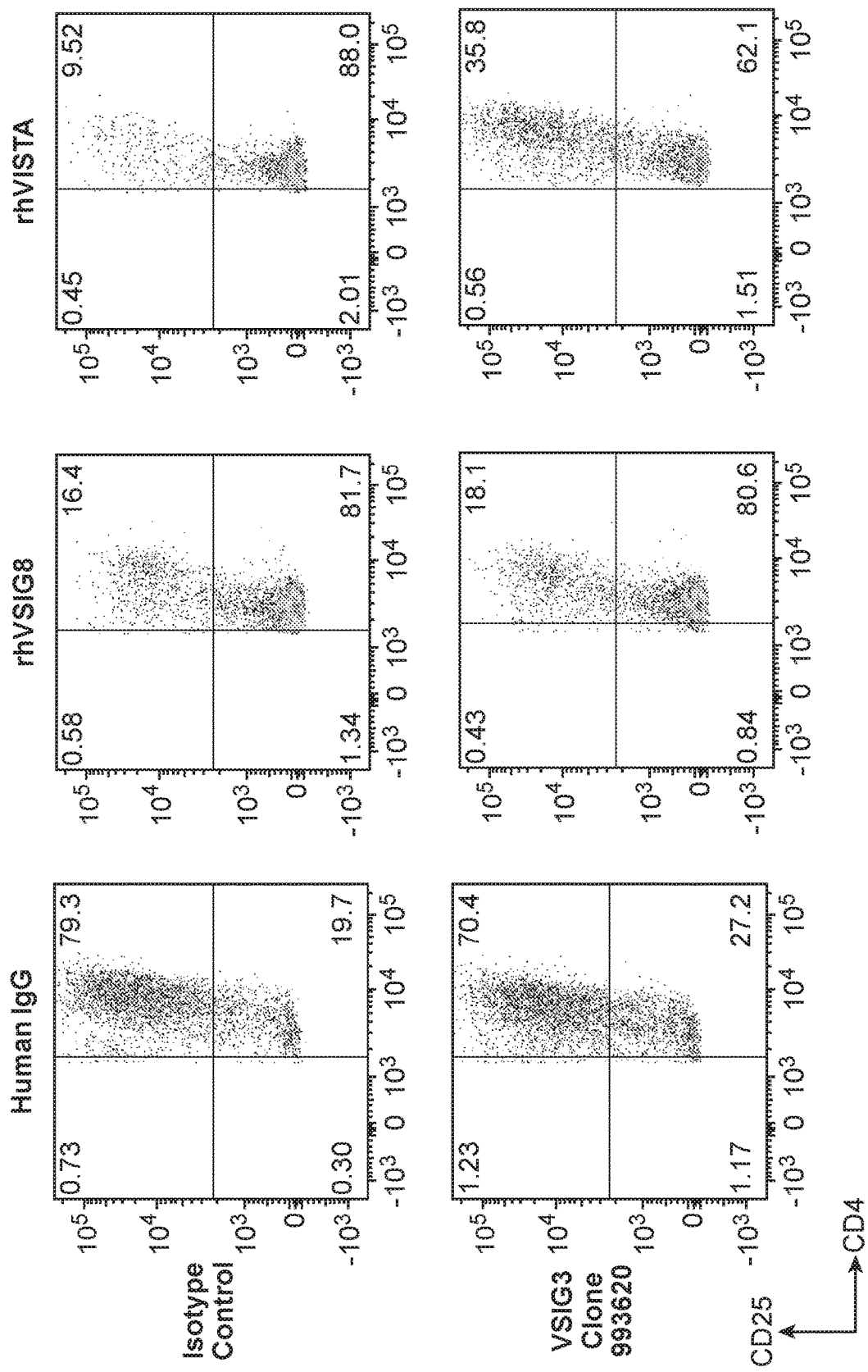
FIG. 16B shows rhVISTA can inhibit anti-CD3-induced CD25 expression on normal human peripheral blood T cells, and this inhibition can be reversed by anti-human VSIG3 antibody (993620). rhVSIG8 protein can also inhibit anti-CD3-induced CD25 expression, but a VSIG3 specific antibody does not affect this inhibition.

Example 8—VSIG3 Blocking Antibodies Restore VISTA-Induced Inhibition of T Cell Proliferation and Activation Combinations of anti-human CD3 (1-5 μg/ml) and rhVSIG8 (10-25 μg/ml) or rhVISTA (10-25 μg/ml) were coated onto 96 well plates, by incubating overnight, at 4° C. Plates were washed with PBS and blocked with 2.5% Human AB serum (Innovative Research) in PBS for 30 minutes. Soluble anti-human VSIG3 antibodies, 993620 or 973404 (1-10 μg/ml), were then added to the appropriate wells. CD3+ T cells were negatively selected from human PBMC using a CD3+ T cell isolation kit (R&D Systems, MAGH101) labeled with Cell Trace Violet proliferation dye (Life Technologies per manufacturers specifications), and added to the wells ($5 \times 10^4$-$2 \times 10^5$ cells per well) in 200 μL of RPMI+10% human AB serum. Plates were incubated at 37° C. for 3-6 days, then cells were harvested, and proliferation/cell activation was analyzed by flow cytometry. Results for antibody 993620 are shown in FIG. 16A and FIG. 16B. Results for antibody 973404 are shown in FIG. 16C.

As shown in FIG. 16A, anti-CD3 induced proliferation of CD4+ human T cells (upper left plot), as evidenced by dilution of Cell Tracer Violet dye with each cell division, decrease in fluorescence intensity, and movement of cell populations from the upper right quadrant to the upper left quadrant. Culture with either rhVSIG8 or rhVISTA inhibited CD3-induced proliferation, as shown by maintenance of cells in the upper right quadrant (top row, middle and right plots). While addition of anti-human VSIG3 antibody clone 993620 had no effect on inhibition of proliferation by rhVSIG8, the inhibition of proliferation by rhVISTA protein was partially reversed (bottom right). These results indicate that anti-VSIG3 monoclonal antibody 993620 can block rhVISTA-induced inhibition of T cell proliferation. Furthermore, the addition of anti-human VSIG3 antibody clone 993620 partially restored CD3-induced T cell activation as measured by CD25 expression on T cells cultured with rhVISTA but not rhVSIG8 (FIG. 16B, bottom row).

Figure 16C:
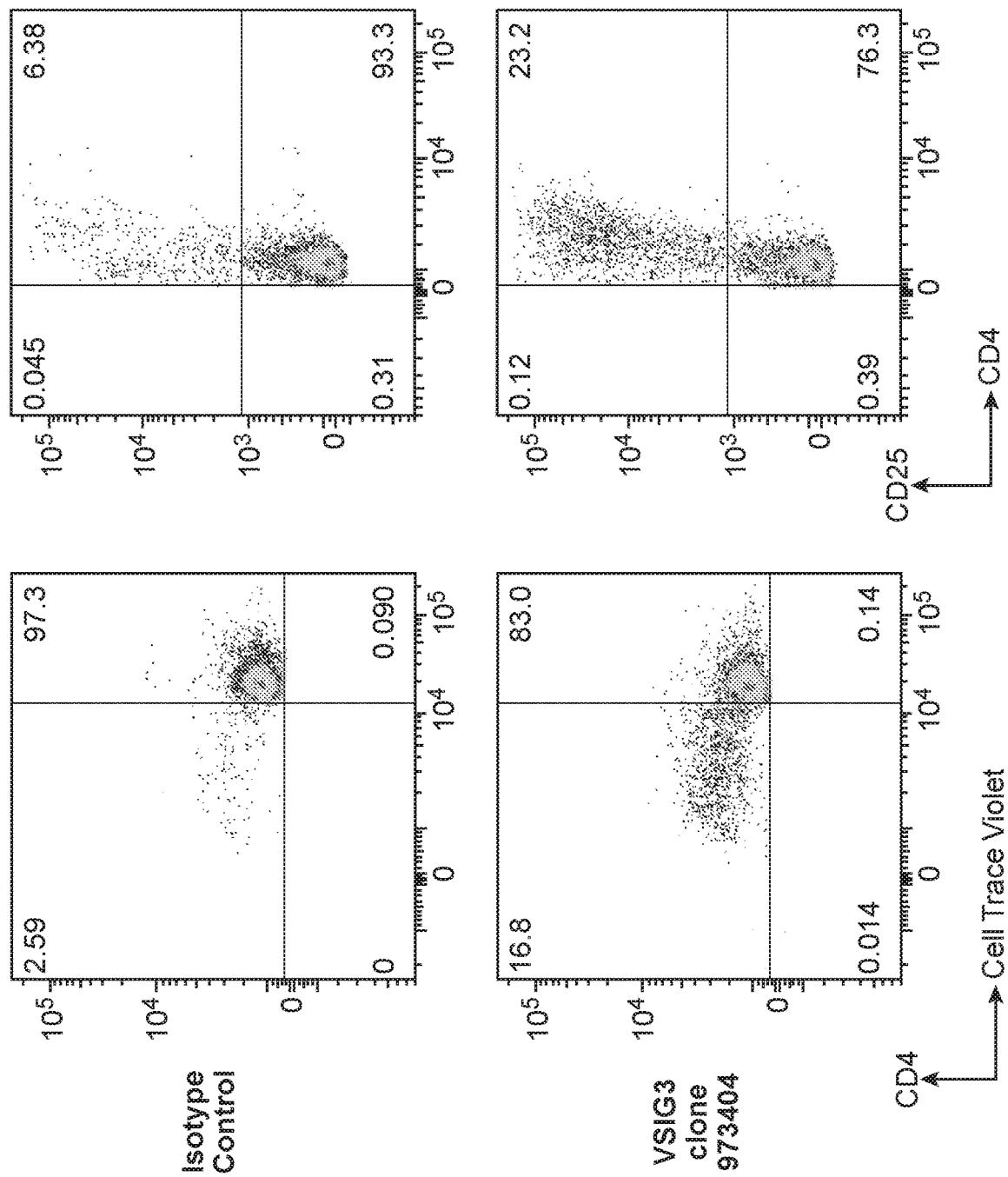
FIG. 16C shows rhVISTA can inhibit anti-CD3-induced CD25 upregulation and proliferation of normal human peripheral blood T cells. While this inhibition was not affected by the addition of isotype control antibody (top left), proliferation (left column) was partially restored with the addition of VSIG3 monoclonal antibody 973404. CD25 expression (right column), another indication of T cell activation, was similarly inhibited in the presence of rhVISTA, and this inhibition was partially reversed with the addition of VSIG3 antibody.

As shown in FIG. 16C, anti-CD3 induced proliferation of CD4⁺ human T cells was inhibited when cells were cultured in the presence of rhVISTA. While this inhibition was not affected by the addition of isotype control antibody (top left), proliferation was partially restored with the addition of VSIG3 monoclonal antibody 973404 (left dot plots). CD25 expression, another indication of T cell activation, was similarly inhibited in the presence of rhVISTA, and this was partially reversed with the addition of VSIG3 antibody (right dot plots). These data indicate that an anti-VSIG3 blocking antibody can block rhVISTA-induced inhibition of T cell proliferation.

TABLE 6

Screen of anti-VSIG3 antibodies using the AVEXIS assay

| Antibody clone # | Immunogen | Antibody type | Blocking VSIG3 - VISTA interaction |
|---|---|---|---|
| 993501 | rhVSIG3 (1-245) | Mouse monoclonal | >95% blocking |
| 993502 | rhVSIG3 (1-245) | Mouse monoclonal | >95% blocking |
| 993503 | rhVSIG3 (1-245) | Mouse monoclonal | ~80% blocking |
| 993505 | rhVSIG3 (1-245) | Mouse monoclonal | No blocking |
| 993508 | rhVSIG3 (1-245) | Mouse monoclonal | >95% blocking |
| 993512 | rhVSIG3 (1-245) | Mouse monoclonal | >95% blocking |
| 993515 | rhVSIG3 (1-245) | Mouse monoclonal | >95% blocking |
| 993517 | rhVSIG3 (1-245) | Mouse monoclonal | ~30% blocking |
| 993518 | rhVSIG3 (1-245) | Mouse monoclonal | ~50% blocking |
| 993521 | rhVSIG3 (1-245) | Mouse monoclonal | >95% blocking |
| 993523 | rhVSIG3 (1-245) | Mouse monoclonal | No blocking |
| 993527 | rhVSIG3 (1-245) | Mouse monoclonal | No blocking |
| 993611 | rhVSIG3 (1-245) | Mouse monoclonal | ~80% blocking |
| 993619 | rhVSIG3 (1-245) | Mouse monoclonal | >90% blocking |
| 993620 | rhVSIG3 (1-245) | Mouse monoclonal | >95% blocking |
| 993621 | rhVSIG3 (1-245) | Mouse monoclonal | No blocking |
| 993622 | rhVSIG3 (1-245) | Mouse monoclonal | >95% blocking |
| 993623 | rhVSIG3 (1-245) | Mouse monoclonal | No blocking |
| 993625 | rhVSIG3 (1-245) | Mouse monoclonal | >95% blocking |
| 993626 | rhVSIG3 (1-245) | Mouse monoclonal | >95% blocking |
| 993627 | rhVSIG3 (1-245) | Mouse monoclonal | ~20% blocking |
| 993628 | rhVSIG3 (1-245) | Mouse monoclonal | >95% blocking |
| 993629 | rhVSIG3 (1-245) | Mouse monoclonal | >95% blocking |
| 993630 | rhVSIG3 (1-245) | Mouse monoclonal | ~60% blocking |
| 993804 | rhVSIG3 (1-245) | Rat monoclonal | No blocking |
| 993810 | rhVSIG3 (1-245) | Rat monoclonal | >95% blocking |
| 993817 | rhVSIG3 (1-245) | Rat monoclonal | No blocking |
| 993820 | rhVSIG3 (1-245) | Rat monoclonal | >95% blocking |
| 993821 | rhVSIG3 (1-245) | Rat monoclonal | >95% blocking |
| 993822 | rhVSIG3 (1-245) | Rat monoclonal | >95% blocking |
| 993824 | rhVSIG3 (1-245) | Rat monoclonal | ~80% blocking |
| 993825 | rhVSIG3 (1-245) | Rat monoclonal | >95% blocking |
| 993826 | rhVSIG3 (1-245) | Rat monoclonal | >95% blocking |
| 993832 | rhVSIG3 (1-245) | Rat monoclonal | >90% blocking |
| 993835 | rhVSIG3 (1-245) | Rat monoclonal | >95% blocking |
| 993836 | rhVSIG3 (1-245) | Rat monoclonal | >95% blocking |
| 993839 | rhVSIG3 (1-245) | Rat monoclonal | >95% blocking |
| 993843 | rhVSIG3 (1-245) | Rat monoclonal | >95% blocking |
| 993848 | rhVSIG3 (1-245) | Rat monoclonal | >90% blocking |
| 993851 | rhVSIG3 (1-245) | Rat monoclonal | >95% blocking |

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the embodiments.

What is claimed is:

1. A method for modulating the interaction of VISTA and VSIG3, the method comprising introducing a compound that modulates the interaction of VISTA and VSIG3, wherein the compound comprises an anti-VSIG3 antibody or antigen binding fragment thereof, and wherein the anti-VSIG3 antibody or antigen binding fragment thereof comprises a heavy chain variable region comprising a CDR1 comprising SEQ ID NO: 17, a CDR2 comprising SEQ ID NO: 18, and a CDR3 comprising SEQ ID NO: 19 and a light chain variable region comprising a CDR1 comprising SEQ ID NO: 20, a CDR2 comprising SEQ ID NO: 21, and a CDR3 comprising SEQ ID NO: 22.

2. The method of claim 1, wherein the anti-VSIG3 antibody or antigen binding fragment thereof blocks a VSIG3-VISTA interaction.

3. The method of claim 1, wherein the anti-VSIG3 antibody or antigen binding fragment thereof comprise an antigen-binding fragment comprising a Fab fragment, a Fab' fragment, a F(ab)₂ fragment, or a Fv fragment, or a combination thereof.

4. The method of claim 1, wherein the anti-VSIG3 antibody or antigen binding fragment thereof comprises a fusion protein.

5. The method of claim 4, wherein the fusion protein comprises an Fc domain, a cartilage oligomeric matrix protein (COMP), or a linker domain.

6. The method of claim 1, wherein the anti-VSIG3 antibody or antigen binding fragment thereof comprises:
a heavy chain variable region comprising SEQ ID NO: 15, or SEQ ID NO: 15 having one, two, three, four, five, or six amino acid substitutions thereof; or
a light chain variable region comprising SEQ ID NO: 16, or SEQ ID NO: 16 having one, two, three, four, five, or six amino acid substitutions thereof; or
a light chain variable region comprising SEQ ID NO: 16, or SEQ ID NO: 16 having one, two, three, four, five, or six amino acid substitutions thereof, and a heavy chain variable region comprising SEQ ID NO: 15, or SEQ ID NO: 15 having one, two, three, four, five, or six amino acid substitutions thereof.

7. The method of claim 1, wherein the anti-VSIG3 antibody or antigen binding fragment comprises a humanized antibody.

8. The method of claim 1, wherein the anti-VSIG3 antibody or antigen binding fragment thereof comprises a chimeric antibody.

9. The method of claim 1, wherein the anti-VSIG3 antibody or antigen binding fragment thereof is detectably labelled.

10. A method to identify the presence or absence of a VSIG3 protein in a sample, the method comprising contacting the sample with an anti-VSIG3 antibody or antigen binding fragment thereof, wherein the anti-VSIG3 antibody or antigen binding fragment thereof comprises a heavy chain variable region comprising a CDR1 comprising SEQ ID NO: 17, a CDR2 comprising SEQ ID NO: 18, and a CDR3 comprising SEQ ID NO: 19 and a light chain variable region comprising a CDR1 comprising SEQ ID NO: 20, a CDR2 comprising SEQ ID NO: 21, and a CDR3 comprising SEQ ID NO: 22.

11. The method of claim 10, wherein the sample comprises a patient sample.

12. The method of claim 10, wherein the sample comprises a mammalian cancer cell.

13. A method to determine the level of expression of a VSIG3 protein in a cell, the method comprising contacting the cell with an anti-VSIG3 antibody or antigen binding fragment thereof, wherein the anti-VSIG3 antibody or antigen binding fragment thereof comprises a heavy chain variable region comprising a CDR1 comprising SEQ ID NO: 17, a CDR2 comprising SEQ ID NO: 18, and a CDR3 comprising SEQ ID NO: 19 and a light chain variable region comprising a CDR1 comprising SEQ ID NO: 20, a CDR2 comprising SEQ ID NO: 21, and a CDR3 comprising SEQ ID NO: 22.

14. The method of claim 10, wherein the anti-VSIG3 antibody or antigen binding fragment thereof comprises:
   a heavy chain variable region comprising SEQ ID NO: 15, or SEQ ID NO: 15 having one, two, three, four, five, or six amino acid substitutions thereof; or
   a light chain variable region comprising SEQ ID NO: 16, or SEQ ID NO: 16 having one, two, three, four, five, or six amino acid substitutions thereof; or
   a light chain variable region comprising SEQ ID NO: 16, or SEQ ID NO: 16 having one, two, three, four, five, or six amino acid substitutions thereof, and a heavy chain variable region comprising SEQ ID NO: 15, or SEQ ID NO: 15 having one, two, three, four, five, or six amino acid substitutions thereof.

15. The method of claim 10, wherein the anti-VSIG3 antibody or antigen binding fragment thereof comprise an antigen-binding fragment comprising a Fab fragment, a Fab' fragment, a F(ab)2 fragment, or a Fv fragment, or a combination thereof.

16. The method of claim 10, wherein the anti-VSIG3 antibody or antigen binding fragment thereof is detectably labelled.

17. The method of claim 13, wherein the anti-VSIG3 antibody or antigen binding fragment thereof comprises:
   a heavy chain variable region comprising SEQ ID NO: 15, or SEQ ID NO: 15 having one, two, three, four, five, or six amino acid substitutions thereof; or
   a light chain variable region comprising SEQ ID NO: 16, or SEQ ID NO: 16 having one, two, three, four, five, or six amino acid substitutions thereof; or
   a light chain variable region comprising SEQ ID NO: 16, or SEQ ID NO: 16 having one, two, three, four, five, or six amino acid substitutions thereof, and a heavy chain variable region comprising SEQ ID NO: 15, or SEQ ID NO: 15 having one, two, three, four, five, or six amino acid substitutions thereof.

18. The method of claim 13, wherein the anti-VSIG3 antibody or antigen binding fragment thereof comprise an antigen-binding fragment comprising a Fab fragment, a Fab' fragment, a F(ab)2 fragment, or a Fv fragment, or a combination thereof.

19. The method of claim 13, wherein the anti-VSIG3 antibody or antigen binding fragment thereof is detectably labelled.

20. The method of claim 13, wherein the anti-VSIG3 antibody or antigen binding fragment comprises a fusion protein.

* * * * *

SEQUENCE LISTING

<160> NUMBER OF SEQ ID NOS: 22

<210> SEQ ID NO 1
<211> LENGTH: 431
<212> TYPE: PRT
<213> ORGANISM: homo sapiens

<400> SEQUENCE: 1

Met Thr Ser Gln Arg Ser Pro Leu Ala Pro Leu Leu Leu Ser Leu
1               5                   10                  15

His Gly Val Ala Ala Ser Leu Glu Val Ser Glu Ser Pro Gly Ser Ile
            20                  25                  30

Gln Val Ala Arg Gly Gln Pro Ala Val Leu Pro Cys Thr Phe Thr Thr
        35                  40                  45

Ser Ala Ala Leu Ile Asn Leu Asn Val Ile Trp Met Val Thr Pro Leu
    50                  55                  60

Ser Asn Ala Asn Gln Pro Glu Gln Val Ile Leu Tyr Gln Gly Gly Gln
65                  70                  75                  80

Met Phe Asp Gly Ala Pro Arg Phe His Gly Arg Val Gly Phe Thr Gly
                85                  90                  95

Thr Met Pro Ala Thr Asn Val Ser Ile Phe Ile Asn Asn Thr Gln Leu

```
                100                 105                 110
Ser Asp Thr Gly Thr Tyr Gln Cys Leu Val Asn Asn Leu Pro Asp Ile
            115                 120                 125

Gly Gly Arg Asn Ile Gly Val Thr Gly Leu Thr Val Leu Val Pro Pro
130                 135                 140

Ser Ala Pro His Cys Gln Ile Gln Gly Ser Gln Asp Ile Gly Ser Asp
145                 150                 155                 160

Val Ile Leu Leu Cys Ser Ser Glu Glu Gly Ile Pro Arg Pro Thr Tyr
            165                 170                 175

Leu Trp Glu Lys Leu Asp Asn Thr Leu Lys Leu Pro Pro Thr Ala Thr
            180                 185                 190

Gln Asp Gln Val Gln Gly Thr Val Thr Ile Arg Asn Ile Ser Ala Leu
            195                 200                 205

Ser Ser Gly Leu Tyr Gln Cys Val Ala Ser Asn Ala Ile Gly Thr Ser
            210                 215                 220

Thr Cys Leu Leu Asp Leu Gln Val Ile Ser Pro Gln Pro Arg Asn Ile
225                 230                 235                 240

Gly Leu Ile Ala Gly Ala Ile Gly Thr Gly Ala Val Ile Ile Ile Phe
            245                 250                 255

Cys Ile Ala Leu Ile Leu Gly Ala Phe Phe Tyr Trp Arg Ser Lys Asn
            260                 265                 270

Lys Glu Glu Glu Glu Glu Ile Pro Asn Glu Ile Arg Glu Asp Asp
            275                 280                 285

Leu Pro Pro Lys Cys Ser Ser Ala Lys Ala Phe His Thr Glu Ile Ser
290                 295                 300

Ser Ser Asp Asn Asn Thr Leu Thr Ser Ser Asn Ala Tyr Asn Ser Arg
305                 310                 315                 320

Tyr Trp Ser Asn Asn Pro Lys Val His Arg Asn Thr Glu Ser Val Ser
            325                 330                 335

His Phe Ser Asp Leu Gly Gln Ser Phe Ser Phe His Ser Gly Asn Ala
            340                 345                 350

Asn Ile Pro Ser Ile Tyr Ala Asn Gly Thr His Leu Val Pro Gly Gln
            355                 360                 365

His Lys Thr Leu Val Val Thr Ala Asn Arg Gly Ser Ser Pro Gln Val
            370                 375                 380

Met Ser Arg Ser Asn Gly Ser Val Ser Arg Lys Pro Arg Pro Pro His
385                 390                 395                 400

Thr His Ser Tyr Thr Ile Ser His Ala Thr Leu Glu Arg Ile Gly Ala
            405                 410                 415

Val Pro Val Met Val Pro Ala Gln Ser Arg Ala Gly Ser Leu Val
            420                 425                 430

<210> SEQ ID NO 2
<211> LENGTH: 245
<212> TYPE: PRT
<213> ORGANISM: homo sapiens

<400> SEQUENCE: 2

Met Thr Ser Gln Arg Ser Pro Leu Ala Pro Leu Leu Leu Ser Leu
1               5                   10                  15

His Gly Val Ala Ala Ser Leu Glu Val Ser Glu Ser Pro Gly Ser Ile
            20                  25                  30

Gln Val Ala Arg Gly Gln Thr Ala Val Leu Pro Cys Thr Phe Thr Thr
            35                  40                  45
```

Ser Ala Ala Leu Ile Asn Leu Asn Val Ile Trp Met Val Thr Pro Leu
 50                  55                  60

Ser Asn Ala Asn Gln Pro Glu Gln Val Ile Leu Tyr Gln Gly Gly Gln
 65                  70                  75                  80

Met Phe Asp Gly Ala Pro Arg Phe His Gly Arg Val Gly Phe Thr Gly
                 85                  90                  95

Thr Met Pro Ala Thr Asn Val Ser Ile Phe Ile Asn Asn Thr Gln Leu
            100                 105                 110

Ser Asp Thr Gly Thr Tyr Gln Cys Leu Val Asn Asn Leu Pro Asp Ile
        115                 120                 125

Gly Gly Arg Asn Ile Gly Val Thr Gly Leu Thr Val Leu Val Pro Pro
130                 135                 140

Ser Ala Pro His Cys Gln Ile Gln Gly Ser Gln Asp Ile Gly Ser Asp
145                 150                 155                 160

Val Ile Leu Leu Cys Ser Ser Glu Glu Gly Ile Pro Arg Pro Thr Tyr
                165                 170                 175

Leu Trp Glu Lys Leu Asp Asn Thr Leu Lys Leu Pro Pro Thr Ala Thr
            180                 185                 190

Gln Asp Gln Val Gln Gly Thr Val Thr Ile Arg Asn Ile Ser Ala Leu
        195                 200                 205

Ser Ser Gly Leu Tyr Gln Cys Val Ala Ser Asn Ala Ile Gly Thr Ser
210                 215                 220

Thr Cys Leu Leu Asp Leu Gln Val Ile Ser Pro Gln Pro Arg Asn Ile
225                 230                 235                 240

Gly Leu Ile Ala Gly
                245

<210> SEQ ID NO 3
<211> LENGTH: 460
<212> TYPE: PRT
<213> ORGANISM: homo sapiens

<400> SEQUENCE: 3

Leu Glu Val Ser Glu Ser Pro Gly Ser Ile Gln Val Ala Arg Gly Gln
1               5                   10                  15

Thr Ala Val Leu Pro Cys Thr Phe Thr Thr Ser Ala Ala Leu Ile Asn
            20                  25                  30

Leu Asn Val Ile Trp Met Val Thr Pro Leu Ser Asn Ala Asn Gln Pro
        35                  40                  45

Glu Gln Val Ile Leu Tyr Gln Gly Gly Gln Met Phe Asp Gly Ala Pro
 50                  55                  60

Arg Phe His Gly Arg Val Gly Phe Thr Gly Thr Met Pro Ala Thr Asn
 65                  70                  75                  80

Val Ser Ile Phe Ile Asn Asn Thr Gln Leu Ser Asp Thr Gly Thr Tyr
                 85                  90                  95

Gln Cys Leu Val Asn Asn Leu Pro Asp Ile Gly Gly Arg Asn Ile Gly
            100                 105                 110

Val Thr Gly Leu Thr Val Leu Val Pro Pro Ser Ala Pro His Cys Gln
        115                 120                 125

Ile Gln Gly Ser Gln Asp Ile Gly Ser Asp Val Ile Leu Leu Cys Ser
        130                 135                 140

Ser Glu Glu Gly Ile Pro Arg Pro Thr Tyr Leu Trp Glu Lys Leu Asp
145                 150                 155                 160

Asn Thr Leu Lys Leu Pro Pro Thr Ala Thr Gln Asp Gln Val Gln Gly
                165                 170                 175

```
Thr Val Thr Ile Arg Asn Ile Ser Ala Leu Ser Ser Gly Leu Tyr Gln
            180                 185                 190

Cys Val Ala Ser Asn Ala Ile Gly Thr Ser Thr Cys Leu Leu Asp Leu
            195                 200                 205

Gln Val Ile Ser Pro Gln Pro Arg Asn Ile Gly Leu Ile Ala Gly Ile
            210                 215                 220

Glu Gly Arg Met Asp Pro Lys Ser Cys Asp Lys Thr His Thr Cys Pro
225                 230                 235                 240

Pro Cys Pro Ala Pro Glu Ala Glu Gly Ala Pro Ser Val Phe Leu Phe
            245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
            275                 280                 285

Asn Trp Tyr Val Asp Gly Val Glu Val His Asn Ala Lys Thr Lys Pro
            290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
            325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
            355                 360                 365

Asp Glu Leu Thr Lys Asn Gln Val Ser Leu Thr Cys Leu Val Lys Gly
            370                 375                 380

Phe Tyr Pro Ser Asp Ile Ala Val Glu Trp Glu Ser Asn Gly Gln Pro
385                 390                 395                 400

Glu Asn Asn Tyr Lys Ala Thr Pro Pro Val Leu Asp Ser Asp Gly Ser
            405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
            435                 440                 445

Tyr Thr Gln Lys Ser Leu Ser Leu Ser Pro Gly Lys
            450                 455                 460

<210> SEQ ID NO 4
<211> LENGTH: 311
<212> TYPE: PRT
<213> ORGANISM: homo sapiens

<400> SEQUENCE: 4

Met Gly Val Pro Thr Ala Leu Glu Ala Gly Ser Trp Arg Trp Gly Ser
1               5                   10                  15

Leu Leu Phe Ala Leu Phe Leu Ala Ala Ser Leu Gly Pro Val Ala Ala
            20                  25                  30

Phe Lys Val Ala Thr Pro Tyr Ser Leu Tyr Val Cys Pro Glu Gly Gln
            35                  40                  45

Asn Val Thr Leu Thr Cys Arg Leu Leu Gly Pro Val Asp Lys Gly His
            50                  55                  60

Asp Val Thr Phe Tyr Lys Thr Trp Tyr Arg Ser Ser Arg Gly Glu Val
65                  70                  75                  80

Gln Thr Cys Ser Glu Arg Arg Pro Ile Arg Asn Leu Thr Phe Gln Asp
```

```
                     85                  90                  95
Leu His Leu His His Gly Gly His Gln Ala Ala Asn Thr Ser His Asp
                100                 105                 110

Leu Ala Gln Arg His Gly Leu Glu Ser Ala Ser Asp His His Gly Asn
            115                 120                 125

Phe Ser Ile Thr Met Arg Asn Leu Thr Leu Leu Asp Ser Gly Leu Tyr
        130                 135                 140

Cys Cys Leu Val Val Glu Ile Arg His His Ser Glu His Arg Val
145                 150                 155                 160

His Gly Ala Met Glu Leu Gln Val Gln Thr Gly Lys Asp Ala Pro Ser
                165                 170                 175

Asn Cys Val Val Tyr Pro Ser Ser Ser Gln Asp Ser Glu Asn Ile Thr
            180                 185                 190

Ala Ala Ala Leu Ala Thr Gly Ala Cys Ile Val Gly Ile Leu Cys Leu
        195                 200                 205

Pro Leu Ile Leu Leu Leu Val Tyr Lys Gln Arg Gln Ala Ala Ser Asn
    210                 215                 220

Arg Arg Ala Gln Glu Leu Val Arg Met Asp Ser Asn Ile Gln Gly Ile
225                 230                 235                 240

Glu Asn Pro Gly Phe Glu Ala Ser Pro Pro Ala Gln Gly Ile Pro Glu
                245                 250                 255

Ala Lys Val Arg His Pro Leu Ser Tyr Val Ala Gln Arg Gln Pro Ser
            260                 265                 270

Glu Ser Gly Arg His Leu Leu Ser Glu Pro Ser Thr Pro Leu Ser Pro
        275                 280                 285

Pro Gly Pro Gly Asp Val Phe Phe Pro Ser Leu Asp Pro Val Pro Asp
    290                 295                 300

Ser Pro Asn Phe Glu Val Ile
305                 310

<210> SEQ ID NO 5
<211> LENGTH: 198
<212> TYPE: PRT
<213> ORGANISM: homo sapiens

<400> SEQUENCE: 5

Met Gly Val Pro Thr Ala Leu Glu Ala Gly Ser Trp Arg Trp Gly Ser
1               5                   10                  15

Leu Leu Phe Ala Leu Phe Leu Ala Ala Ser Leu Gly Pro Val Ala Ala
            20                  25                  30

Phe Lys Val Ala Thr Pro Tyr Ser Leu Tyr Val Cys Pro Glu Gly Gln
        35                  40                  45

Asn Val Thr Leu Thr Cys Arg Leu Leu Gly Pro Val Asp Lys Gly His
    50                  55                  60

Asp Val Thr Phe Tyr Lys Thr Trp Tyr Arg Ser Ser Arg Gly Glu Val
65                  70                  75                  80

Gln Thr Cys Ser Glu Arg Arg Pro Ile Arg Asn Leu Thr Phe Gln Asp
                85                  90                  95

Leu His Leu His His Gly Gly His Gln Ala Ala Asn Thr Ser His Asp
                100                 105                 110

Leu Ala Gln Arg His Gly Leu Glu Ser Ala Ser Asp His His Gly Asn
            115                 120                 125

Phe Ser Ile Thr Met Arg Asn Leu Thr Leu Leu Asp Ser Gly Leu Tyr
        130                 135                 140
```

```
Cys Cys Leu Val Val Glu Ile Arg His His His Ser Glu His Arg Val
145                 150                 155                 160

His Gly Ala Met Glu Leu Gln Val Gln Thr Gly Lys Asp Ala Pro Ser
            165                 170                 175

Asn Cys Val Val Tyr Pro Ser Ser Gln Glu Ser Glu Asn Ile Thr
        180                 185                 190

Ala Ala Ile Glu Gly Arg
        195

<210> SEQ ID NO 6
<211> LENGTH: 399
<212> TYPE: PRT
<213> ORGANISM: homo sapiens

<400> SEQUENCE: 6

Phe Lys Val Ala Thr Pro Tyr Ser Leu Tyr Val Cys Pro Glu Gly Gln
1               5                   10                  15

Asn Val Thr Leu Thr Cys Arg Leu Leu Gly Pro Val Asp Lys Gly His
            20                  25                  30

Asp Val Thr Phe Tyr Lys Thr Trp Tyr Arg Ser Ser Arg Gly Glu Val
        35                  40                  45

Gln Thr Cys Ser Glu Arg Arg Pro Ile Arg Asn Leu Thr Phe Gln Asp
    50                  55                  60

Leu His Leu His His Gly Gly His Gln Ala Ala Asn Thr Ser His Asp
65                  70                  75                  80

Leu Ala Gln Arg His Gly Leu Glu Ser Ala Ser Asp His His Gly Asn
                85                  90                  95

Phe Ser Ile Thr Met Arg Asn Leu Thr Leu Leu Asp Ser Gly Leu Tyr
            100                 105                 110

Cys Cys Leu Val Val Glu Ile Arg His His Ser Glu His Arg Val
        115                 120                 125

His Gly Ala Met Glu Leu Gln Val Gln Thr Gly Lys Asp Ala Pro Ser
    130                 135                 140

Asn Cys Val Val Tyr Pro Ser Ser Gln Glu Ser Glu Asn Ile Thr
145                 150                 155                 160

Ala Ala Ile Glu Gly Arg Met Asp Pro Lys Ser Cys Asp Lys Thr His
                165                 170                 175

Thr Cys Pro Pro Cys Pro Ala Pro Glu Ala Glu Gly Ala Pro Ser Val
            180                 185                 190

Phe Leu Phe Pro Pro Lys Pro Lys Asp Thr Leu Met Ile Ser Arg Thr
        195                 200                 205

Pro Glu Val Thr Cys Val Val Val Asp Val Ser His Glu Asp Pro Glu
    210                 215                 220

Val Lys Phe Asn Trp Tyr Val Asp Gly Val Glu Val His Asn Ala Lys
225                 230                 235                 240

Thr Lys Pro Arg Glu Glu Gln Tyr Asn Ser Thr Tyr Arg Val Val Ser
                245                 250                 255

Val Leu Thr Val Leu His Gln Asp Trp Leu Asn Gly Lys Glu Tyr Lys
            260                 265                 270

Cys Lys Val Ser Asn Lys Ala Leu Pro Ala Pro Ile Glu Lys Thr Ile
        275                 280                 285

Ser Lys Ala Lys Gly Gln Pro Arg Glu Pro Gln Val Tyr Thr Leu Pro
    290                 295                 300

Pro Ser Arg Asp Glu Leu Thr Lys Asn Gln Val Ser Leu Thr Cys Leu
305                 310                 315                 320
```

-continued

Val Lys Gly Phe Tyr Pro Ser Asp Ile Ala Val Trp Glu Ser Asn
           325                 330                 335

Gly Gln Pro Glu Asn Asn Tyr Lys Ala Thr Pro Pro Val Leu Asp Ser
            340                 345                 350

Asp Gly Ser Phe Phe Leu Tyr Ser Lys Leu Thr Val Asp Lys Ser Arg
            355                 360                 365

Trp Gln Gln Gly Asn Val Phe Ser Cys Ser Val Met His Glu Ala Leu
370                 375                 380

His Asn His Tyr Thr Gln Lys Ser Leu Ser Leu Ser Pro Gly Lys
385                 390                 395

<210> SEQ ID NO 7
<211> LENGTH: 772
<212> TYPE: PRT
<213> ORGANISM: Artificial
<220> FEATURE:
<223> OTHER INFORMATION: VISTA(1-195)-COMP-AlkPhos-Flag/His fusion

<400> SEQUENCE: 7

Met Gly Val Pro Thr Ala Leu Glu Ala Gly Ser Trp Arg Trp Gly Ser
1               5                   10                  15

Leu Leu Phe Ala Leu Phe Leu Ala Ala Ser Leu Gly Pro Val Ala Ala
                20                  25                  30

Phe Lys Val Ala Thr Pro Tyr Ser Leu Tyr Val Cys Pro Glu Gly Gln
            35                  40                  45

Asn Val Thr Leu Thr Cys Arg Leu Leu Gly Pro Val Asp Lys Gly His
        50                  55                  60

Asp Val Thr Phe Tyr Lys Thr Trp Tyr Arg Ser Ser Arg Gly Glu Val
65                  70                  75                  80

Gln Thr Cys Ser Glu Arg Arg Pro Ile Arg Asn Leu Thr Phe Gln Asp
                85                  90                  95

Leu His Leu His His Gly Gly His Gln Ala Ala Asn Thr Ser His Asp
            100                 105                 110

Leu Ala Gln Arg His Gly Leu Glu Ser Ala Ser Asp His His Gly Asn
        115                 120                 125

Phe Ser Ile Thr Met Arg Asn Leu Thr Leu Leu Asp Ser Gly Leu Tyr
130                 135                 140

Cys Cys Leu Val Val Glu Ile Arg His His Ser Glu His Arg Val
145                 150                 155                 160

His Gly Ala Met Glu Leu Gln Val Gln Thr Gly Lys Asp Ala Pro Ser
                165                 170                 175

Asn Cys Val Val Tyr Pro Ser Ser Ser Gln Glu Ser Glu Asn Ile Thr
            180                 185                 190

Ala Ala Gly Ser Glu Asn Leu Tyr Phe Gln Gly Asn Ser Gly Gly Gly
        195                 200                 205

Ser Gly Gly Gly Thr Gly Gly Gly Asp Leu Ala Pro Gln Met Leu Arg
210                 215                 220

Glu Leu Gln Glu Thr Asn Ala Ala Leu Gln Asp Val Arg Glu Leu Leu
225                 230                 235                 240

Arg His Arg Val Lys Glu Ile Thr Phe Leu Lys Asn Thr Val Met Glu
                245                 250                 255

Cys Asp Ala Cys Gly Leu Asp Arg Asn Leu Pro Pro Leu Ala Pro Leu
            260                 265                 270

Gly Pro Ile Ile Pro Val Glu Glu Glu Asn Pro Asp Phe Trp Asn Arg
        275                 280                 285

```
Glu Ala Ala Glu Ala Leu Gly Ala Ala Lys Lys Leu Gln Pro Ala Gln
    290                 295                 300
Thr Ala Ala Lys Asn Leu Ile Ile Phe Leu Gly Asp Gly Met Gly Val
305                 310                 315                 320
Ser Thr Val Thr Ala Ala Arg Ile Leu Lys Gly Gln Lys Lys Asp Lys
                325                 330                 335
Leu Gly Pro Glu Ile Pro Leu Ala Met Asp Arg Phe Pro Tyr Val Ala
                340                 345                 350
Leu Ser Lys Thr Tyr Asn Val Asp Lys His Val Pro Asp Ser Gly Ala
            355                 360                 365
Thr Ala Thr Ala Tyr Leu Cys Gly Val Lys Gly Asn Phe Gln Thr Ile
    370                 375                 380
Gly Leu Ser Ala Ala Arg Phe Asn Gln Cys Asn Thr Thr Arg Gly
385                 390                 395                 400
Asn Glu Val Ile Ser Val Met Asn Arg Ala Lys Lys Ala Gly Lys Ser
                405                 410                 415
Val Gly Val Val Thr Thr Thr Arg Val Gln His Ala Ser Pro Ala Gly
                420                 425                 430
Thr Tyr Ala His Thr Val Asn Arg Asn Trp Tyr Ser Asp Ala Asp Val
            435                 440                 445
Pro Ala Ser Ala Arg Gln Glu Gly Cys Gln Asp Ile Ala Thr Gln Leu
    450                 455                 460
Ile Ser Asn Met Asp Ile Asp Val Ile Leu Gly Gly Gly Arg Lys Tyr
465                 470                 475                 480
Met Phe Arg Met Gly Thr Pro Asp Pro Glu Tyr Pro Asp Asp Tyr Ser
                485                 490                 495
Gln Gly Gly Thr Arg Leu Asp Gly Lys Asn Leu Val Gln Glu Trp Leu
            500                 505                 510
Ala Lys Arg Gln Gly Ala Arg Tyr Val Trp Asn Arg Thr Glu Leu Met
    515                 520                 525
Gln Ala Ser Leu Asp Pro Ser Val Thr His Leu Met Gly Leu Phe Glu
530                 535                 540
Pro Gly Asp Met Lys Tyr Glu Ile His Arg Asp Ser Thr Leu Asp Pro
545                 550                 555                 560
Ser Leu Met Glu Met Thr Glu Ala Ala Leu Arg Leu Leu Ser Arg Asn
                565                 570                 575
Pro Arg Gly Phe Phe Leu Phe Val Glu Gly Gly Arg Ile Asp His Gly
            580                 585                 590
His His Glu Ser Arg Ala Tyr Arg Ala Leu Thr Glu Thr Ile Met Phe
    595                 600                 605
Asp Asp Ala Ile Glu Arg Ala Gly Gln Leu Thr Ser Glu Glu Asp Thr
610                 615                 620
Leu Ser Leu Val Thr Ala Asp His Ser His Val Phe Ser Phe Gly Gly
625                 630                 635                 640
Tyr Pro Leu Arg Gly Ser Ser Ile Phe Gly Leu Ala Pro Gly Lys Ala
                645                 650                 655
Arg Asp Arg Lys Ala Tyr Thr Val Leu Leu Tyr Gly Asn Gly Pro Gly
            660                 665                 670
Tyr Val Leu Lys Asp Gly Ala Arg Pro Asp Val Thr Glu Ser Glu Ser
    675                 680                 685
Gly Ser Pro Glu Tyr Arg Gln Gln Ser Ala Val Pro Leu Asp Glu Glu
690                 695                 700
```

```
Thr His Ala Gly Glu Asp Val Ala Val Phe Ala Arg Gly Pro Gln Ala
705                 710                 715                 720

His Leu Val His Gly Val Gln Glu Gln Thr Phe Ile Ala His Val Met
            725                 730                 735

Ala Phe Ala Ala Cys Leu Glu Pro Tyr Thr Ala Cys Asp Leu Ala Pro
            740                 745                 750

Pro Ala Gly Thr Thr Asp Asp Tyr Lys Asp Asp Asp Lys His His
        755                 760                 765

His His His His
    770

<210> SEQ ID NO 8

<400> SEQUENCE: 8

000

<210> SEQ ID NO 9
<211> LENGTH: 822
<212> TYPE: PRT
<213> ORGANISM: Artificial
<220> FEATURE:
<223> OTHER INFORMATION: VSIG3(1-245)-COMP-AlkPhos-Flag/His fusion

<400> SEQUENCE: 9

Met Thr Ser Gln Arg Ser Pro Leu Ala Pro Leu Leu Leu Ser Leu
1               5                   10                  15

His Gly Val Ala Ala Ser Leu Glu Val Ser Glu Ser Pro Gly Ser Ile
            20                  25                  30

Gln Val Ala Arg Gly Gln Pro Ala Val Leu Pro Cys Thr Phe Thr Thr
        35                  40                  45

Ser Ala Ala Leu Ile Asn Leu Asn Val Ile Trp Met Val Thr Pro Leu
50                  55                  60

Ser Asn Ala Asn Gln Pro Glu Gln Val Ile Leu Tyr Gln Gly Gly Gln
65                  70                  75                  80

Met Phe Asp Gly Ala Pro Arg Phe His Gly Arg Val Gly Phe Thr Gly
                85                  90                  95

Thr Met Pro Ala Thr Asn Val Ser Ile Phe Ile Asn Asn Thr Gln Leu
            100                 105                 110

Ser Asp Thr Gly Thr Tyr Gln Cys Leu Val Asn Asn Leu Pro Asp Ile
        115                 120                 125

Gly Gly Arg Asn Ile Gly Val Thr Gly Leu Thr Val Leu Val Pro Pro
130                 135                 140

Ser Ala Pro His Cys Gln Ile Gln Gly Ser Gln Asp Ile Gly Ser Asp
145                 150                 155                 160

Val Ile Leu Leu Cys Ser Ser Glu Glu Gly Ile Pro Arg Pro Thr Tyr
                165                 170                 175

Leu Trp Glu Lys Leu Asp Asn Thr Leu Lys Leu Pro Pro Thr Ala Thr
            180                 185                 190

Gln Asp Gln Val Gln Gly Thr Val Thr Ile Arg Asn Ile Ser Ala Leu
        195                 200                 205

Ser Ser Gly Leu Tyr Gln Cys Val Ala Ser Asn Ala Ile Gly Thr Ser
210                 215                 220

Thr Cys Leu Leu Asp Leu Gln Val Ile Ser Pro Gln Pro Arg Asn Ile
225                 230                 235                 240

Gly Leu Ile Ala Gly Ser Glu Asn Leu Tyr Phe Gln Gly Asn Ser Gly
                245                 250                 255
```

```
Gly Gly Ser Gly Gly Gly Thr Gly Gly Gly Asp Leu Ala Pro Gln Met
            260                 265                 270

Leu Arg Glu Leu Gln Glu Thr Asn Ala Ala Leu Gln Asp Val Arg Glu
        275                 280                 285

Leu Leu Arg His Arg Val Lys Glu Ile Thr Phe Leu Lys Asn Thr Val
        290                 295                 300

Met Glu Cys Asp Ala Cys Gly Leu Asp Arg Asn Leu Pro Pro Leu Ala
305                 310                 315                 320

Pro Leu Gly Pro Ile Ile Pro Val Glu Glu Asn Pro Asp Phe Trp
                325                 330                 335

Asn Arg Glu Ala Ala Glu Ala Leu Gly Ala Ala Lys Lys Leu Gln Pro
            340                 345                 350

Ala Gln Thr Ala Ala Lys Asn Leu Ile Ile Phe Leu Gly Asp Gly Met
        355                 360                 365

Gly Val Ser Thr Val Thr Ala Ala Arg Ile Leu Lys Gly Gln Lys Lys
    370                 375                 380

Asp Lys Leu Gly Pro Glu Ile Pro Leu Ala Met Asp Arg Phe Pro Tyr
385                 390                 395                 400

Val Ala Leu Ser Lys Thr Tyr Asn Val Asp Lys His Val Pro Asp Ser
            405                 410                 415

Gly Ala Thr Ala Thr Ala Tyr Leu Cys Gly Val Lys Gly Asn Phe Gln
        420                 425                 430

Thr Ile Gly Leu Ser Ala Ala Arg Phe Asn Gln Cys Asn Thr Thr
    435                 440                 445

Arg Gly Asn Glu Val Ile Ser Val Met Asn Arg Ala Lys Lys Ala Gly
    450                 455                 460

Lys Ser Val Gly Val Val Thr Thr Thr Arg Val Gln His Ala Ser Pro
465                 470                 475                 480

Ala Gly Thr Tyr Ala His Thr Val Asn Arg Asn Trp Tyr Ser Asp Ala
            485                 490                 495

Asp Val Pro Ala Ser Ala Arg Gln Glu Gly Cys Gln Asp Ile Ala Thr
            500                 505                 510

Gln Leu Ile Ser Asn Met Asp Ile Asp Val Ile Leu Gly Gly Gly Arg
        515                 520                 525

Lys Tyr Met Phe Arg Met Gly Thr Pro Asp Pro Glu Tyr Pro Asp Asp
530                 535                 540

Tyr Ser Gln Gly Gly Thr Arg Leu Asp Gly Lys Asn Leu Val Gln Glu
545                 550                 555                 560

Trp Leu Ala Lys Arg Gln Gly Ala Arg Tyr Val Trp Asn Arg Thr Glu
            565                 570                 575

Leu Met Gln Ala Ser Leu Asp Pro Ser Val Thr His Leu Met Gly Leu
        580                 585                 590

Phe Glu Pro Gly Asp Met Lys Tyr Glu Ile His Arg Asp Ser Thr Leu
    595                 600                 605

Asp Pro Ser Leu Met Glu Met Thr Glu Ala Ala Leu Arg Leu Leu Ser
        610                 615                 620

Arg Asn Pro Arg Gly Phe Phe Leu Phe Val Glu Gly Gly Arg Ile Asp
625                 630                 635                 640

His Gly His His Glu Ser Arg Ala Tyr Arg Ala Leu Thr Glu Thr Ile
            645                 650                 655

Met Phe Asp Asp Ala Ile Glu Arg Ala Gly Gln Leu Thr Ser Glu Glu
            660                 665                 670
```

```
Asp Thr Leu Ser Leu Val Thr Ala Asp His Ser His Val Phe Ser Phe
        675                 680                 685

Gly Gly Tyr Pro Leu Arg Gly Ser Ser Ile Phe Gly Leu Ala Pro Gly
    690                 695                 700

Lys Ala Arg Asp Arg Lys Ala Tyr Thr Val Leu Leu Tyr Gly Asn Gly
705                 710                 715                 720

Pro Gly Tyr Val Leu Lys Asp Gly Ala Arg Pro Asp Val Thr Glu Ser
                725                 730                 735

Glu Ser Gly Ser Pro Glu Tyr Arg Gln Ser Ala Val Pro Leu Asp
            740                 745                 750

Glu Glu Thr His Ala Gly Glu Asp Val Ala Val Phe Ala Arg Gly Pro
            755                 760                 765

Gln Ala His Leu Val His Gly Val Gln Glu Gln Thr Phe Ile Ala His
        770                 775                 780

Val Met Ala Phe Ala Ala Cys Leu Glu Pro Tyr Thr Ala Cys Asp Leu
785                 790                 795                 800

Ala Pro Pro Ala Gly Thr Thr Asp Asp Tyr Lys Asp Asp Asp Lys
                805                 810                 815

His His His His His His
            820

<210> SEQ ID NO 10
<211> LENGTH: 330
<212> TYPE: PRT
<213> ORGANISM: Artificial
<220> FEATURE:
<223> OTHER INFORMATION: VSIG3(1-245)-COMP-His fusion

<400> SEQUENCE: 10

Met Thr Ser Gln Arg Ser Pro Leu Ala Pro Leu Leu Leu Ser Leu
1               5                   10                  15

His Gly Val Ala Ala Ser Leu Glu Val Ser Glu Ser Pro Gly Ser Ile
                20                  25                  30

Gln Val Ala Arg Gly Gln Pro Ala Val Leu Pro Cys Thr Phe Thr Thr
            35                  40                  45

Ser Ala Ala Leu Ile Asn Leu Asn Val Ile Trp Met Val Thr Pro Leu
    50                  55                  60

Ser Asn Ala Asn Gln Pro Glu Gln Val Ile Leu Tyr Gln Gly Gly Gln
65                  70                  75                  80

Met Phe Asp Gly Ala Pro Arg Phe His Gly Arg Val Gly Phe Thr Gly
                85                  90                  95

Thr Met Pro Ala Thr Asn Val Ser Ile Phe Ile Asn Asn Thr Gln Leu
            100                 105                 110

Ser Asp Thr Gly Thr Tyr Gln Cys Leu Val Asn Asn Leu Pro Asp Ile
        115                 120                 125

Gly Gly Arg Asn Ile Gly Val Thr Gly Leu Thr Val Leu Val Pro Pro
    130                 135                 140

Ser Ala Pro His Cys Gln Ile Gln Gly Ser Gln Asp Ile Gly Ser Asp
145                 150                 155                 160

Val Ile Leu Leu Cys Ser Ser Glu Glu Gly Ile Pro Arg Pro Thr Tyr
                165                 170                 175

Leu Trp Glu Lys Leu Asp Asn Thr Leu Lys Leu Pro Pro Thr Ala Thr
            180                 185                 190

Gln Asp Gln Val Gln Gly Thr Val Thr Ile Arg Asn Ile Ser Ala Leu
        195                 200                 205
```

```
Ser Ser Gly Leu Tyr Gln Cys Val Ala Ser Asn Ala Ile Gly Thr Ser
    210                 215                 220
Thr Cys Leu Leu Asp Leu Gln Val Ile Ser Pro Gln Pro Arg Asn Ile
225                 230                 235                 240
Gly Leu Ile Ala Gly Ser Glu Asn Leu Tyr Phe Gln Gly Asn Ser Gly
                245                 250                 255
Gly Gly Ser Gly Gly Gly Thr Gly Gly Gly Asp Leu Ala Pro Gln Met
                260                 265                 270
Leu Arg Glu Leu Gln Glu Thr Asn Ala Ala Leu Gln Asp Val Arg Glu
            275                 280                 285
Leu Leu Arg His Arg Val Lys Glu Ile Thr Phe Leu Lys Asn Thr Val
            290                 295                 300
Met Glu Cys Asp Ala Cys Gly Leu Asp Arg Asn Leu Pro Pro Leu Ala
305                 310                 315                 320
Pro Leu Gly Pro His His His His His His
                325                 330
```

<210> SEQ ID NO 11
<211> LENGTH: 841
<212> TYPE: PRT
<213> ORGANISM: Artificial
<220> FEATURE:
<223> OTHER INFORMATION: VSIG8(1-263)-COMP-AlkPhos-Flag/His fusion

<400> SEQUENCE: 11

```
Met Arg Val Gly Gly Ala Phe His Leu Leu Val Cys Leu Ser Pro
1               5                   10                  15
Ala Leu Leu Ser Ala Val Arg Ile Asn Gly Asp Gly Gln Glu Val Leu
                20                  25                  30
Tyr Leu Ala Glu Gly Asp Asn Val Arg Leu Gly Cys Pro Tyr Val Leu
            35                  40                  45
Asp Pro Glu Asp Tyr Gly Pro Asn Gly Leu Asp Ile Glu Trp Met Gln
        50                  55                  60
Val Asn Ser Asp Pro Ala His His Arg Glu Asn Val Phe Leu Ser Tyr
65                  70                  75                  80
Gln Asp Lys Arg Ile Asn His Gly Ser Leu Pro His Leu Gln Gln Arg
                85                  90                  95
Val Arg Phe Ala Ala Ser Asp Pro Ser Gln Tyr Asp Ala Ser Ile Asn
            100                 105                 110
Leu Met Asn Leu Gln Val Ser Asp Thr Ala Thr Tyr Glu Cys Arg Val
            115                 120                 125
Lys Lys Thr Thr Met Ala Thr Arg Lys Val Ile Val Thr Val Gln Ala
        130                 135                 140
Arg Pro Ala Val Pro Met Cys Trp Thr Glu Gly His Met Thr Tyr Gly
145                 150                 155                 160
Asn Asp Val Val Leu Lys Cys Tyr Ala Ser Gly Gly Ser Gln Pro Leu
                165                 170                 175
Ser Tyr Lys Trp Ala Lys Ile Ser Gly His His Tyr Pro Tyr Arg Ala
            180                 185                 190
Gly Ser Tyr Thr Ser Gln His Ser Tyr His Ser Glu Leu Ser Tyr Gln
        195                 200                 205
Glu Ser Phe His Ser Ser Ile Asn Gln Gly Leu Asn Asn Gly Asp Leu
    210                 215                 220
Val Leu Lys Asp Ile Ser Arg Ala Asp Asp Gly Leu Tyr Gln Cys Thr
225                 230                 235                 240
```

-continued

```
Val Ala Asn Asn Val Gly Tyr Ser Val Cys Val Glu Val Lys Val
                245                 250                 255
Ser Asp Ser Arg Arg Ile Gly Ser Glu Asn Leu Tyr Phe Gln Gly
            260                 265                 270
Asn Ser Gly Gly Gly Ser Gly Gly Thr Gly Gly Asp Leu Ala
        275                 280                 285
Pro Gln Met Leu Arg Glu Leu Gln Glu Thr Asn Ala Ala Leu Gln Asp
290                 295                 300
Val Arg Glu Leu Leu Arg His Arg Val Lys Glu Ile Thr Phe Leu Lys
305                 310                 315                 320
Asn Thr Val Met Glu Cys Asp Ala Cys Gly Leu Asp Arg Asn Leu Pro
                325                 330                 335
Pro Leu Ala Pro Leu Gly Pro Ile Ile Pro Val Glu Glu Asn Pro
            340                 345                 350
Asp Phe Trp Asn Arg Glu Ala Ala Glu Ala Leu Gly Ala Ala Lys Lys
        355                 360                 365
Leu Gln Pro Ala Gln Thr Ala Ala Lys Asn Leu Ile Ile Phe Leu Gly
    370                 375                 380
Asp Gly Met Gly Val Ser Thr Val Thr Ala Ala Arg Ile Leu Lys Gly
385                 390                 395                 400
Gln Lys Lys Asp Lys Leu Gly Pro Glu Ile Pro Leu Ala Met Asp Arg
                405                 410                 415
Phe Pro Tyr Val Ala Leu Ser Lys Thr Tyr Asn Val Asp Lys His Val
            420                 425                 430
Pro Asp Ser Gly Ala Thr Ala Thr Ala Tyr Leu Cys Gly Val Lys Gly
        435                 440                 445
Asn Phe Gln Thr Ile Gly Leu Ser Ala Ala Arg Phe Asn Gln Cys
    450                 455                 460
Asn Thr Thr Arg Gly Asn Glu Val Ile Ser Val Met Asn Arg Ala Lys
465                 470                 475                 480
Lys Ala Gly Lys Ser Val Gly Val Val Thr Thr Thr Arg Val Gln His
                485                 490                 495
Ala Ser Pro Ala Gly Thr Tyr Ala His Thr Val Asn Arg Asn Trp Tyr
            500                 505                 510
Ser Asp Ala Asp Val Pro Ala Ser Ala Arg Gln Glu Gly Cys Gln Asp
        515                 520                 525
Ile Ala Thr Gln Leu Ile Ser Asn Met Asp Ile Asp Val Ile Leu Gly
    530                 535                 540
Gly Gly Arg Lys Tyr Met Phe Arg Met Gly Thr Pro Asp Pro Glu Tyr
545                 550                 555                 560
Pro Asp Asp Tyr Ser Gln Gly Gly Thr Arg Leu Asp Gly Lys Asn Leu
                565                 570                 575
Val Gln Glu Trp Leu Ala Lys Arg Gln Gly Ala Arg Tyr Val Trp Asn
            580                 585                 590
Arg Thr Glu Leu Met Gln Ala Ser Leu Asp Pro Ser Val Thr His Leu
        595                 600                 605
Met Gly Leu Phe Glu Pro Gly Asp Met Lys Tyr Glu Ile His Arg Asp
    610                 615                 620
Ser Thr Leu Asp Pro Ser Leu Met Glu Met Thr Glu Ala Ala Leu Arg
625                 630                 635                 640
Leu Leu Ser Arg Asn Pro Arg Gly Phe Phe Leu Phe Val Glu Gly Gly
                645                 650                 655
Arg Ile Asp His Gly His His Glu Ser Arg Ala Tyr Arg Ala Leu Thr
```

```
                    660                 665                 670
Glu Thr Ile Met Phe Asp Asp Ala Ile Glu Arg Ala Gly Gln Leu Thr
            675                 680                 685

Ser Glu Glu Asp Thr Leu Ser Leu Val Thr Ala Asp His Ser His Val
        690                 695                 700

Phe Ser Phe Gly Gly Tyr Pro Leu Arg Gly Ser Ser Ile Phe Gly Leu
705                 710                 715                 720

Ala Pro Gly Lys Ala Arg Asp Arg Lys Ala Tyr Thr Val Leu Leu Tyr
                725                 730                 735

Gly Asn Gly Pro Gly Tyr Val Leu Lys Asp Gly Ala Arg Pro Asp Val
            740                 745                 750

Thr Glu Ser Glu Ser Gly Ser Pro Glu Tyr Arg Gln Gln Ser Ala Val
        755                 760                 765

Pro Leu Asp Glu Glu Thr His Ala Gly Glu Asp Val Ala Val Phe Ala
    770                 775                 780

Arg Gly Pro Gln Ala His Leu Val His Gly Val Gln Glu Gln Thr Phe
785                 790                 795                 800

Ile Ala His Val Met Ala Phe Ala Ala Cys Leu Glu Pro Tyr Thr Ala
                805                 810                 815

Cys Asp Leu Ala Pro Pro Ala Gly Thr Thr Asp Asp Tyr Lys Asp Asp
            820                 825                 830

Asp Asp Lys His His His His His His
        835                 840

<210> SEQ ID NO 12
<211> LENGTH: 349
<212> TYPE: PRT
<213> ORGANISM: Artificial
<220> FEATURE:
<223> OTHER INFORMATION: VSIG8(1-263)-COMP-His fusion

<400> SEQUENCE: 12

Met Arg Val Gly Gly Ala Phe His Leu Leu Leu Val Cys Leu Ser Pro
1               5                   10                  15

Ala Leu Leu Ser Ala Val Arg Ile Asn Gly Asp Gly Gln Glu Val Leu
            20                  25                  30

Tyr Leu Ala Glu Gly Asp Asn Val Arg Leu Gly Cys Pro Tyr Val Leu
        35                  40                  45

Asp Pro Glu Asp Tyr Gly Pro Asn Gly Leu Asp Ile Glu Trp Met Gln
    50                  55                  60

Val Asn Ser Asp Pro Ala His His Arg Glu Asn Val Phe Leu Ser Tyr
65                  70                  75                  80

Gln Asp Lys Arg Ile Asn His Gly Ser Leu Pro His Leu Gln Gln Arg
                85                  90                  95

Val Arg Phe Ala Ala Ser Asp Pro Ser Gln Tyr Asp Ala Ser Ile Asn
            100                 105                 110

Leu Met Asn Leu Gln Val Ser Asp Thr Ala Thr Tyr Glu Cys Arg Val
        115                 120                 125

Lys Lys Thr Thr Met Ala Thr Arg Lys Val Ile Val Thr Val Gln Ala
    130                 135                 140

Arg Pro Ala Val Pro Met Cys Trp Thr Glu Gly His Met Thr Tyr Gly
145                 150                 155                 160

Asn Asp Val Val Leu Lys Cys Tyr Ala Ser Gly Gly Ser Gln Pro Leu
                165                 170                 175

Ser Tyr Lys Trp Ala Lys Ile Ser Gly His His Tyr Pro Tyr Arg Ala
```

```
                180             185                 190
Gly Ser Tyr Thr Ser Gln His Ser Tyr His Ser Glu Leu Ser Tyr Gln
            195                 200                 205

Glu Ser Phe His Ser Ser Ile Asn Gln Gly Leu Asn Asn Gly Asp Leu
        210                 215                 220

Val Leu Lys Asp Ile Ser Arg Ala Asp Asp Gly Leu Tyr Gln Cys Thr
225                 230                 235                 240

Val Ala Asn Asn Val Gly Tyr Ser Val Cys Val Val Glu Val Lys Val
                245                 250                 255

Ser Asp Ser Arg Arg Ile Gly Gly Ser Glu Asn Leu Tyr Phe Gln Gly
            260                 265                 270

Asn Ser Gly Gly Gly Ser Gly Gly Gly Thr Gly Gly Gly Asp Leu Ala
            275                 280                 285

Pro Gln Met Leu Arg Glu Leu Gln Glu Thr Asn Ala Ala Leu Gln Asp
            290                 295                 300

Val Arg Glu Leu Leu Arg His Arg Val Lys Glu Ile Thr Phe Leu Lys
305                 310                 315                 320

Asn Thr Val Met Glu Cys Asp Ala Cys Gly Leu Asp Arg Asn Leu Pro
                325                 330                 335

Pro Leu Ala Pro Leu Gly Pro His His His His His His
            340                 345

<210> SEQ ID NO 13
<211> LENGTH: 11
<212> TYPE: PRT
<213> ORGANISM: Artificial
<220> FEATURE:
<223> OTHER INFORMATION: linker

<400> SEQUENCE: 13

Asn Ser Gly Gly Gly Ser Gly Gly Gly Thr Gly
1               5                   10

<210> SEQ ID NO 14
<211> LENGTH: 13
<212> TYPE: PRT
<213> ORGANISM: Artificial
<220> FEATURE:
<223> OTHER INFORMATION: linker

<400> SEQUENCE: 14

Leu Asp Arg Asn Leu Pro Pro Leu Ala Pro Leu Gly Pro
1               5                   10

<210> SEQ ID NO 15
<211> LENGTH: 414
<212> TYPE: PRT
<213> ORGANISM: artificial
<220> FEATURE:
<223> OTHER INFORMATION: heavy chain from clone 774206
<220> FEATURE:
<221> NAME/KEY: misc_feature
<222> LOCATION: (406)..(406)
<223> OTHER INFORMATION: Xaa can be any naturally occurring amino acid

<400> SEQUENCE: 15

Met Asn Phe Gly Leu Ser Trp Ile Phe Leu Val Pro Val Leu Lys Gly
1               5                   10                  15

Val Leu Cys Glu Val Lys Leu Val Glu Ser Gly Arg Gly Leu Val Gln
            20                  25                  30

Pro Gly Gly Ser Leu Lys Leu Ser Cys Ala Ala Ser Gly Phe Thr Phe
```

```
                35                  40                  45
Ser Ser Tyr Ser Met Ser Trp Val Arg Gln Thr Pro Glu Lys Arg Leu
 50                  55                  60

Glu Trp Val Ala Tyr Ile Ser Asn Gly Gly Ser Thr Tyr Tyr Pro
 65                  70                  75                  80

Asp Thr Val Lys Gly Arg Phe Thr Ile Ser Arg Asp Asn Ala Lys Asn
                 85                  90                  95

Thr Leu Tyr Leu Gln Met Ser Ser Leu Lys Ser Glu Asp Thr Ala Met
                100                 105                 110

Tyr Tyr Cys Ala Arg His Asp Gly Asn Tyr Pro Trp Phe Ala Tyr Trp
            115                 120                 125

Gly Gln Gly Thr Leu Val Thr Val Ser Ala Ala Lys Thr Thr Pro Pro
        130                 135                 140

Ser Val Tyr Pro Leu Ala Pro Gly Cys Gly Asp Thr Thr Gly Ser Ser
145                 150                 155                 160

Val Thr Leu Gly Cys Leu Val Lys Gly Tyr Phe Pro Glu Ser Leu Glu
                165                 170                 175

Pro Ser Gly Pro Ile Ser Thr Ile Asn Pro Cys Pro Pro Cys Lys Glu
                180                 185                 190

Cys His Lys Cys Pro Ala Pro Asn Leu Glu Gly Gly Pro Ser Val Phe
            195                 200                 205

Ile Phe Pro Pro Asn Ile Lys Asp Val Leu Met Ile Ser Leu Thr Pro
        210                 215                 220

Lys Val Thr Cys Val Val Val Asp Val Ser Glu Asp Asp Pro Asp Val
225                 230                 235                 240

Gln Ile Ser Trp Phe Val Asn Asn Val Glu Val His Thr Ala Gln Thr
                245                 250                 255

Gln Thr His Arg Glu Asp Tyr Asn Ser Thr Ile Arg Val Val Ser Thr
            260                 265                 270

Leu Pro Ile Gln His Gln Asp Trp Met Ser Gly Lys Glu Phe Lys Cys
        275                 280                 285

Lys Val Asn Asn Lys Asp Leu Pro Ser Pro Ile Glu Arg Thr Ile Ser
290                 295                 300

Lys Ile Lys Gly Leu Val Arg Ala Pro Gln Val Tyr Ile Leu Pro Pro
305                 310                 315                 320

Pro Ala Glu Gln Leu Ser Arg Lys Asp Val Ser Leu Thr Cys Leu Val
                325                 330                 335

Val Gly Phe Asn Pro Gly Asp Ile Ser Val Glu Trp Thr Ser Asn Gly
            340                 345                 350

His Thr Glu Glu Asn Tyr Lys Asp Thr Ala Pro Val Leu Asp Ser Asp
        355                 360                 365

Gly Ser Tyr Phe Ile Tyr Ser Lys Leu Asn Met Lys Thr Ser Lys Trp
    370                 375                 380

Glu Lys Thr Asp Ser Phe Ser Cys Asn Val Arg His Glu Gly Leu Lys
385                 390                 395                 400

Asn Tyr Tyr Leu Lys Xaa Thr Ile Ser Arg Ser Pro Gly Lys
                405                 410

<210> SEQ ID NO 16
<211> LENGTH: 234
<212> TYPE: PRT
<213> ORGANISM: artificial
<220> FEATURE:
<223> OTHER INFORMATION: light chain from clone 774206
```

<400> SEQUENCE: 16

```
Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Trp Tyr Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Ser Asp Pro Pro Thr Phe Gly Arg Gly Thr Lys Leu Glu Ile Lys
        115                 120                 125

Arg Ala Asp Ala Ala Pro Thr Val Ser Ile Phe Pro Pro Ser Ser Glu
130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
        210                 215                 220

Pro Ile Val Lys Ser Phe Asn Arg Asn Glu
225                 230
```

<210> SEQ ID NO 17
<211> LENGTH: 5
<212> TYPE: PRT
<213> ORGANISM: artificial
<220> FEATURE:
<223> OTHER INFORMATION: heavy chain CDR1 from clone 774206

<400> SEQUENCE: 17

```
Ser Tyr Ser Met Ser
1               5
```

<210> SEQ ID NO 18
<211> LENGTH: 17
<212> TYPE: PRT
<213> ORGANISM: artificial
<220> FEATURE:
<223> OTHER INFORMATION: heavy chain CDR2 from 774206

<400> SEQUENCE: 18

```
Tyr Ile Ser Asn Gly Gly Gly Ser Thr Tyr Tyr Pro Asp Thr Val Lys
1               5                   10                  15

Gly
```

<210> SEQ ID NO 19
<211> LENGTH: 10
<212> TYPE: PRT

```
<213> ORGANISM: artificial
<220> FEATURE:
<223> OTHER INFORMATION: heavy chain CDR3 from 774206

<400> SEQUENCE: 19

His Asp Gly Asn Tyr Pro Trp Phe Ala Tyr
1               5                   10

<210> SEQ ID NO 20
<211> LENGTH: 10
<212> TYPE: PRT
<213> ORGANISM: artificial
<220> FEATURE:
<223> OTHER INFORMATION: light chain CDR1 from 774206

<400> SEQUENCE: 20

Arg Ala Ser Ser Ser Val Ser Tyr Met His
1               5                   10

<210> SEQ ID NO 21
<211> LENGTH: 7
<212> TYPE: PRT
<213> ORGANISM: artificial
<220> FEATURE:
<223> OTHER INFORMATION: light chain CDR2 from 774206

<400> SEQUENCE: 21

Ala Thr Ser Asn Leu Ala Ser
1               5

<210> SEQ ID NO 22
<211> LENGTH: 9
<212> TYPE: PRT
<213> ORGANISM: artificial
<220> FEATURE:
<223> OTHER INFORMATION: light chain CDR3 from 774206

<400> SEQUENCE: 22

Gln Gln Trp Ser Ser Asp Pro Pro Thr
1               5
```